United States Patent
Sebti et al.

(10) Patent No.: US 9,822,135 B2
(45) Date of Patent: Nov. 21, 2017

(54) STAT3 DIMERIZATION INHIBITORS

(71) Applicant: H. LEE MOFFITT CANCER CENTER AND RESEARCH INSTITUTE, INC., Tampa, FL (US)

(72) Inventors: Said M. Sebti, Tampa, FL (US); Nicholas James Lawrence, Tampa, FL (US); Harshani Rithma Lawrence, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/435,471

(22) PCT Filed: Oct. 30, 2013

(86) PCT No.: PCT/US2013/067450
§ 371 (c)(1),
(2) Date: Apr. 14, 2015

(87) PCT Pub. No.: WO2014/070859
PCT Pub. Date: May 8, 2014

(65) Prior Publication Data
US 2015/0259366 A1   Sep. 17, 2015

Related U.S. Application Data

(60) Provisional application No. 61/720,234, filed on Oct. 30, 2012.

(51) Int. Cl.
| | |
|---|---|
| *A61K 31/192* | (2006.01) |
| *C07F 9/38* | (2006.01) |
| *C07F 9/40* | (2006.01) |
| *C07C 233/76* | (2006.01) |
| *C07C 311/18* | (2006.01) |
| *C07D 211/10* | (2006.01) |
| *C07D 213/16* | (2006.01) |

(52) U.S. Cl.
CPC .......... *C07F 9/3834* (2013.01); *A61K 31/192* (2013.01); *C07C 233/76* (2013.01); *C07C 311/18* (2013.01); *C07D 211/10* (2013.01); *C07D 213/16* (2013.01); *C07F 9/3882* (2013.01); *C07F 9/4021* (2013.01); *C07F 9/4056* (2013.01)

(58) Field of Classification Search
None
See application file for complete search history.

(56) References Cited

U.S. PATENT DOCUMENTS

| 6,093,730 A | 7/2000 | Weidmann et al. |
| 2010/0022482 A1 | 1/2010 | Baumann et al. |

FOREIGN PATENT DOCUMENTS

| EP | WO86/03199 | * | 6/1986 |
| JP | 09077751 A | | 3/1997 |
| WO | 8303199 A1 | | 3/1983 |
| WO | 2010141406 A2 | | 12/2010 |

OTHER PUBLICATIONS

Turkson, STAT proteins as novel targets for cancer drug discovery, Expert Opin Ther Tar, 8:409-422, 2004.
Turkson, et al., Phosphotyrosyl peptides block Stat3-mediated DNA binding activity, gene regulation, and cell transformation, J Biol Chem, 276:45443-45455, 2001.
Uehara, et al., Novel high-throughput screening system for identifying STAT3-SH2 antagonists, Biochem Biophys Res Commun, 380:627-631, 20096.
Urlam, et al., Development of new NArylbenzamides as STAT3 Dimerization Inhibitors, Medchemomm., 4(6):932-941, 2013.
Wang, et al., Palmitoylated cysteine 192 is required for RhoB tumor-suppressive and apoptotic activities, J Biol Chem, 280(19):19243-9, 2005.
Xie, et al., Stat3 activation regulates the expression of matrix metalloproteinase-2 and tumor invasion and metastasis, Oncogene, 23(20):3550-60, 2004.
Yap, et al., Small-molecule inhibitors of dimeric transcription factors: Antagonism of protein-protein and protein-DNA Interactions, Med Chem Comm, 3:541-551, 2012.
Ying, et al., Immunoglobulin light chains activate nuclear factor-kappaB in renal epithelial cells through a Src-dependent mechanism, Blood, 117(4):1301-7, 2011.
Yu, et al., Enhanced DNAbinding activity of a Stat3-related protein in cells transformed by the Src oncoprotein, Science, 269(5220):81-3, 1995.
Yu, et al., STATs in cancer inflammation and immunity: a leading role for STAT3, Nat Rev Cancer, 9(11):798-809, 2009.
Yu, et al., The STATs of cancer—new molecular targets come of age, Nat Rev Cancer, 4(2):97-105, 2004.
Yue, et al., Targeting STAT3 in cancer: how successful are we?, Expert Opin. Inv. Drug, 18:45-56, 2009.
Zhang, et al., A novel small-molecule disrupts Stat3 SH2 domain-phosphotyrosine interactions and Stat3-dependent tumor processes, Biochem Pharmacol, 79(10):1398-409, 2010.
Zhang, et al., Orally bioavailable small-molecule inhibitor of transcription factor Stat3 regresses human breast and lung cancer xenografts. Proceedings of the National Academy of Sciences of the United States of America, 109 (24):9623-8. Epub May 25, 2012. doi: 10.1073/pnas.1121606109, 2012.

(Continued)

*Primary Examiner* — Samantha Shterengarts
(74) *Attorney, Agent, or Firm* — Meunier Carlin & Curfman LLC

(57) ABSTRACT

The subject matter disclosed herein relates to compositions and methods of making and using the compositions. In a further aspect, the subject matter disclosed herein relates to inhibitors of STAT3 dimerization. Methods of making these compositions as well as compositions comprising these compositions are also disclosed. Also disclosed are methods of treating or preventing certain cancers by administering to an individual in need thereof and effective amount of the compounds disclosed herein. Still further, disclosed herein are methods of inhibiting STAT3 by contacting a cell with a compound or composition as disclosed herein.

17 Claims, 13 Drawing Sheets

(56) References Cited

OTHER PUBLICATIONS

Zhang, et al. A novel STAT3-STAT3 dimerization disruptor, S3I-1757, selectively suppresses STAT3 activity and malignant transformation, under review, x, 2012.
Zhang, et al., Orally bioavailable small-molecule inhibitor of transcription factor Stat3 regresses human breast and lung cancer xenografts, P. Natl. Acad. Sci. USA, 109, 9623-9628, 2012.
Zhao, et al., Small molecule inhibitors of STAT3 for cancer therapy, Curr. Med. Chem., 18:4012-4018, 2011.
Zhong, et al., Stat3: A STAT family member activated by tyrosine phosphorylation in response to epidermal growth factor and interleukin-6, Science, 264(5155):95-8. Epub, 1994.
International Search Report and Written Opinion for PCT/US2013/067450 dated Feb. 19, 2014.
International Preliminary Report on Patentability for PCT/US2013/067450 dated May 5, 2015.
Azumaya, et al., Simple and convenient synthesis of tertiary benzanilides using dichlorotriphenylphosphorane, Tetrahedron, 59:2325-2331, 2003.
Balasis, et al., Combination of famesyltransferase and Akt inhibitors is synergistic in breast cancer cells and causes significant breast tumor regression in ErbB2 transgenic mice, Clinical Cancer Res, 17(9):2852-62, 2011.
Barton, et al., Signal transducer and activator of transcription 3 (STAT3) activation in prostate cancer: Direct STAT3 inhibition induces apoptosis in prostate cancer lines, Mol Cancer Ther, 3:11-20, 2004.
Becker, et al., Three-dimensional structure of the Stat3 beta homodimer bound to DNA, Nature, 394:145-151, 1998.
Berishaj, et al., Stat3 is tyrosine-phosphorylated through the interleukin-6/glycoprotein 130/Janus kinase pathway in breast cancer, Breast Cancer Res, 9:R32, 2007.
Bessmertnykh, et al., Direct Synthesis of Amino-substituted Aromatic Phosphonates via Palladium-catalyzed Coupling of Aromatic Mono- and Dibromides with Diethyl Phosphite, Chem Lett, 38:738-739, 2009.
Bowman, et al., STATs in oncogenesis. Oncogene, 19:2474-2488, 2000.
Bromberg, et al., Stat3 as an oncogene, Cell, 98(3):295-303, 1999.
Bromberg, et al., The role of STATs in transcriptional control and their impact on cellular function, Oncogene, 19:2468-2473, 2000.
Brozic, et al., Selective inhibitors of aldo-keto reductases AKR1C1 and AKR1C3 discovered by virtual screening of a fragment library, J Med Chem, 55:7417-7424, 2002.
Buettner, et al., Activated STAT signaling in human tumors provides novel molecular targets for therapeutic Intervention, Clin Cancer Res, 8:945-954, 2002.
Burke, et al., Nonhydrolyzable Phosphotyrosyl Mimetics for the Preparation of Phosphatase-Resistant SH2 Domain Inhibitors, Biochemistry, 33:6490-6494, 1994.
Burke, et al., Inhibition of constitutively active Stat3 suppresses growth of human ovarian and breast cancer cells, Oncogene, 20:7925-7934, 2001.
Caldenhoven, et al., STAT3beta, a splice variant of transcription factor STAT3, is a dominant negative regulator of transcription, J Biol Chem, 271(22):13221-13227, 1996.
Chaturvedi, et al., Abrogation of interleukin-3 dependence of myeloid cells by the v-src oncogene requires SH2 and SH3 domains which specify activation of STATs, Mol Cell Biol, 17:3295-3304, 1997.
Chen, et al., Structure-Based Design of Conformationally Constrained, Cell-Permeable STAT3 Inhibitors, ACS Med Chem Lett, 1:85-89, 2010.
Coleman, et al., Investigation of the binding determinants of phosphopeptides targeted to the Src homology 2 domain of the signal transducer and activator of transcription 3. Development of a highaffinity peptide inhibitor, J Med Chem, 48:6661-6670, 2005.
Darnell, et al., Jak-STAT pathways and transcriptional activation in response to IFNs and other extracellular signaling proteins, Science, 264(5164):1415-21, 1994.
Darnell, Validating Stat3 in cancer therapy, Nat Med, 11:595-596, 2005.
Darnell, STATs and gene regulation, Science, 277:1630-1635, 1997.
Debnath, et al., Small Molecule Inhibitors of Signal Transducer and Activator of Transcription 3 (Stat3) Protein, J Med Chem 2012.
Feng, et al., Synthesis and Immunomodulating Activity of New Analogues of Fingolimod, Archiv der Pharmazie, 345:93-100, 2012.
Fletcher, et al., Disruption of Transcriptionally Active Stat3 Dimers with Non-phosphorylated, Salicylic Acid-Based Small Molecules: Potent in vitro and Tumor Cell Activities, Chem Bio Chem, 10:1959-1964, 2009.
Fletcher, et al., Antagonism of the Stat3-Stat3 Protein Dimer with Salicylic Acid Based Small Molecules, Chem Med Chem, 6:1459-1470, 2011.
Haan, et al., Characterization and binding specificity of the monomeric STAT3-SH2 domain, J Biol Chem 274(3):1342-8, 1999.
Hao, et al., Discovery of the catechol structural moiety as a Stat3 SH2 domain inhibitor by virtual screening, Bioorg Med Chem Lett, 18:4988-4992, 2008.
Krueger, et al., The v-src oncogene blocks the differentiation of a murine myeloid progenitor cell line and induces a tumorigenic phenotype, Oncogene, 6:245-56, 1991.
Lavecchia, et al., STAT-3 inhibitors: state of the art and new horizons for cancer treatment, Curr Med Chem, 18:2359-2375, 2011.
Lee, et al., Novel E coli b-ketoacyl-acryl carrier protein synthase III inhibitors as targeted antibiotics, Biorg Med Chem 17:1506-1513, 2009.
Lin, et al. The STAT3 inhibitor NSC 74859 is effective in hepatocellular cancers with disrupted TGF-[beta] signaling, Oncogene, 28:961-972, 2009.
Mandal, et al., Conformationally Constrained Peptidomimetic Inhibitors of Signal Transducer and Activator of Transcription 3: Evaluation and Molecular Modeling, J Med Chem 52:2429-2442, 2009.
Mandal, et al., Structure-Affinity Relationships of Glutamine Mimics Incorporated into Phosphopeptides Targeted to the SH2 Domain of Signal Transducer and Activator of Transcription 3, J Med Chem, 52:6126-6141, 2009.
Mandal, et al., Potent and Selective Phosphopeptide Mimetic Prodrugs Targeted to the Src Homology 2 (SH2) Domain of Signal Transducer and Activator of Transcription 3, J Med Chem, 54:3549-3563, 2011.
Mankan, et al., Inhibiting signal transducer and activator of transcription 3: rationality and rationale design of inhibitors, Expert Opin Inv Drug, 20:1263-1275, 2011.
Masciocchi, et al., Signal transducer and activator of transcription 3 (STAT3): a promising target for anticancer therapy, Future Medicinal Chemistry, 3:567-597, 2011.
Matsuno, et al., Identification of a New Series of STAT3 Inhibitors by Virtual Screening, ACS Med Chem Lett, 1:371-375, 2010.
Niu, et al., Gene therapy with dominant-negative Stat3 suppresses growth of the murine melanoma B16 tumor in vivo, Cancer Res, 59(20):5059-63, 1999.
Page, et al., Signal transducer and activator of transcription 3 inhibitors: a patent review, Expert Opin Ther Pat, 21:65-83, 2011.
Park, et al., Characterization of molecular recognition of STAT3 SH2 domain inhibitors through molecular simulation, J Mol Recognit, 24:254-265, 2011.
Ramunno, et al., Progresses in the pursuit of aldose reductase inhibitors: The structure-based lead optimization step, Eur J Med Chem, 51:216-226, 2012.
Ren, et al., Identification of Niclosamide as a New Small-Molecule Inhibitor of the STAT3 Signaling Pathway, ACS Med Chem Lett, 1:454-459, 2010.
Ren, et al., Identification of a High-Affinity Phosphopeptide Inhibitor of Stat3, Bioorg Med Chem Lett, 13(4):633-636, 2003.
Schust, et al., A high-throughput fluorescence polarization assay for signal transducer and activator of transcription 3, Anal Biochem, 330:114-118, 2004.
Schust, et al., A Small-Molecule Inhibitor of STAT3 Activation and Dimerization, Chem Biol, 13:1235-1242, 2006.

(56) References Cited

OTHER PUBLICATIONS

Shahani, et al., Identification of purine-scaffold small-molecule inhibitors of Stat3 activation by QSAR studies, ACS Med Chem Lett, 2:79-84, 2011.

Shao, et al., Identification and characterization of signal transducer and activator of transcription 3 recruitment sites within the epidermal growth factor receptor, Cancer Res, 63(14):3923-30, 2003.

Siddiquee, et al., An Oxazole-Based Small-Molecule Stat3 Inhibitor Modulates Stat3 Stability and Processing and Induces Antitumor Cell Effects, ACS Chem Biol, 2:787-798, 2007.

Siddiquee, et al., Selective chemical probe inhibitor of Stat3, identified through structure-based virtual screening, induces antitumor activity, P Natl Acad Sci USA, 104:7391-7396, 2007.

Song, et al., A low-molecular-weight compound discovered through virtual database screening inhibits Stat3 function in breast cancer cells, P Natl Acad Sci USA, 102:4700-4705, 2005.

Song, Ji; et al., STAT signaling in head and neck cancer, Oncogene, 19:2489-2495, 2000.

\* cited by examiner

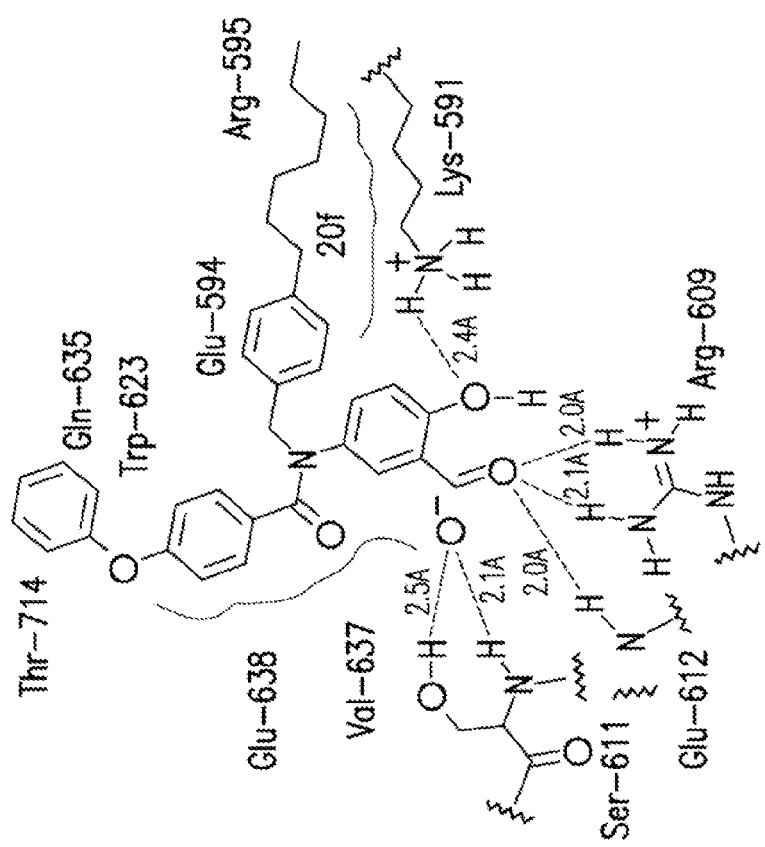
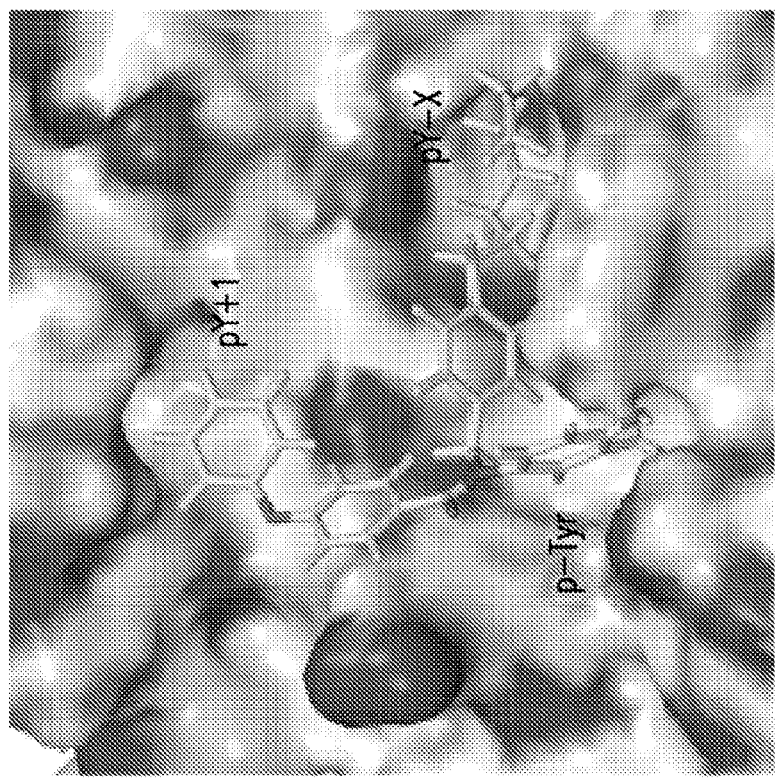
FIG. 4B
FIG. 4A

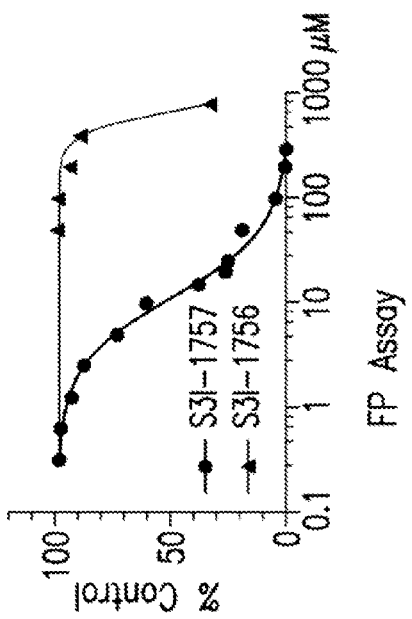
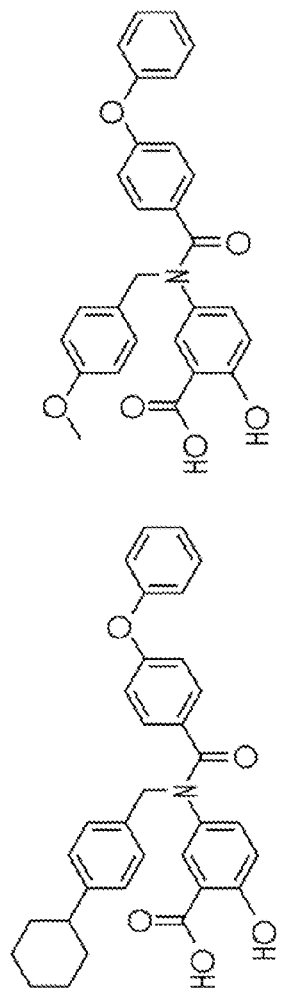
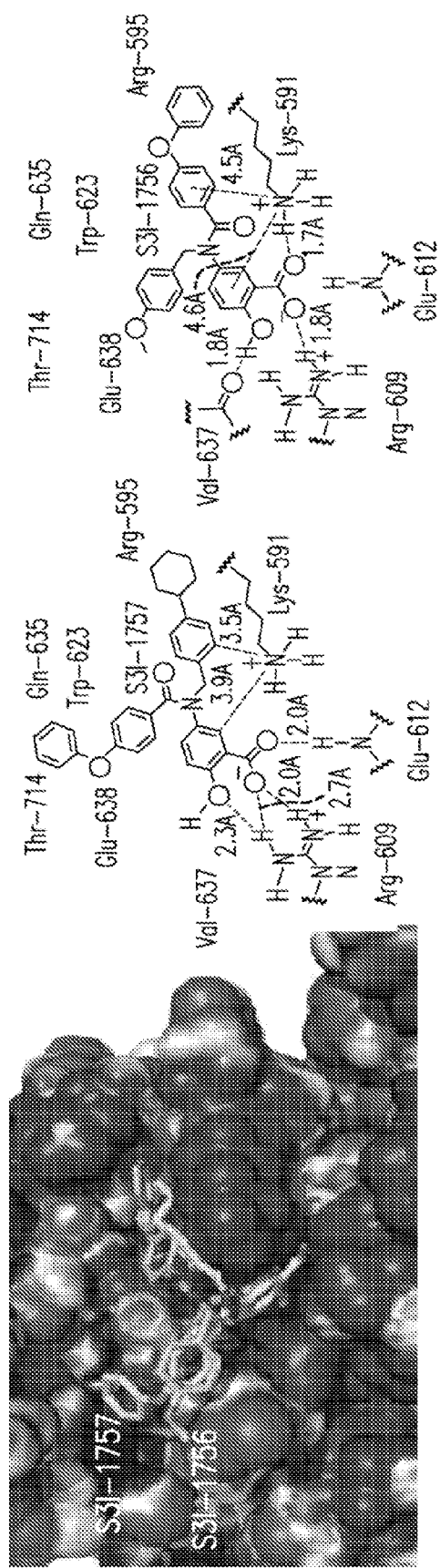
FIG. 5A
FIG. 5B

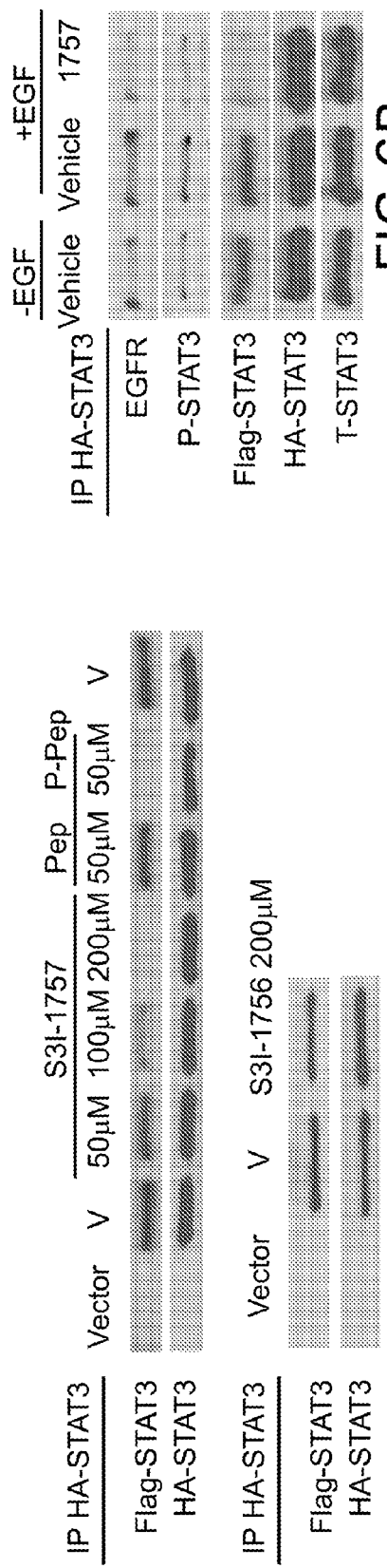
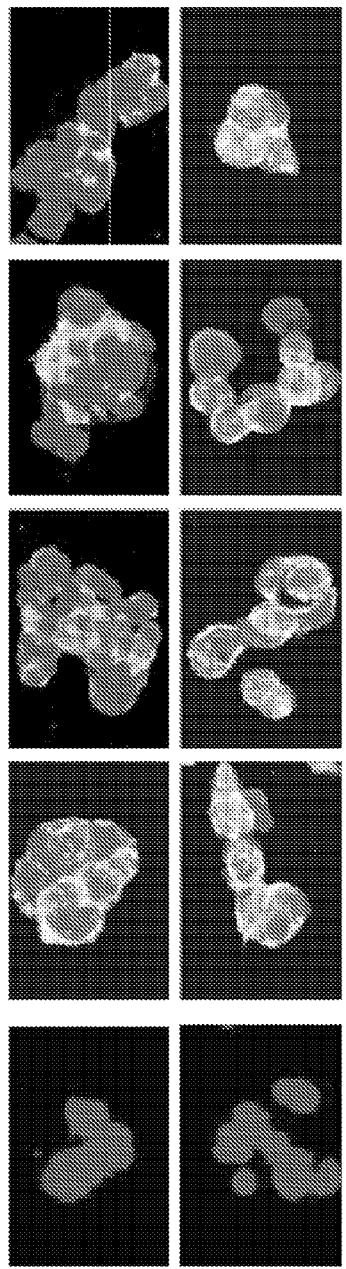
FIG.6A
FIG.6B
FIG.6C

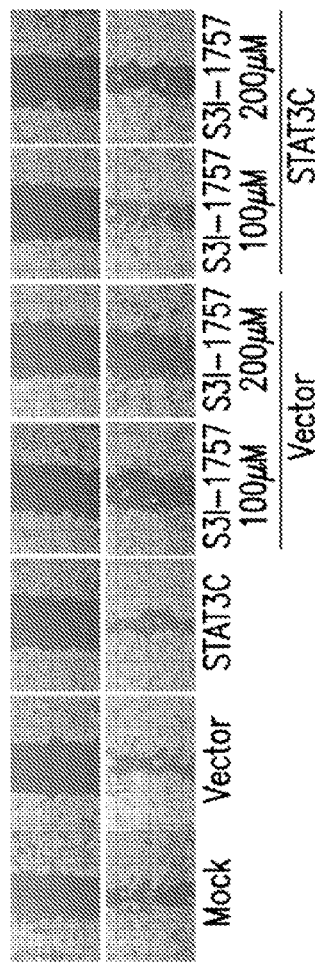
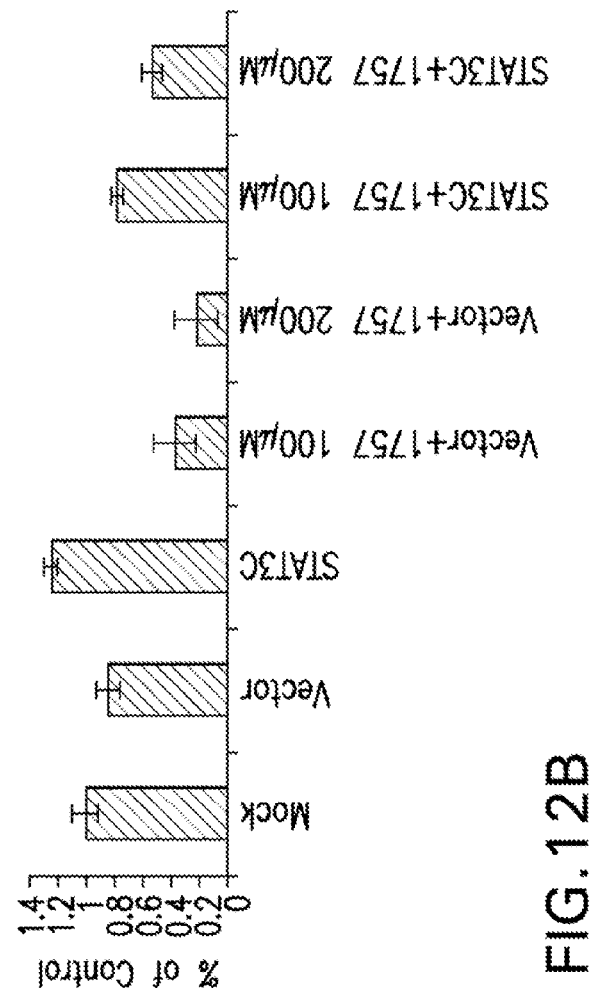
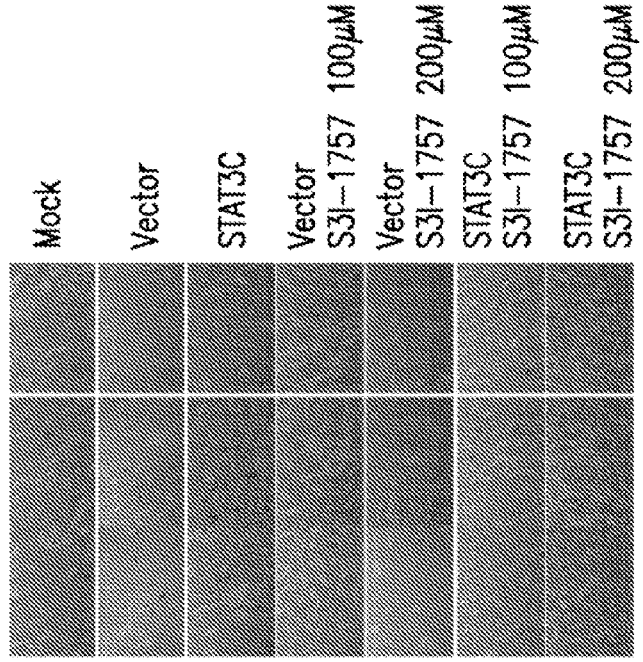
FIG.12A
FIG.12B

STAT3 DIMERIZATION INHIBITORS

CROSS REFERENCE TO RELATED APPLICATION

This application claims the benefit of priority to U.S. Provisional Application No. 61/720,234, filed Oct. 30, 3012, which is incorporated by reference herein in its entirety.

ACKNOWLEDGEMENT OF GOVERNMENT SUPPORT

This invention was made with government support under grant no CA140681 awarded by the National Institutes of Health. The government has certain rights in this invention.

BACKGROUND

Signal Transducer and Activator of Transcription 3 (STAT3) is a signal transducer and activator of transcription that transmits signals from cell surface receptors to the nucleus. STAT3 is frequently hyperactivated in many human cancers. Under normal conditions, STAT3 activation is transient and tightly regulated. Upon cellular stimulation by ligands such as growth factors or cytokines, STAT3 become phosphorylated on critical tyrosine residue (Tyr705) and consequently induce STAT3 dimerization through two reciprocal phosphotyrosine (pTyr)-Src-homology 2 (SH2) interactions. The STAT3 dimers then translocate to the nucleus and bind to specific DNA-response elements in the promoters of target genes thereby activating transcription. The association of aberrant STAT3 activation with many types of human malignancies and solid tumors has made STAT3 an attractive molecular target for the development of novel cancer therapeutics. (See Darnell, *Science* 1997; 277:630-1635; Darnell, *Nat. Med.* 2005; 11:595-596; Bromberg, *Oncogene* 2000; 19:2468-2473; Yu, *Nat. Rev. Cancer* 2004; 4:97-105; Bowman, *Oncogene* 2000; 19:2474-2488; Yue, *Expert Opin. Inv. Drug* 2009; 18:45-56.)

STAT3 is found to be constitutively activated in tumor cells and contribute to tumor progression through the modulation of some target genes, such as antiapoptotic genes Bcl-xL, Bcl-2, Mcl-1 and survivin along with genes driving cell cycle progression, c-Myc and cyclin-D1. (Id.; Buettner, *Clin. Cancer Res.* 2002; 8:945-954.) Aberrant activation of STAT3 is most frequent in almost all blood malignancies and solid tumors, including lymphoma and leukemia, breast, prostate, lung head and neck, brain and colon cancer. (See Turkson, *Expert Opin. Ther. Tar.* 2004; 8:409-422. Burke, et al., *Oncogene* 2001; 20:7925-7934; Berishaj, et al., *Breast Cancer Res* 2007; 9:R32; Barton, et al., *Mol. Cancer Ther.* 2004; 3:11-20; Krueger, et al., *Oncogene* 1991:6; 245-56; Chaturvedi, *Mol. Cell. Biol.* 1997; 17:3295-3304; Song, *Oncogene* 2000; 19:2489-2495.) These features have made STAT3 an attractive target for the development of anticancer agents.

The design of compounds that target STAT3 has been the subject of several recent reviews. (See Mankan, et al., *Expert Opin. Inv. Drug* 2011; 20:1263-1275; Lavecchia, et al., *Curr. Med. Chem.* 2011; 18:2359-2375; Yap, *Med. Chem. Comm* 2012; 3:541-551; Masciocchi, et al., *Future Medicinal Chemistry* 2011; 3:567-597; Zhao, et al., *Curr. Med. Chem.* 2011, 18, 4012-4018.) The direct targeting of STAT3 is a particularly attractive way to inhibit its function. Several approaches have been taken to inhibit the dimerization of phosphorylated STAT3 by blocking the SH2 domain binding site of the phosphorylated STAT3 tyrosine-705 residue. The first inhibitors of STAT3 dimerization were peptides and phosphopeptides (Turkson, et al., *J. Biol. Chem.* 2001; 276:45443-45455; Coleman, et al., *J. Med. Chem.* 2005; 48:6661-6670). Significant advances have been made by the groups of McMurray (Mandal, et al., *J. Med. Chem.* 2011; 54:3549-3563; Mandal, et al., *J. Med. Chem.* 2009; 52:2429-2442; Mandal, et al., *J. Med. Chem.* 2009; 52:6126-6141) and Wang (Chen, et al., *ACS Med. Chem. Lett.* 2010; 1:85-89) by using structure-based approaches resulting in potent peptide-like inhibitors incorporating a phosphotyrosine residue. These potent cell permeable STAT3 dimerization inhibitors have considerable ADME liabilities since the high affinity SH2 domain binding derives, at least in part, from the necessary presence of a hydrolyzable phosphate group.

As an alternative approach considerable attention has been paid to the discovery of non-peptidic small molecule drug-like inhibitors of STAT3 dimerization to avoid some of the ADME challenges inherent in the development of peptide-like inhibitors. (See Fletcher, et al., *Chem. Bio. Chem.* 2009; 10:1959-1964; Hao, et al., *Bioorg. Med. Chem. Lett.* 2008; 18:4988-4992; Matsuno, et al., *ACS Med. Chem. Lett.* 2010; 1:371-375; Ren, et al., *ACS Med. Chem. Lett.* 2010; 1:454-459; Schust et al., *Chem. Biol.* 2006; 13:1235-1242; Shahani, et al., *ACS Med. Chem. Lett.* 2011; 2:79-84; Siddiquee, et al., *ACS Chem. Biol.* 2007; 2:787-798; Song, et al., *P. Natl. Acad. Sci. USA* 2005; 102:4700-4705; Uehara, et al., *Biochem. Biophys. Res. Commun.* 2009; 380:627-631.) What are needed are new STAT3 inhibitors and methods of making and using same. The compounds, compositions, and methods disclosed herein address these and other needs.

SUMMARY

The subject matter disclosed herein relates to compositions and methods of making and using the compositions. In a further aspect, the subject matter disclosed herein relates to inhibitors of STAT3 dimerization. Methods of making these compositions as well as compositions comprising these compositions are also disclosed. Also disclosed are methods of treating or preventing certain cancers by administering to an individual in need thereof and effective amount of the compounds disclosed herein. Still further, disclosed herein are methods of inhibiting STAT3 by contacting a cell with a compound or composition as disclosed herein.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 4 shows the salicylic acid 20f docked to the STAT3 SH2 domain. a: is a surface rendering of 20f docked to the STAT3 p-Tyr binding site. b: is a schematic binding mode of 20f to the STAT3 SH2 domain showing the hydrogen bonds and hydrophobic interactions.

FIG. 5A shows the chemical structures of S3I-1757 (compound 20g) and S3I-1756 (compound 20b). FIG. 5B shows the effects of S3I-1757 and S3I-1756 on the binding of STAT3 to fluorescein-labelled GpYLPQTV phophotyrosine peptide was determined by FP assays. Solvent accessible surface (probe radius of 0.75 A) of the STAT3 SH2 domain color coded by electrostatic potential calculated using the APBS plugin in PyMol.

FIG. 6A shows results from a co-immuno-precipitation assay. HEK293 cells stably co-expressing FLAG- and HA-tagged STAT3 were treated with either vehicle, Ac-G{pTYR}LPQTV-AAVLLPVLLAAP-NH$_2$ (phospho-peptide with MTS) (SEQ ID NO.:1), Ac-GYLPQTV-AAVLLPVLLAAP-NH$_2$ (non-phospho-peptide with MTS) (SEQ ID NO.:2), S3I-1757 or S3I-1756 at the indicated concentration, processed for immuno-precipitation with HA antibody and immuno-blotting with FLAG antibody. FLAG-STAT3 coimmuno-precipitated with HA-STAT3 in HEK293 cells that co-express HA-STAT3 and FLAG-STAT3 but not in vector transfected HEK293 cells. Ac-G{pTYR}LPQTV-AAVLLPVLLAAP-NH2 (phospho19 peptide) but not Ac-GYLPQTV-AAVLLPVLLAAP-NH2 inhibited the binding of FLAG-STAT3 to HASTAT3. S3I-1757 but not S3I-1756 inhibited the binding of FLAG-STAT3 to HA-STAT3. FIG. 6B shows HEK293 cells stably co-expressing FLAG- and HA-tagged STAT3 were treated as described in (A) except that prior to treating with S3I-1757, they were first treated either with vehicle or EGF. The cells were then immuno-precipitated with HA antibody and blotted with antibodies to EGFR, P-Y-705-STAT3, FLAG, HA or total STAT3 as described in Methods. Results are representative of 3 independent experiments. FIG. 6C shows results from a co-localization assay where HEK293 cells stably co-expressing FLAG- and HAtagged STAT3 were plated on cover slides over night and then treated with either vehicle, S3I-1757 or S3I-1756 for 0, 1, 2 or 4 hours and processed for co-localization studies with HA-STAT3 and FLAG-STAT3 as described under Methods. Data are representative of 3 independent experiments.

FIG. 12 shows results from where MDAMB-468 cells were transiently transfected with vector or STAT3C, plated either for migration (A) or invasion (B) and then treated with S3I-1757. The cells were then processed for migration (A) and invasion (B) assays.

DETAILED DESCRIPTION

Figure 1:
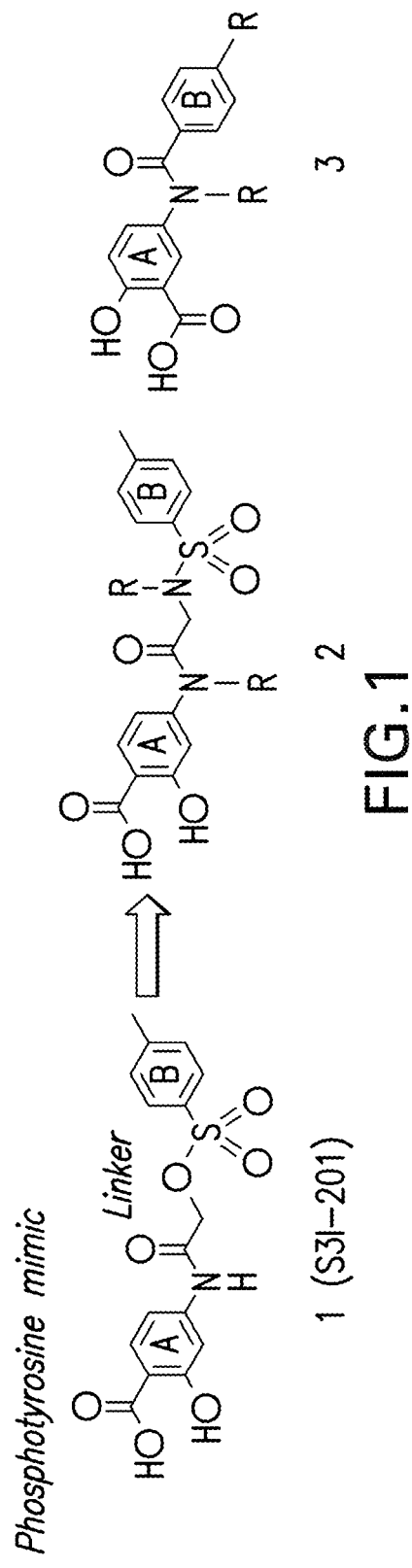
FIG. 1 is a chemical scheme showing the structures of S3I-201 (1, NSC-74859) and scaffolds 2 and 3.

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like.

Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are compounds having Formula I

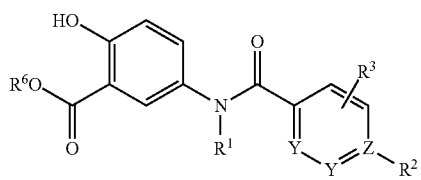

I wherein, $R^1$ is H, $C_1$-$C_{10}$ alkyl, $C(O)C_1$-$C_{10}$ alkyl, $CO_2C_1$-$C_{10}$ alkyl, benzyl, 4-piperidyl, 3-(4-pyridyl), pyridinyl, or

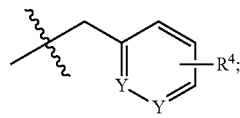

wherein $R^4$ is OH, Cl, F, Br, I, cyclohexyl, $OC_1$-$C_{10}$ alkyl, $C_1$-$C_{10}$ alkyl, $C(O)C_1$-$C_{10}$ alkyl, $CO_2C_1$-$C_{10}$ alkyl, 4-piperidyl, 3-(4-pyridyl), morpholinyl, pyridinyl, OPh, $PO(OEt)_2$, or $PO(OH)_2$; $R^2$ is null, H, OH, Cl, F, Br, I, $NH_3$, $OC_1$-$C_{10}$ alkyl, cyclohexyl, $C_1$-$C_{10}$ alkyl, $C(O)C_1$-$C_{10}$ alkyl, $CO_2C_1$-$C_{10}$ alkyl, 4-piperidyl, 3-(4-pyridyl), morpholinyl, pyridinyl, phenyl, halogenated phenyl, $PO(OEt)_2$, $PO(OH)_2$ or

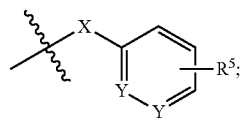

wherein X is O, NH, S, or $CH_2$, and $R^5$ is H, OH, Cl, F, Br, I, cyclohexyl, or $C_1$-$C_{10}$ alkyl; $R^3$ is H, OH, Cl, F, Br, I, $OC_1$-$C_{10}$ alkyl, $C_1$-$C_{10}$ alkyl, $C(O)C_1$-$C_{10}$ alkyl, $CO_2C_1$-$C_{10}$ alkyl, $NO_2$, $NH_3$, or CN; and $R^6$ is H, $C_1$-$C_{10}$ alkyl, or a pharmaceutically acceptable counterion; each Y is, independent of the others, CH or N; and Z is C or N; or a pharmaceutically acceptable salt thereof.

In certain examples, compounds of Formula I can have $R^1$ as H, $C_1$-$C_{10}$ alkyl, $C(O)C_1$-$C_{10}$ alkyl, $CO_2C_1$-$C_{10}$ alkyl, benzyl, 4-piperidyl, 3-(4-pyridyl), or pyridinyl. In other examples, $R^1$ can be

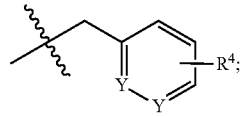

where each Y is CH, and $R^4$ is OH, Cl, F, Br, I, cyclohexyl, $C_1$-$C_{10}$ alkyl, 4-piperidyl, 3-(4-pyridyl), morpholinyl, pyridinyl, or OPh. In still other examples, $R^1$ can be

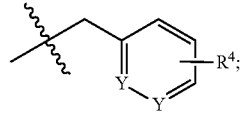

wherein each Y is CH, and $R^4$ is cyclohexyl, $C_1$-$C_{10}$ alkyl, 4-piperidyl, 3-(4-pyridyl), morpholinyl, or pyridinyl, more preferably $R^4$ is cyclohexyl and each Y is CH.

In certain examples, compounds of Formula I can have $R^2$ as OH, Cl, F, Br, I, $OCH_3$, $C_1$-$C_{10}$ alkyl, 4-piperidyl, 3-(4-pyridyl), morpholinyl, phenyl, or pyridinyl. In still other examples, $R^2$ can be

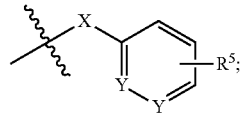

wherein each Y is CH, and $R^5$ is H, OH, Cl, F, Br, or I. In a preferred example, X can be O, for example, when $R^2$ is OPh.

In certain examples, compounds of Formula I can have $R^3$ is H or $OCH_3$.

Specific examples of compounds of Formula I are shown in Table 3. One preferred compound has the following compound.

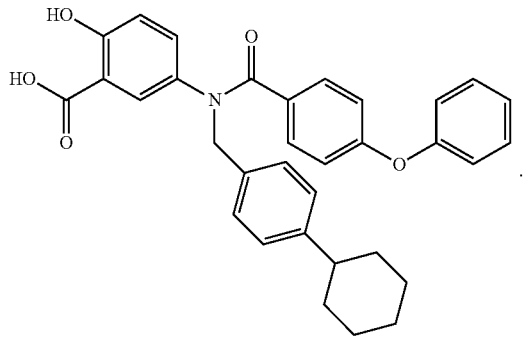 [SMILES: O=C(O)c1cc(N(Cc2ccc(C3CCCCC3)cc2)C(=O)c2ccc(Oc3ccccc3)cc2)ccc1O]

Disclosed herein are compounds that hay Formula II:

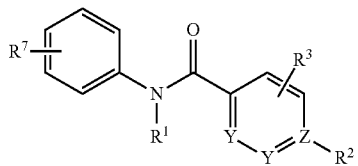

wherein $R^1$ is H, $C_1$-$C_{10}$ alkyl, $C(O)C_1$-$C_{10}$ alkyl, $CO_2C_1$-$C_{10}$ alkyl, benzyl, 4-piperidyl, 3-(4-pyridyl), pyridinyl, or

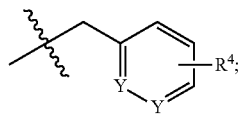

wherein $R^4$ is OH, Cl, F, Br, I, cyclohexyl, $OC_1$-$C_{10}$ alkyl, $C_1$-$C_{10}$ alkyl, $C(O)C_1$-$C_{10}$ alkyl, $CO_2C_1$-$C_{10}$ alkyl, 4-piperidyl, 3-(4-pyridyl), morpholinyl, pyridinyl, OPh, $PO(OEt)_2$, or $PO(OH)_2$; $R^2$ is null, H, OH, Cl, F, Br, I, $NH_3$, $OC_1$-$C_{10}$ alkyl, cyclohexyl, $C_1$-$C_{10}$ alkyl, $C(O)C_1$-$C_{10}$ alkyl, $CO_2C_1$-$C_{10}$ alkyl, 4-piperidyl, 3-(4-pyridyl), morpholinyl, pyridinyl, phenyl, halogenated phenyl, $PO(OEt)_2$, $PO(OH)_2$ or

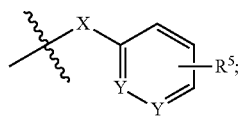

wherein X is O, NH, S, or $CH_2$, and $R^5$ is H, OH, Cl, F, Br, I, cyclohexyl, or $C_1$-$C_{10}$ alkyl; $R^3$ is H, OH, Cl, F, Br, I, $OC_1$-$C_{10}$ alkyl, $C_1$-$C_{10}$ alkyl, $C(O)C_1$-$C_{10}$ alkyl, $CO_2C_1$-$C_{10}$ alkyl, $NO_2$, $NH_3$, or CN; $R^7$ is $CH_2PO(OH)_2$, $PO(OEt)_2$, or $PO(OH)_2$; each Y is, independent of the others, CH or N; and Z is C or N; or a pharmaceutically acceptable salt thereof.

In certain examples, compounds of Formula II can have $R^1$ as H, $C_1$-$C_{10}$ alkyl, $C(O)C_1$-$C_{10}$ alkyl, $CO_2C_1$-$C_{10}$ alkyl, benzyl, 4-piperidyl, 3-(4-pyridyl), or pyridinyl. In still other examples, compounds of Formula II can have $R^1$ as

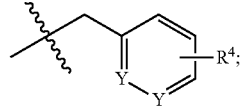

where each Y is CH, and $R^4$ is OH, Cl, F, Br, I, cyclohexyl, $C_1$-$C_{10}$ alkyl, 4-piperidyl, 3-(4-pyridyl), morpholinyl, pyridinyl, or OPh. In a other examples, $R^1$ can be

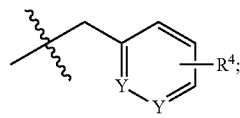

wherein each Y is CH, and $R^4$ is cyclohexyl, $C_1$-$C_{10}$ alkyl, 4-piperidyl, 3-(4-pyridyl), morpholinyl, or pyridinyl, more preferably $R^4$ can be cyclohexyl and each Y can be CH.

In certain examples, compounds of Formula II can have $R^2$ as OH, Cl, F, Br, I, $OCH_3$, $C_1$-$C_{10}$ alkyl, 4-piperidyl, 3-(4-pyridyl), morpholinyl, phenyl, or pyridinyl. In still other examples, compounds of Formula II can have $R^2$ as

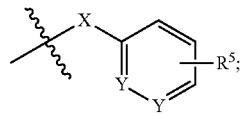

wherein each Y is CH, and $R^5$ is H, OH, Cl, F, Br, or I. In a preferred example, X can be O, such as when $R^2$ is OPh.

In certain examples, compounds of Formula II can have $R^3$ as H or $OCH_3$.

Also, disclosed herein are compounds having Formula III:

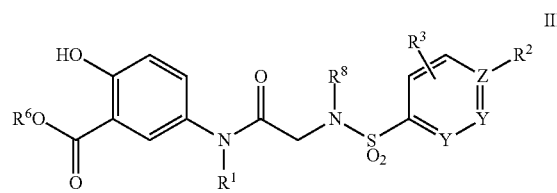

wherein $R^1$ is H, $C_1$-$C_{10}$ alkyl, $C(O)C_1$-$C_{10}$ alkyl, $CO_2C_1$-$C_{10}$ alkyl, benzyl, 4-piperidyl, 3-(4-pyridyl), pyridinyl, or

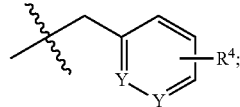

wherein $R^4$ is OH, Cl, F, Br, I, cyclohexyl, $OC_1$-$C_{10}$ alkyl, $C_1$-$C_{10}$ alkyl, $C(O)C_1$-$C_{10}$ alkyl, $CO_2C_1$-$C_{10}$ alkyl, 4-piperidyl, 3-(4-pyridyl), morpholinyl, pyridinyl, OPh, $PO(OEt)_2$, or $PO(OH)_2$; $R^2$ is null, H, OH, Cl, F, Br, I, $NH_3$, $OC_1$-$C_{10}$ alkyl, cyclohexyl, $C_1$-$C_{10}$ alkyl, $C(O)C_1$-$C_{10}$ alkyl, $CO_2C_1$-$C_{10}$ alkyl, 4-piperidyl, 3-(4-pyridyl), morpholinyl, pyridinyl, phenyl, halogenated phenyl, $PO(OEt)_2$, $PO(OH)_2$ or

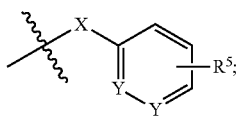

wherein X is O, NH, S, or $CH_2$, and $R^5$ is H, OH, Cl, F, Br, I, cyclohexyl, or $C_1$-$C_{10}$ alkyl; $R^3$ is H, OH, Cl, F, Br, I, $OC_1$-$C_{10}$ alkyl, $C_1$-$C_{10}$ alkyl, $C(O)C_1$-$C_{10}$ alkyl, $CO_2C_1$-$C_{10}$ alkyl, $NO_2$, $NH_3$, or CN; and $R^6$ is H, $C_1$-$C_{10}$ alkyl, or a pharmaceutically acceptable counterion; $R^8$ is H, $C_1$-$C_{10}$ alkyl, $C(O)C_1$-$C_{10}$ alkyl, $CO_2C_1$-$C_{10}$ alkyl, or benzyl; each Y is, independent of the others, CH or N; and Z is C or N; or a pharmaceutically acceptable salt thereof.

In certain examples, compounds of Formula III can have $R^1$ as H, $C_1$-$C_{10}$ alkyl, $C(O)C_1$-$C_{10}$ alkyl, $CO_2C_1$-$C_{10}$ alkyl, benzyl, 4-piperidyl, 3-(4-pyridyl), or pyridinyl. In still other examples, compounds of Formula III can have $R^1$ as

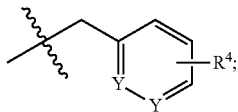

where each Y is CH, and $R^4$ is OH, Cl, F, Br, I, cyclohexyl, $C_1$-$C_{10}$ alkyl, 4-piperidyl, 3-(4-pyridyl), morpholinyl, pyridinyl, or OPh. In still other examples, $R^1$ can be

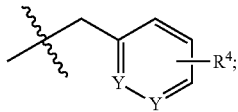

wherein each Y is CH, and $R^4$ is cyclohexyl, $C_1$-$C_{10}$ alkyl, 4-piperidyl, 3-(4-pyridyl), morpholinyl, or pyridinyl. In a preferred example, $R^4$ can be cyclohexyl.

In certain examples, compounds of Formula III can have $R^2$ as OH, Cl, F, Br, I, $OCH_3$, $C_1$-$C_{10}$ alkyl, 4-piperidyl, 3-(4-pyridyl), morpholinyl, phenyl, or pyridinyl. In still other examples, compounds of Formula III can have $R^2$ as

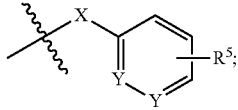

wherein each Y is CH, and $R^5$ is H, OH, Cl, F, Br, or I. In a preferred example, compounds of Formula III can have X as O, such as when $R^2$ is OPh.

In certain examples, compounds of Formula III can have $R^3$ is H or $OCH_3$. In a preferred example, compounds of Formula III can have $R^8$ as methyl or benzyl.

The first demonstration that STAT3 is involved in malignant transformation (Yu, et al., *Science* 1995; 169(5220): 81-83) was reported in 1995 only a year after its discovery (Zhong, et al., *Science* 1994; 264(5155):95-98). Less than 6 years later peptides and peptide mimics of the phosphotyrosine peptide PpYLKTK that bind STAT3 SH2 domain were shown to inhibit STAT3 dimerization in vitro and STAT3 activity in intact cells (Turkson, et al., *J. Biol. Chem.* 2001; 276(48):45443-45455). Yet, years later, there are no small molecule STAT3 dimerization inhibitors in clinical trials. One of the major reasons for this is that STAT3-STAT3 dimerization is a protein-protein interaction that involves a large surface area which is difficult to target with drug-like small molecules. The second reason, which is even more challenging, is that the negatively charged phosphotyrosine which is required for binding to the SH2 domain is difficult to mimic with moieties that can be easily taken up by cells. Nevertheless, because of the critical role of STAT3 in oncogenesis, several groups have put major efforts towards developing STAT3 dimerization inhibitors based on Phospho-peptide mimics as novel anti cancer drugs (Debnath, et al., *J. Med. Chem.* 2012:doi.10.1021/jm300207s; Masciocchi, et al., *Future Med. Chem.* 2011:3(5)567-597). For example, McMurray and colleagues have succeeded at obtaining cell permeable peptidomimetics of pYLPQ where pY was replaced by phosphocinnamide derivatives to improve peptidase resistance and used the pivaloyloxymethyl prodrug strategy to improve cellular uptake which lead to potent inhibition of STAT3 activity in whole cells (Mandal, et al., *J. Med. Chem.* 2011; 54(10):3549-3563). Similarly, Wang and colleagues (Chen, et al., *ASC Med. Chem. Lett.* 2010; 1(2):85-59) have also succeeded at designing a conformationally constrained pYLPQTV peptidomimetic with a long hydrocarbon chain to improve cell permeability. Although these are outstanding achievements, there still remain physicochemical challenges concerning the use of phospho-tyrosine peptidomimetics in vivo. Therefore, non-peptidic small molecules capable of disrupting STAT3-STAT3 dimerization is an attractive alternative approach to inhibiting STAT3 directly.

STAT3 inhibitor S3I-201 (NSC-74859) (Siddiquee, et al., *P. Natl. Acad. Sci. USA* 2007; 104:7391-7396) (FIG. 1) was identified from the NCI chemical collection by using structure-based virtual screening with a model based on the X-ray crystal structure of the STAT3 homodimer (pdb code 1BG1) (Becker, et al., *Nature* 1998; 394:145-151). S3I-201 inhibited STAT3:STAT3 complex formation and STAT3 DNA-binding and transcriptional activities. Furthermore, S3I-201 has been shown to exert antitumor effects against human breast and liver cancer xenografts in mouse models via mechanisms that are consistent with inhibition of STAT3 dimerization.

Disclosed herein are analogs of S3I-201 (1). Gunning and Turkson have developed a series of analogs of 1 based on an N-sulfonylglycine scaffold as in 2 (Fletcher, et al., *ChemBioChem* 2009; 10:1959-1964; Fletcher, et al., *Chem. Med. Chem.* 2011; 6:1459-1470; Zhang, et al., *P. Natl. Acad. Sci. USA* 2012; 109:9623-9628).

In the compounds disclosed herein there is a replacement of the potentially reactive O-sulfonylglycine portion of 1, and it is shown that the sulfonyloxy linker separating the two aryl groups by 5 atoms can be replaced by a shorter linker as in 3, leading to STAT3 dimerization inhibitors with improved potency. It is also shown herein that the phospho-tyrosine mimicking 4-amino-2-hydroxybenzoic acid can be replaced by its isomeric partner 5-amino-2-hydroxybenzoic acid.

Scheme 1. Synthetic route to library 9

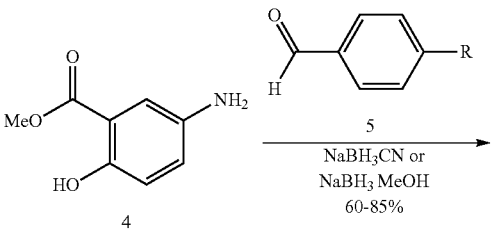

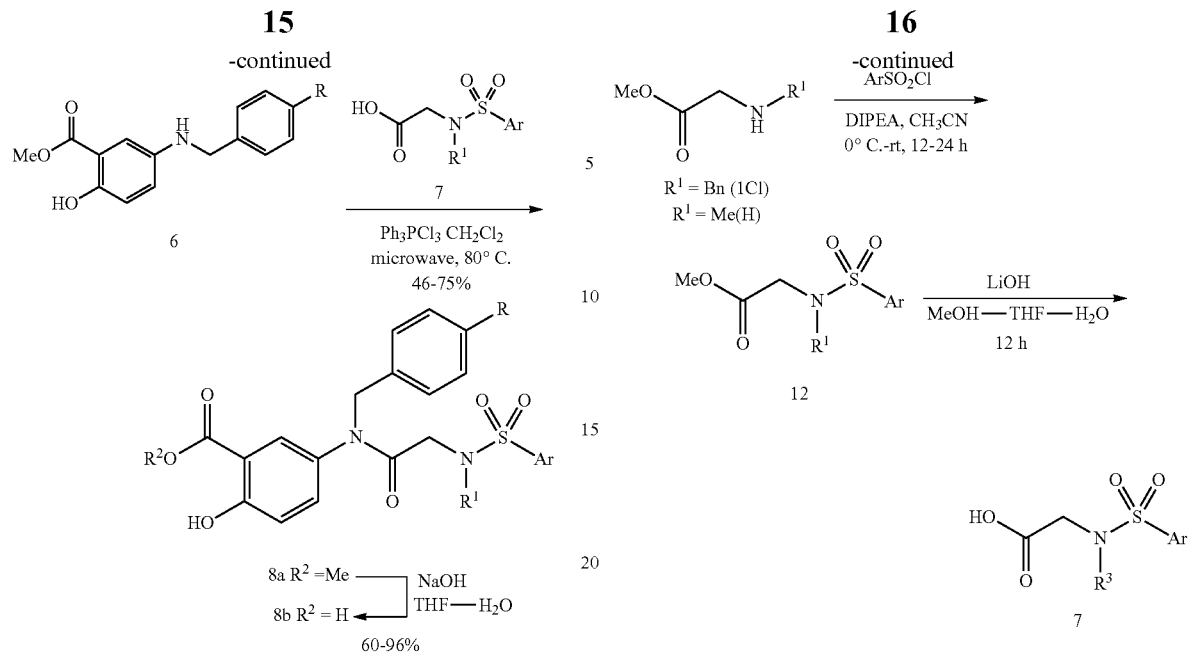
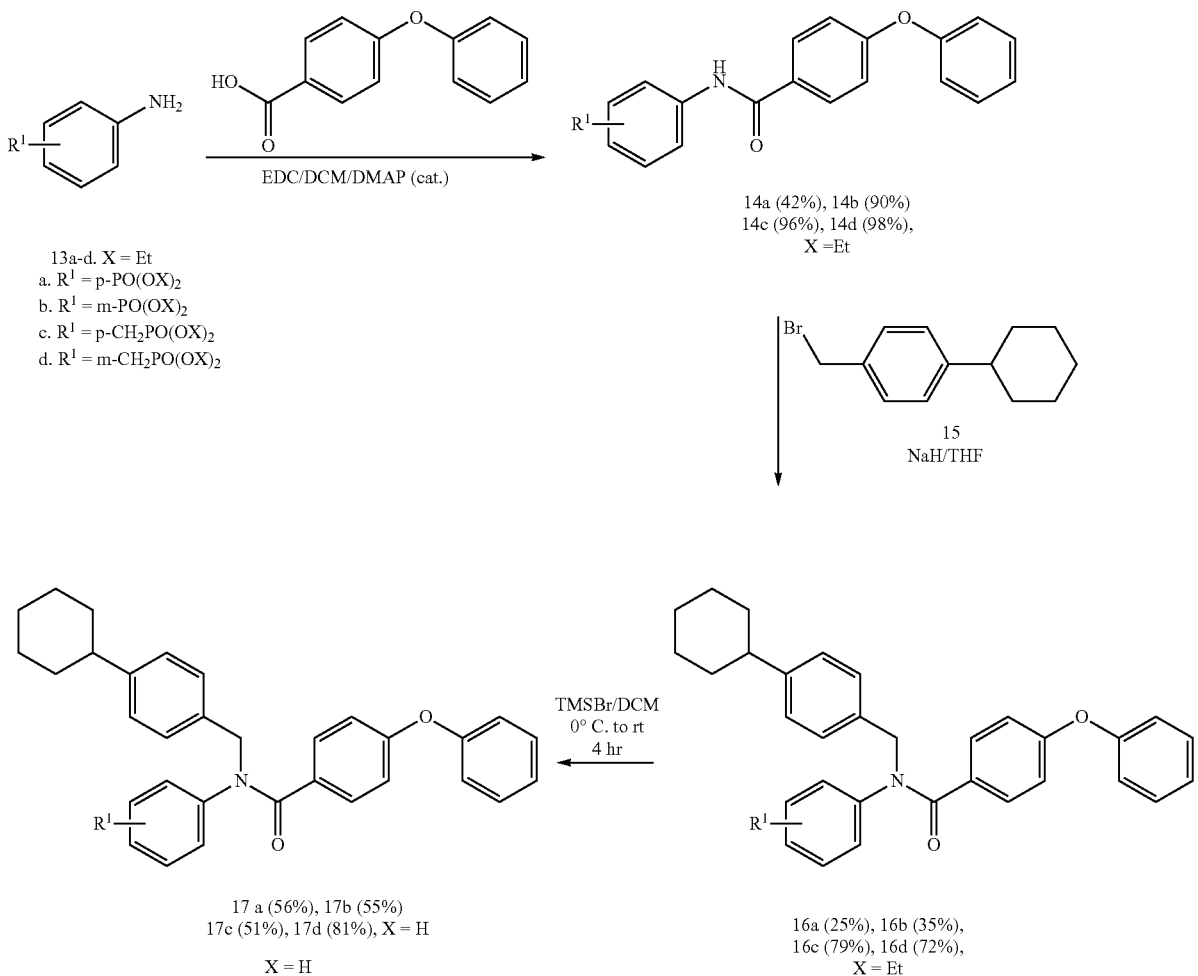
Scheme 2. Synthetic route to phosphonate containing benzamide analogs 17 a-d

17

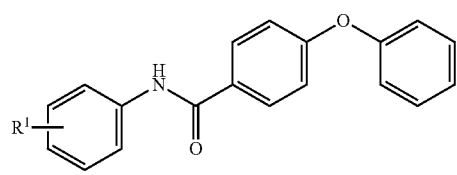

14a-c, X = Et

TMSBr/DCM
0° C. to r.t.

-continued

18

18a (76%), 18b (81%)
18 c (100%), X = H

Scheme 3. Synthetic route to N-benzamide library 20.

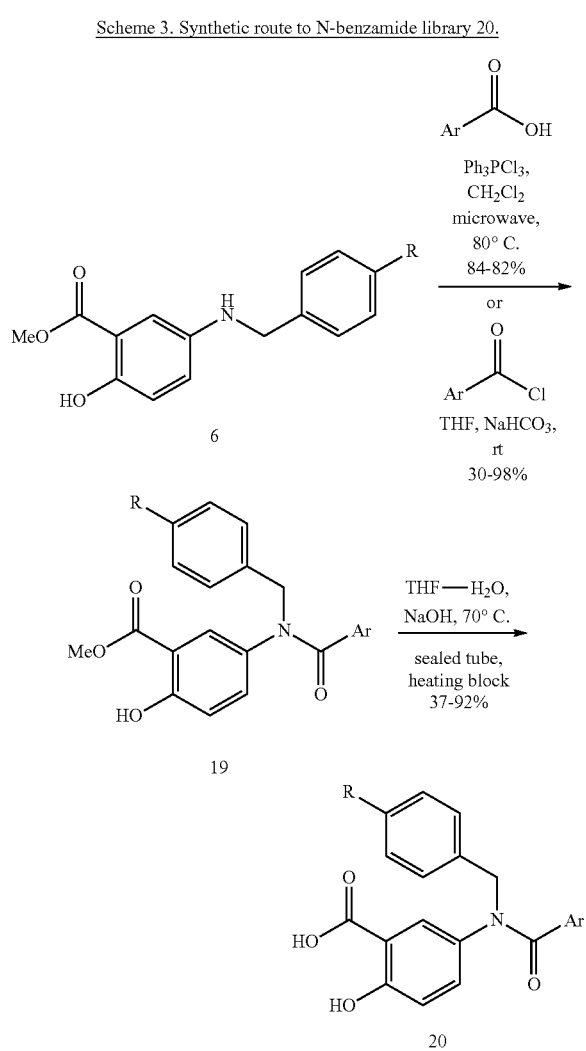

First, the reductive amination of para-substituted arylaldehydes 5 with methyl 5-aminosalicylate (4) provided the corresponding N-arylmethylaminosalicylates 6 in good to excellent yields. The coupling reaction of the series of anilines 6 with N-sulfonylglycine derivatives 7 was conveniently achieved following a modified procedure with dichlorotriphenylphosphorane ($PPh_3Cl_2$) to furnish the tertiary amides 8 in very good yields (Azumaya, et al., *Tetrahedron* 2003; 59:2325-2331). Subsequent hydrolysis of the methyl esters under basic conditions (NaOH-THF—$H_2O$) resulted in the formation of the desired salicylic acids 9. The N-sulfonylglycine derivatives 7 were prepared from either N-benzyl or N-methyl glycine (10 and 11 respectively) via N-sulfonylation with a range of substituted arylsulfonyl chlorides to first provide the sulfonamides 12 which were then hydrolyzed.

A library of related N-benzamides lacking the potentially reactive methylenoxysulfonyl group of 1, incorporating an arylphosphonate (examples 17a and 17b) or benzylphosphonate (examples 17c and 17d) as a phosphotyrosine mimetic, (Burke, et al., *Biochemistry* 1994; 33:6490-4) was prepared as shown in Scheme 2. The amino diethyl phosphonate esters 13a,b,d were prepared by similar methods, whilst phosphonate 13c was commercially available. The phosphonate-containing amides 14a-d were prepared by coupling the amines 13a-d with 4-phenoxybenzoic acid in the presence of EDC and catalytic amount of DMAP in DCM. This was followed by N-alkylation by treatment with sodium hydride and 1-(bromomethyl)-4-cyclohexylbenzene (15) in THF to provide the tertiary amides 16a-d. The final phosphonic acids 17a-d were obtained by treatment of 16a-d with bromotrimethylsilane (TMSBr) (10 eq.) in dichloromethane. Similarly hydrolysis of the intermediate amides 14a-c provided the phosphonic acid-containing amides 18a-c. The library of N-benzamides 20 in which the phosphonic acid of 17 is replaced by a salicylic acid was prepared as shown in Scheme 2.

The amide library 19, incorporating a methyl salicylate, was prepared from the amine library 6 (Scheme 1) via reaction with either a carboxylic acid and dichlorotriphenylphosphorane or directly with an acyl chloride. Finally, hydrolysis of the methyl salicylate ester of library 19, performed in a sealed tube on a heating block, provided the desired library of salicylic acids 20 in good yields.

The ability of the libraries 9, 17 and 20 to inhibit STAT3 dimerization was evaluated by a competitive, fluorescence-polarization (FP)-based assay, as developed by Schust and Berg (Schust, et al., *Chem. Biol.* 2006; 13:1235-1242; Schust, et al., *Anal. Biochem.* 2004; 330:114-118) using full length STAT3 (N-terminal GST, SignalChem, Richmond, BC, Canada) and the fluorescent probe peptide 5-FAM-G (pTyr)LPQTV-$CONH_2$ (GenScript, Piscataway, N.J., USA) (Id.). This peptide, derived from the gp130 IL6 receptor binds to the STAT3 SH2 domain; blocking its binding provides a measure of inhibition of STAT3 dimerization which binds through the sequence (pTyr)LKTKF (Ren, et al., *Bioorg. Med. Chem. Lett.* 2003:13:633-636).

Table 1 shows the STAT3 inhibitory activities of the library of sulfonamides 9 bearing a 5-amido-2-hydroxybenzoic acid group. Compound 9a, which bears a tosyl group, equivalent to the sulfonyl B-ring of S3I-201, and a benzyl group on each nitrogen atom, is weakly active (9a, $IC_{50}=201.3\pm1.5$ μM). When the tosyl group was replaced with a biphenylsulfonyl group, a 9-fold increase in the activity was observed (9b, $IC_{50}=22\pm9.1$ μM). Although, the biphenylsulfonyl group appeared to be superior to the tosyl group, both series were prepared to further explore SAR relationship among these analogs. The para-chlorobenzyl derivative 9c is 4-fold more potent (IC$_{50}$=50±3.8 μM) than the unsubstituted analog 9a (IC$_{50}$=201.3±1.5 μM). Consistent with the above observations, the biphenylsulfonyl derivate (9d, IC$_{50}$=15±1.2 μM) showed better activity than its tosyl analog 9c. Other groups such methoxy, cyclohexyl, n-heptyl, and iso-butyl groups at the para-position of the amido N-benzylated derivatives (9f, 9g, 9h and 9i respectively) resulted in activities similar to that of 9b and 9d (IC$_{50}$ values 17-23 μM). The effect of a methyl group as the R$^1$ group was next assessed. Thus the library of N-methylsulfonamides 9j-s was prepared as shown in Scheme 1 from commercially available sarcosine methyl ester (11). In most cases the N-methylsulfonamides, are less active than the corresponding N-benzylsulfonamide (R$^1$=Bn) counterparts. For example the methyl group in the biphenylsulfonyl example 9k (IC$_{50}$=57±13_M) and 91 (IC$_{50}$=61±6 μM), reduces activity compared to their respective benzyl analog 9b (IC$_{50}$=22±9.1 μM) and 9d (IC$_{50}$=15±1.2 μM). The presence of an alkyl benzyl group (R=cyclohexyl and n-heptyl, Table 1) in the N-methyl sulfonamides 9n (IC$_{50}$=32±12 μM) and 90 (IC$_{50}$=22±8 μM) did not alter their inhibitory as compared to the corresponding N-benzyl sulfonamides 9g (IC$_{50}$=23.3±2 μM) and 9h (IC$_{50}$=19±3.5 μM). Indeed the presence of the cyclohexyl group dramatically improves the activity of the equivalent in tosylsulfonamide 9m (IC$_{50}$=45±12 μM) (cf. unsubstituted benzyl derivative 9j, (IC$_{50}$>1000 μM). A chloro or fluoro biphenylsulfonamide group of the molecule (Ar) was tolerated (compounds 9p-9s) showing similar activities to their biphenylsulfonamide where made. A small number of heterocyclic containing (as the R substituent) analogs 9t-9x were prepared to reduce the overall lipophilicity of the compounds and provide a basic site for salt formation. The sulfonamides 9x (IC$_{50}$=35.3±12.7 μM) and 9u (IC$_{50}$=33.5±1.8 μM) possessing an Nbenzylamide bearing a meta-4-pyridyl group had moderate inhibitory activity. The N-benzylamides 9t (IC$_{50}$>300 μM), 9v (IC$_{50}$=94.7±0.32 μM) and 9w (14.4% inhibition at 50 μM) with heterocycles in the para position were significantly less active.

The size of the glycine linker of 1 was reduced to separate the two aryl groups by 2 atoms by using a simple amide group as shown in 3 (FIG. 1). The N-benzamides 17a and 17b, which incorporate an arylphosphonic acid as their non-hydrolyzable phosphotyrosine mimic, were made as shown in Scheme 2. The para-substituted isomer 17a (IC$_{50}$=42.0±0.8 μM) was moderately active and better than the meta isomer 17b (18% inhibition at 50 μM) (Table 2). The two benzylphosphonic acids 17c (IC$_{50}$=28.4±2.9 μM) and 17d (IC$_{50}$=18.9±1.1 μM) showed improved activity compared to 17a. The N-p-cyclohexylbenzyl group clearly contributes to the activity of 17a,c,d since the unsubstituted amides 18a-c are all significantly less active. The STAT3 inhibitory activity of 17d indicated that the benzamide scaffold merited further attention. Since the phosphonates likely require a prodrug protection strategy to render them cell permeable, salicylic acid containing N-benzamides 20 were prepared. The analog of 17d with a simple unsubstituted N-benzyl substitutent was inactive (Table 3, 20a, 3% inhibition at 50 μM). The 4-methoxybenzyl derivative 20b was weakly active (IC$_{50}$ 118.1±8.6 μM) as was its 3,4-dimethoxy analog 20c. Some improvement in activity was observed when the R substituent was a halogen (20d, IC$_{50}$ 48±9.4 μM and 20e, IC$_{50}$ 52±4.3 μM). The presence of an alkyl group (R=n-heptyl and cyclohexyl, Table 3) resulted in further improvement (20f, IC$_{50}$ 12.8±0.5 μM and 20g, IC$_{50}$ 15±4.4 μM respectively). This effect of the para-alkyl group of the N benzylamide of 9g-i also resulted in analogs with similar activities (Table 1). Replacement of the phenoxybenzoyl group of 20f (IC$_{50}$ 12.8±0.5 μM) by benzoyl (20h, IC$_{50}$ 32±4 μM) and 3-methoxybenzoyl (20i, IC$_{50}$ 33.3±1.6 μM) resulted in a two-fold reduction in activity in both cases. Substitution of the phenyl group of 20h by a pyridyl group as in 20j, 20k and 201 resulted in significant reduction in activity.

TABLE 1

In vitro STAT3 dimerization inhibitory activity of library 9

9

| Compound | R | R$^1$ | Ar | IC$_{50}$ (μM) |
|---|---|---|---|---|
| 9a | H | Bn | 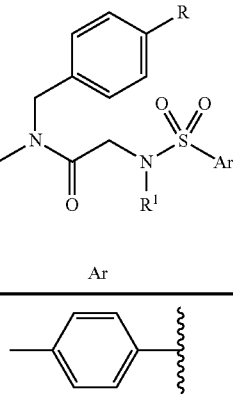 | 201.3 ± 1.5 |
| 9b | H | Bn | 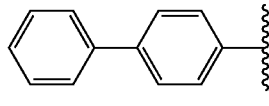 | 22.2 ± 9.1 |
| 9c | Cl | Bn | 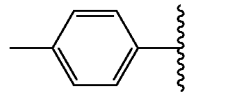 | 50 ± 3.8 |

TABLE 1-continued

In vitro STAT3 dimerization inhibitory activity of library 9

| Compound | R | R¹ | Ar | IC$_{50}$ (μM) |
|---|---|---|---|---|
| 9d | Cl | Bn | biphenyl | 15 ± 1.2 |
| 9f | OCH$_3$ | Bn | biphenyl | 22 ± 10 |
| 9g | cyclohexyl | Bn | biphenyl | 23.3 ± 2 |
| 9h | n-C$_7$H$_{13}$ | Bn | biphenyl | 19 ± 3.5 |
| 9i | iso-Butyl | Bn | biphenyl | 17 ± 3.6 |
| 9j | H | Me | 4-methylphenyl | >1000 |
| 9k | H | Me | biphenyl | 57 ± 13 |
| 9l | Cl | Me | biphenyl | 61 ± 6 |
| 9m | cyclohexyl | Me | 4-methylphenyl | 45 ± 12 |
| 9n | cyclohexyl | Me | biphenyl | 32 ± 12 |
| 9o | n-C$_7$H$_{13}$ | Me | biphenyl | 22 ± 8 |

TABLE 1-continued
In vitro STAT3 dimerization inhibitory activity of library 9
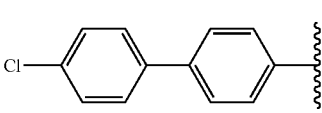
| Compound | R | R¹ | Ar | IC$_{50}$ (μM) |
|---|---|---|---|---|
| 9p | iso-Butyl | Me | 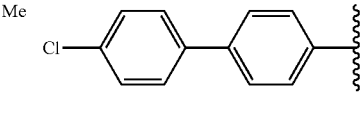 | 20 ± 7.1 |
| 9q | Cl | Me | 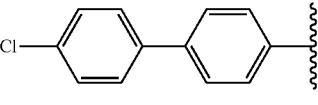 | 43 ± 6 |
| 9r | OCH$_3$ | Me | 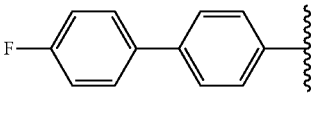 [SMILES: *c1ccc(-c2ccc(F)cc2)cc1] | 50 ± 9.1 |
| 9s | n-C$_7$H$_{13}$ | Me | 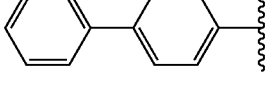 | 23 ± 0.3 |
| 9t | 4-Piperidyl | Bn | 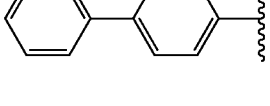 | >300 |
| 9u | 3-(4-Pyridyl) | Bn | 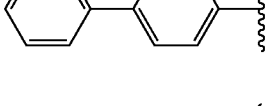 | 33.5 ± 1.8 |
| 9v | 4-Morpholinyl | Bn | 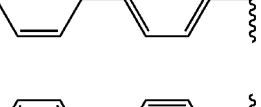 | 94.7 ± 0.32 |
| 9w | 4-Piperidyl | Me | 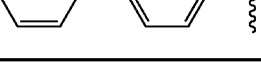 | 14.4 ± 0.6% inhibition at 50 μM |
| 9x | 3-(4-Pyridyl) | Me | 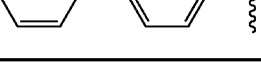 | 35.3 ± 12.7 |

TABLE 2

In vitro STAT3 dimerization inhibitory activity phosphonate library 17.

| Compound | Structure | IC$_{50}$ (μM) |
| --- | --- | --- |
| 17a | 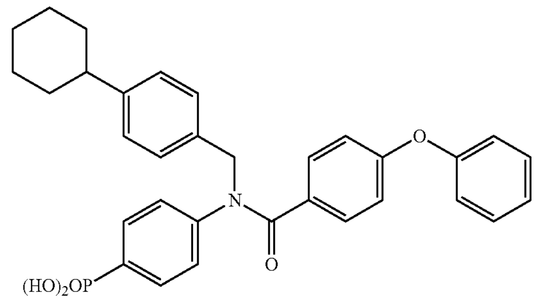 | 42.0 ± 0.8 |
| 17b | 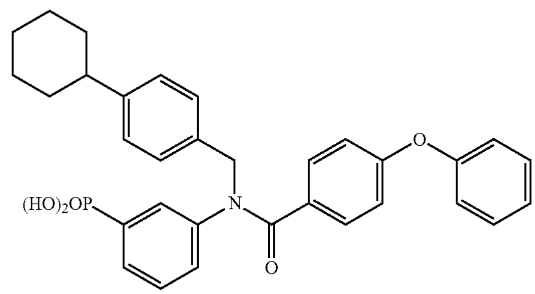 | 17.9 ± 0.5% inhibition at 50 μM |
| 17c | 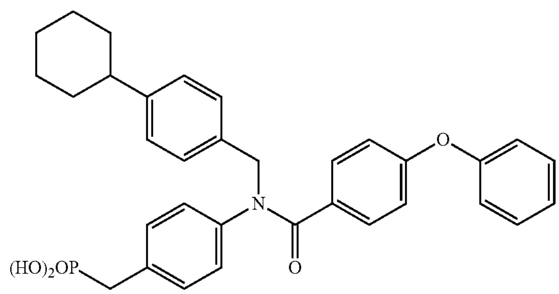 | 28.4 ± 2.9 |
| 17d | 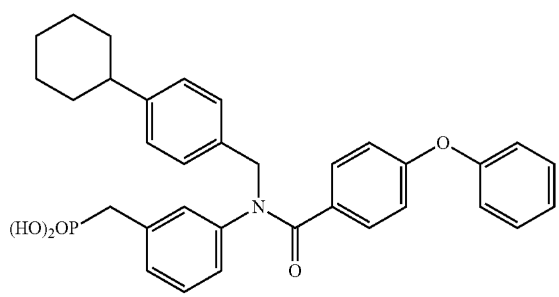 | 18.9 ± 1.1 |
| 18a | 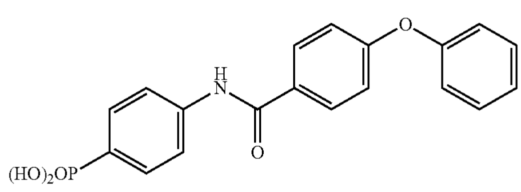 | 7.0 ± 2.9% inhibition at 50 μM |
| 18b | 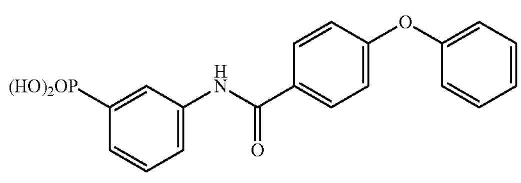 | 9.0 ± 1.7% inhibition at 50 μM |

TABLE 2-continued

In vitro STAT3 dimerization inhibitory activity phosphonate library 17.

| Compound | Structure | IC$_{50}$ (μM) |
|---|---|---|
| 18c | (HO)$_2$OP-CH$_2$-C$_6$H$_4$-NH-C(O)-C$_6$H$_4$-O-C$_6$H$_5$ | 32.8 ± 6.3% inhibition at 50 μM |

TABLE 3

In vitro STAT3 dimerization inhibitory activity of library 20.

20

| Compound | R | Ar | IC$_{50}$ (μM) unless otherwise specified |
|---|---|---|---|
| 20a | H | 4-phenoxyphenyl | 3% inhibition at 50 μM |
| 20b | OMe | 4-phenoxyphenyl | 118.1 ± 8.6 |
| 20c | 3,4-Di-OMe[a] | 4-phenoxyphenyl | 13 ± 8% inhibition at 50 μM |
| 20d | Cl | 4-phenoxyphenyl | 48 ± 9.4 |
| 20e | Br | 4-phenoxyphenyl | 52 ± 4.3 |

TABLE 3-continued

In vitro STAT3 dimerization inhibitory activity of library 20.

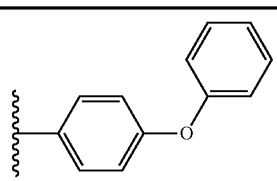

| Compound | R | Ar | IC$_{50}$ (μM) unless otherwise specified |
|---|---|---|---|
| 20f | Heptyl | 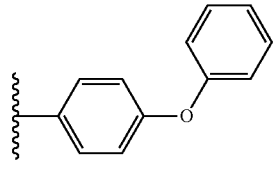 [SMILES: *c1ccc(Oc2ccccc2)cc1] | 12.8 ± 0.5 |
| 20g | Cyclohexyl | 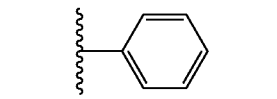 [SMILES: *c1ccccc1] | 15 ± 4.4 |
| 20h | Heptyl | 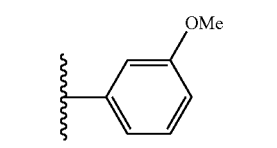 [SMILES: *c1cccc(OC)c1] | 32 ± 4 |
| 20i | Heptyl | 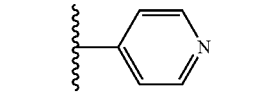 | 33.3 ± 1.6 |
| 20j | Heptyl | 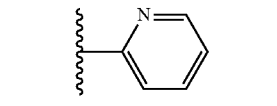 [SMILES: *c1ccccn1] | 22 ± 5% inhibition at 50 μM |
| 20k | Heptyl | 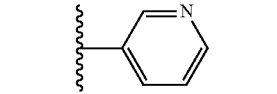 [SMILES: *c1cccnc1] | 21 ± 3% inhibition at 50 μM |
| 20l | Heptyl | | 31 ± 6% inhibition at 50 μM |

$^a$indicates 3,4-distribution of the phenyl group bearing the R substituent.

Figure 2C:
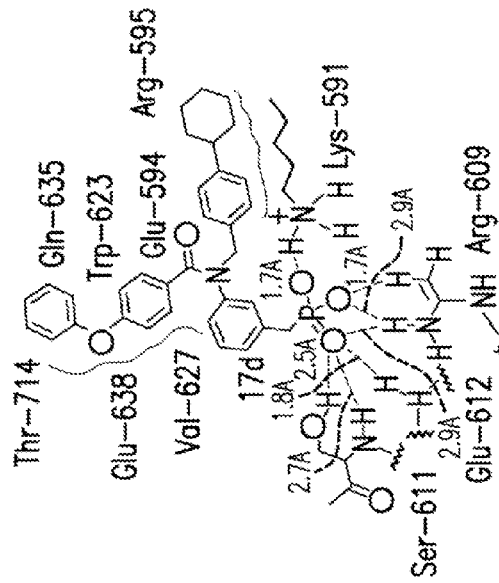
FIG. 2 shows the docking of phosphonic acid 17d and salicylic acids 20f and 20g to the STAT3 SH2 domain. a: is an overlay of the docked poses of phosphonate 17d and salicylic acids 20f and 20g with hydrogen atoms omitted. b: is a surface rendering of 17d docked to the STAT3 p-Tyr binding site. c: is a schematic binding mode of 17d to the STAT3 SH2 domain showing the hydrogen bonds and hydrophobic interactions.
Figure 2B:
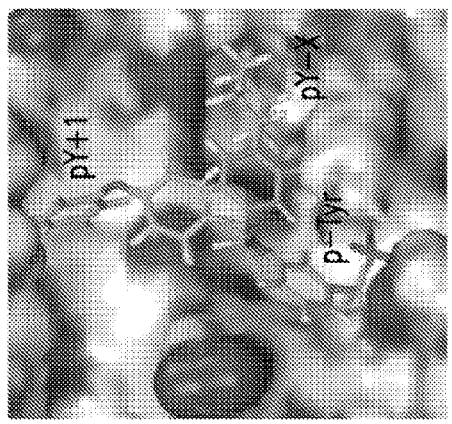
Figure 3:
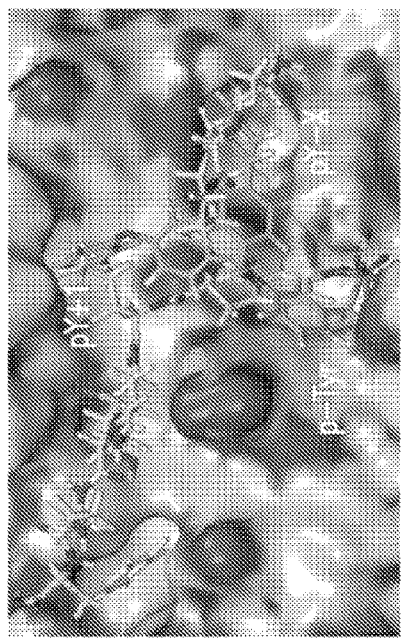
FIG. 3 is a surface rendering of phosphonic acid 17d docked to the STAT3 p-Tyr binding site overlaid with the STAT3 peptide (X-ray).
Figure 2A:
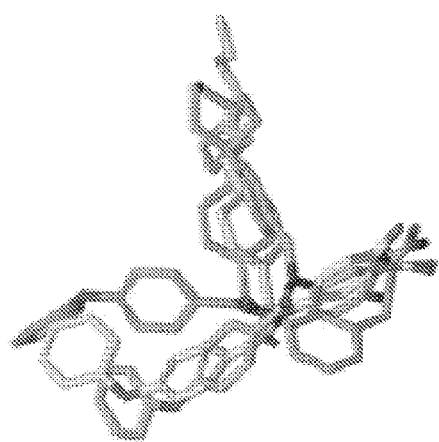

The phosphonic acid 17d, and salicylic acids 20f and 20g were docked to the STAT3 SH2 using GLIDE. The low-energy docking poses are shown in FIG. 2 position the acidic groups in the pTyr-705 binding site and are broadly similar. The superimposition of all three inhibitors 17d, 20f, and 20g is shown in FIG. 2a. The meta-phosphonic acid group of 17d occupies the phenylphosphate binding pocket (FIG. 2b). Indeed, the phosphorus atom is only 0.2 Å from the position of the STAT3 pTyr-705 residue X-ray coordinates (see FIG. 3). Hydrogen bonds are formed between the three phosphate oxygen atoms and with residues Lys-591, Arg-609, Glu-612 and Ser-611 (FIG. 2c). Charged interactions are evident between the phosphonate and the Lys-591 and Arg-609 residues. The phenoxybenzoyl group is positioned with the terminal phenyl group occupying the pY+1 hydrophobic pocket. The p-cyclohexylbenzyl group places the cyclohexyl group deep within the hydrophobic pY-X pocket. (Park, et al., *J. Mol. Recognit.* 2011; 24:254-265). The salicylic acids 20f and 20g dock with their hydroxycarboxylic acid groups deep within the p-Tyr binding site. The docking pose of 20g positions its p-cyclohexylbenzyl group in the pY-X pocket and the phenoxyphenyl group in a region close to the pY+1 pocket. A similar pose is also obtained for salicylic acid 20f (shown in FIG. 2a) with the p-heptylbenzyl group occupying the pY-X pocket. The terminal phenyl group of the phenoxybenzoyl group is located in the pY+1 pocket (see FIG. 4a). Overall the docking shows that all three molecules are able to adopt reasonable conformations that results in polar interactions of the acid group with the p-Tyr binding pocket and hydrophobic interaction of each of the sides chains in both the pY-X pocket and the area close to or in pY+1 pocket.

It demonstrated herein that the phosphotyrosine mimicking 5-amino-2-hydroxybenzoic acid can be incorporated into analogs of 1 and provide significantly active STAT3 dimerization inhibitors. A series of N-benzylbenzamides 20 were prepared by removing the reactive sulfonyloxymethyl moiety of the linking group of 1, as STAT3 dimerization inhibitors with improved potency. The equivalent potencies of 20g and 17d further validates 5-amino-2-hydroxybenzoic acid as a phosphotyrosine mimic. 20g inhibits STAT3 dimerization in vitro and in intact cells and suppresses malignant transformation in human cancer cells that depend on STAT3.

It is also demonstrated herein that S3I-1757 (also referred to herein as 20g) inhibits STAT3 dimerization in vitro and in whole cells, STAT3 tyrosine phosphorylation, nuclear accumulation, transcriptional activity and expression of STAT3-regulated genes as well as anchorage-dependent and -independent growth, migration and invasion. The ability of S3I-1757 to displace fluorescein-GpYLPQTV in the FP assay in vitro indicates that S3I-1757 binds the SH2 domain of STAT3 at the phospho-tyrosine-705 binding site. Molecular modeling studies give further support to this mechanism. Molecular modeling indicates that S3I-1757 makes several contacts with Arg-609 and Lys-591, 2 critical amino acids in the SH2 domain that are known to bind phospho-Tyr-705 of PpYLKTK of STAT3 as well as phospho-Tyr-904 of GpYLPQTV of the gp-130 subunit of the IL-6 receptor. In whole cells, S3I-1757 disrupted the binding of HA-STAT3 to FLAG-STAT3 as demonstrated both by co-immunoprecipitation and co-localization, consistent with the in vitro FP and molecular modeling results. Taken together, these results indicate that S3I-1757 is a STAT3-STAT3 dimerization inhibitor. The other analogs of S3I-1757 disclosed herein are expected to have similar activities.

Furthermore, STAT3 is also known to associate with the EGF receptor (EGFR) through binding of the STAT3-SH2 domain to phospho-tyrosines 1068 and 1086 on EGFR, and S3I-1757 inhibited the binding of STAT3 to EGFR. S3I-1757 also inhibited STAT3 tyrosine phosphorylation. This indicates that the ability of S3I-1757 to inhibit nuclear translocation, DNA binding and transcriptional activation can be due to its ability to directly disrupt STAT3-STAT3 dimerization as well as inhibition of STAT3-EGFR binding and subsequent suppression of STAT3 tyrosine phosphorylation which would also lead to preventing STAT3 dimerization. The fact that STAT3-C, a genetically engineered mutant of STAT3 that forms a constitutively dimerized STAT3 through disulfide bonds in the absence of tyrosine phosphorylation, was able to rescue from S3I-1757 inhibition of transcriptional activity further solidifies the suggestion that S3I-1757 is a STAT3 dimerization inhibitor.

S3I-1757 inhibited anchorage-dependent proliferation/ survival and colony formation as well as anchorage-independent soft agar growth, migration and invasion, consistent with its ability to suppress the expression of genes that are known to drive these hallmarks of cancer such as cyclin D1, Bcl xL, survivin, and MMP9. The fact that S3I-1757 did not inhibit other signal transduction pathways such as those leading to hyper-activated P-Akt and P-Erk suggest that S3I-1757 induces these effects through inhibition of STAT3. Further support for this suggestion comes from the fact that S3I-1757 inhibited anchorage-dependent and -independent tumor cell growth, migration and invasion selectively in human cancer cells that dependent on STAT3 over those that do not. S3I-1756, a closely related structural analogue of S3I-1757 that does not inhibit STAT3-STAT3 dimerization, STAT3 tyrosine phosphorylation, DNA binding and transcriptional activation, was not able to inhibit anchorage dependent and -independent tumor cell growth, migration and invasion. The fact that STAT3-C, was able to rescue from S3I-1757 induction of apoptosis and inhibition of gene expression, tumor cell growth, migration and invasion strongly supports the suggestion that S3I-1757 mediates its effects through inhibition of STAT3.

Methods of Use

Further provided herein are methods of treating or preventing cancer in a subject, comprising administering to the subject a therapeutically effective amount of a compound or composition as disclosed herein. Additionally, the method can further comprise administering a therapeutically effective amount of ionizing radiation to the subject. The disclosed compounds and compositions are suitable for cancers where STAT3 is persistently tyrosine phosphorylated and constitutively activated in the cancer, such as, but not limited to, pancreatic cancer, breast cancer, lung cancer, prostrate cancer, ovarian cancer, colon cancer, gastric cancer, head and neck cancer, melanoma, leukemia, multiple myeloma or lypmpoma Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrôm's macroglobulinemia, and Wilms' tumor.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E.W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. the liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

The disclosed subject matter also concerns a packaged dosage formulation comprising in one or more containers at least one inhibitor compound or composition disclosed herein. A packaged dosage formulation can optionally comprise in one or more containers a pharmaceutically acceptable carrier or diluent. A packaged dosage formulation can also optionally comprise, in addition to an inhibitor compound or composition disclosed herein, other STAT3 inhibitors.

Depending upon the disorder or disease condition to be treated, a suitable dose(s) can be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All reagents were purchased from commercial suppliers and used without further purification. Melting points were determined using a Barnstead international melting point apparatus and remain uncorrected. Proton NMR spectra were recorded on an Agilent-Varian Mercury 400 MHz spectrometer with $CDCl_3$ or $DMSO-d_6$ as the solvent. Carbon ($^{13}C$) NMR spectra are recorded at 100 MHz. The $^{13}C$ spectrum of 1 was recorded at 150 MHz, using an Agilent VNMRS 600 spectrometer with cold probe (University of South Florida Center for Drug Discovery and Innovation). All coupling constants are measured in Hertz (Hz) and the chemical shifts ($\delta_H$ and $\delta_c$) are quoted in parts per million (ppm) relative to TMS ($\delta$ 0), which was used as the internal standard. High resolution mass spectroscopy was carried out on an Agilent 6210 LC/MS (ESI–TOF). Low resolution mass spectroscopy (LRMS) was performed on an Agilent single quad G1956A (Chemistry Department, University of South Florida). Microwave reactions were performed in CEM 908005 model and Biotage initiator 8 machines. All final compounds were purified to ≥95% purity as determined HPLC analysis using a JASCO HPLC system equipped with a PU-2089 Plus quaternary gradient pump and a UV-2075 Plus UV-VIS detector, using an Alltech Kromasil C-18 column (150×4.6 mm, 5 µm) and Agilent Eclipse XDB-C18 (150×4.6 mm, 5 µm). Melting points were recorded on an Optimelt automated melting point system (Stanford Research Systems). Thin layer chromatography was performed using silica gel 60 F254 plates (Fisher), with observation under UV when necessary Anhydrous solvents (acetonitrile, dimethylformamide, ethanol, isopropanol, methanol and tetrahydrofuran) were used as purchased from Aldrich. Burdick and Jackson HPLC grade solvents (methanol, acetonitrile and water) were purchased from VWR for HPLC and high resolution mass analysis. HPLC grade TFA was purchased from Fisher.

Human breast cancer (MDA-MB-468, MDA-MB-231, MDA-MB-453), lung cancer (A549, H358, H460) cells, human non-tumorigenic epithelial cells (MCF10A) and human embryonic kidney cells (HEK293) were obtained from ATCC (the American Type Culture Collection, Manassas, Va., USA). HEK 293 cell lines with stable transfection of HA-STAT3 and FLAG-STAT3 were generated as described below. Cells were grown in Dulbecco's modified Eagle's medium (DMEM), RPMI 1640, and DMEM/F-12 containing 10% heat-inactivated fetal bovine serum. MCF10A was cultured in DMEM/F12, supplemented with 5% horse serum (Invitrogen, CA, USA), hydrocortisone (0.5 µg/ml), mouse epidermal growth factor (EGF; 20 ng/ml), insulin (10 µg/ml), cholera toxin (100 ng/ml, Sigma, MO, USA). Primary antibodies against pY705STAT3, pAKT, AKT, pErk½, Erk, MMP9, and Cyclin D1 were purchased from Cell Signaling Technology (Danvers, Mass.). Primary antibodies against STAT3, Bcl-xL, Survivin, HA (anti-mouse), and HA (anti-rabbit) were purchased from Santa Cruz Biotech (Santa Cruz, Calif.). Primary antibody against FLAG was purchased from Sigma (St. Louis, Mo., USA).

Synthesis of benzylaminosalicylates 6

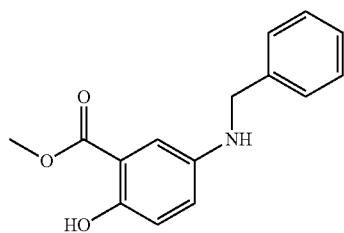 [SMILES: COC(=O)c1cc(NCc2ccccc2)ccc1O]

Methyl 5-(benzylamino)-2-hydroxybenzoate (6a). To a stirred solution of methyl 5-aminosalicylate (4) (0.200 g, 1.196 mmol) in MeOH (10 ml) over 4 Å molecular sieves was added benzaldehyde (0.121 mL, 1.196 mmol) followed by AcOH (0.106 mL). The solution was heated at 40° C. and then allowed to stir at room temperature for 1 h. The solution was cooled to 5-10° C. and NaCNBH$_3$ (0.097 g, 1.554 mmol) was slowly added in portions. The resulted mixture was stirred for 2 h at room temperature before being quenched by the addition of water. The solvents were evaporated and the crude mixture was taken up in CH$_2$Cl$_2$, washed with water, brine, dried (Na$_2$SO$_4$) and evaporated. Chromatography gave the ester 6a (0.268 g, 1.042 mmol, 87%). $^1$H NMR (400 MHz, CDCl$_3$) δ 10.18 (s, 1H), 7.38-7.26 (m, 5H), 7.08 (t, J=1.7 Hz, 1H), 6.84 (d, J=1.7 Hz, 2H), 4.27 (s, 2H), 3.91 (s, 3H). HRMS (ESI-ve) Calcd for C$_{15}$H$_{16}$NO$_3$ 258.1124 [M+H]$^+$, found 258.1127.

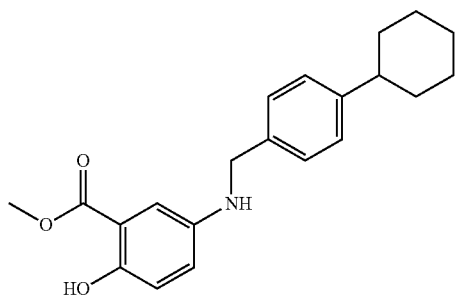 [SMILES: COC(=O)c1cc(NCc2ccc(C3CCCCC3)cc2)ccc1O]

Methyl 5-(4-cyclohexylbenzylamino)-2-hydroxybenzoate (6b). This was obtained as a yellow oil (0.246 g, 0.78 mmol, 35%) from methyl 5-aminosalicylate (4) (0.411 g, 2.465 mmol) and 4-cyclohexylbenzaldehyde (0.464 g, 2.465 mmol) in the same manner as described for 6a. $^1$H NMR (400 MHz, CDCl$_3$) δ 10.19 (s, 1H), 7.29 (d, J=8.2 Hz, 2H), 7.19 (d, J=8.0 Hz, 2H), 7.10 (t, J=1.7 Hz, 1H), 6.85 (d, J=1.7 Hz, 2H), 4.23 (s, 2H), 2.52-2.45 (m, J 1H), 1.9-1.68 (m, 5H), 1.50-1.14 (m, 5H). HRMS (ESI-ve) Calcd for C$_{21}$H$_{26}$N$_2$O$_3$ 340.1907 [M+H]$^+$, found 340.1911.

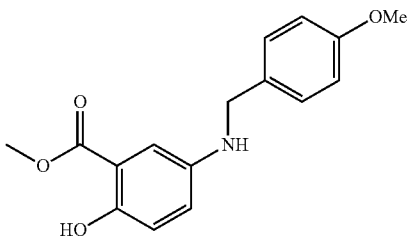 [SMILES: COC(=O)c1cc(NCc2ccc(OC)cc2)ccc1O]

Methyl 2-hydroxy-5-(4-methoxybenzylamino)benzoate (6c). This was obtained as a solid from methyl 5-aminosalicylate (4) (1.00 g, 5.98 mmol) and 4-methoxybenzaldehyde (0.726 mL, 5.98 mmol) in the same manner as described for 6a. $^1$H NMR (400 MHz, CDCl$_3$) δ 10.99 (s, 1H), 7.59 (d, J=9.3 Hz, 1H), 7.25 (d, J=8.8 Hz, 2H), 6.88 (d, J=8.7 Hz, 2H), 6.15-6.08 (m, 2H), 4.43 (t, J=4.5 Hz, 1H), 4.28 (d, J=5.3 Hz, 2H), 3.87 (s, 3H), 3.81 (s, 3H). HRMS (ESI-ve) Calcd for C$_{16}$H$_{17}$NNaO$_4$ 310.1049 [M+Na]$^+$, found 310.1048.

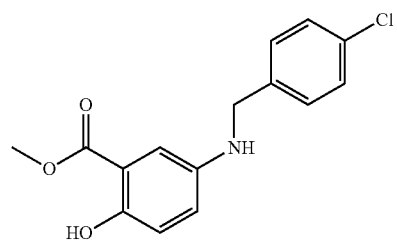 [SMILES: COC(=O)c1cc(NCc2ccc(Cl)cc2)ccc1O]

Methyl 5-(4-chlorobenzylamino)-2-hydroxybenzoate (6d). This was obtained as a solid from methyl 5-aminosalicylate (4) (1.00 g, 5.98 mmol) and 4-chlorobenzaldehyde (0.840 g, 5.98 mmol) in the same manner as described for 6a. $^1$H NMR (400 MHz, CDCl$_3$) δ 10.98 (s, 2H), 7.60 (d, J=8.7 Hz, 1H), 7.31 (d, J=8.4 Hz, 2H), 7.26 (d, J=8.8 Hz, 2H), 6.11 (dd, J=8.7, 2.3 Hz, 1H), 6.07 (d, J=2.3 Hz, 1H), 4.53 (s, 1H), 4.34 (d, J=5.0 Hz, 2H), 3.87 (s, 3H). HRMS (ESI-ve) Calcd for C$_{15}$H$_{15}$NClO$_3$ 292.0735 [M+H]$^+$, found 292.0727.

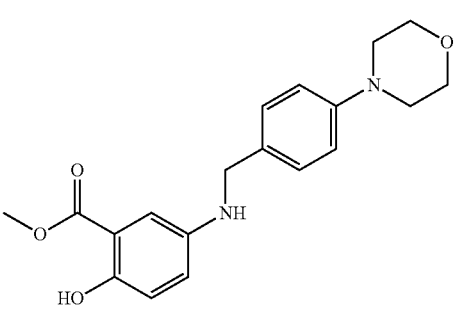 [SMILES: COC(=O)c1cc(NCc2ccc(N3CCOCC3)cc2)ccc1O]

Methyl 2-hydroxy-5-(4-morpholinobenzylamino)benzoate (6e). This was obtained as a solid (0.960 g, 80%) from methyl 5-aminosalicylate (4) and 4-morpholinobenzaldehyde in the same manner as described for 6a. $^1$H NMR (400 MHz, CDCl$_3$) δ 10.19 (s, 1H), 7.27 (d, J=8.7 Hz, 2H), 7.08 (t, J=1.6 Hz, 1H), 6.89 (d, J=8.7 Hz, 1H), 6.84 (d, J=1.6 Hz, 2H), 4.18 (s, 2H), 3.92 (s, 3H), 3.88-3.84 (m, 4H), 3.19-3.09 (m, 4H). HRMS (ESI-ve) Calcd for C$_{19}$H$_{22}$N$_2$NaO$_4$ 365.1471 [M+Na]$^+$, found 365.1471.

Methyl 2-hydroxy-5-(4-(piperidin-1-yl)benzylamino)benzoate (6h). This was obtained as a solid (0.800 g, 80%) from methyl 5-aminosalicylate (4) (0.500 g, 2.99 mmol) and 4-(piperidin-1-yl)benzaldehyde (0.566 g, 2.99 mmol) in the same manner as described for 6a. $^1$H NMR (400 MHz, CDCl$_3$) δ 10.19 (s, 1H), 7.23 (d, J=8.7 Hz, 2H), 7.08 (t, J=1.7 Hz, 1H), 6.91 (d, J=8.7 Hz, 2H), 6.84 (d, J=1.7 Hz, 2H), 4.16 (s, 2H), 3.92 (s, 3H), 3.28-2.96 (m, 4H), 1.75-1.44 (m, 6H). HRMS (ESI-ve) Calcd for C$_{20}$H$_{25}$N$_2$O$_3$ 341.1859 [M+H]$^+$, found 341.1865.

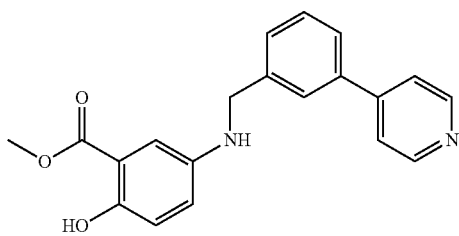 [SMILES: COC(=O)c1cc(NCc2cccc(-c3ccncc3)c2)ccc1O]

Methyl 2-hydroxy-5-(3-(pyridin-4-yl)benzylamino)benzoate (6f). This was obtained as a solid from methyl 5-aminosalicylate (4) (0.500 g, 2.99 mmol) and 3-(pyridin-4-yl)benzaldehyde (0.547 g, 2.99 mmol) in the same manner as described for 6a. $^1$H NMR (400 MHz, CDCl$_3$) δ 10.19 (s, 1H), 8.65 (d, J=6.1 Hz, 1H), 7.65 (s, 1H), 7.56 (dt, J=7.0, 1.9 Hz, 1H), 7.50 (d, J=6.2 Hz, 1H), 7.47-7.43 (m, 2H), 7.12-7.09 (m, 1H), 6.88-6.83 (m, 2H), 4.37 (s, 2H), 3.91 (s, 3H). HRMS (ESI-ve) Calcd for C$_{20}$H$_{19}$N$_2$O$_3$ 335.1390 [M+H]$^+$, found 335.1397.

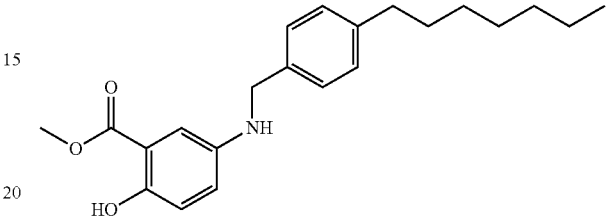

Methyl 5-(4-heptylbenzylamino)-2-hydroxybenzoate (6i). This was obtained as an oil (1.04 g, 96%) from methyl 5-aminosalicylate (4) (0.500 g, 2.99 mmol) and 4-heptylbenzaldehyde (0.611 g, 2.99 mmol) in the same manner as described for 6a and was used without purification. $^1$H NMR (400 MHz, CDCl$_3$) δ 10.19 (s, 1H), 7.28-7.26 (m, 3H), 7.15 (d, J=7.9 Hz, 1H), 7.10-7.09 (m, 1H), 6.85-6.84 (m, 2H), 4.23 (s, 2H), 3.92 (s, 3H), 2.72-2.49 (m, 3H), 1.61-1.60 (m, 3H), 1.42-1.25 (m, 10H), 0.88 (t, J=6.5 Hz, 3H).

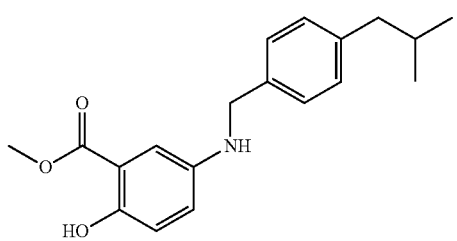 [SMILES: COC(=O)c1cc(NCc2ccc(CC(C)C)cc2)ccc1O]

Methyl 2-hydroxy-5-(4-isobutylbenzylamino)benzoate (6g). This was obtained as an oil (40-45%) from methyl 5-aminosalicylate (4) (0.903 g, 5.41 mmol) and 4-isobutylbenzaldehyde (0.877 g, 5.41 mmol) in the same manner as described for 6a. $^1$H NMR (400 MHz, CDCl$_3$) δ 10.20 (s, 1H), 7.28 (d, J=8.0 Hz, 2H), 7.13 (d, J=8.0 Hz, 2H), 7.10 (t, J=1.7 Hz, 1H), 6.85 (d, J=1.6 Hz, 2H), 4.24 (s, 2H), 3.92 (s, 4H), 2.48 (d, J=7.2 Hz, 2H), 1.92-1.83 (m, 1H), 0.91 (d, J=6.6 Hz, 6H).

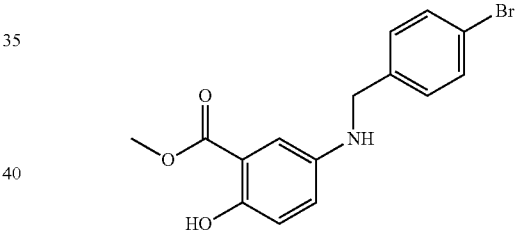

Methyl 5-(4-bromobenzylamino)-2-hydroxybenzoate (6j). This was obtained as a yellow solid (1.9 g, 60%) from methyl 5-aminosalicylate (4)(0.903 g, 5.41 mmol) and 4-cyclohexylbenzaldehyde (1.9 g, 5.41 mmol) in the same manner as described for 6a. $^1$H NMR (400 MHz, CDCl$_3$) δ 10.20 (s, 1H), 7.46 (d, J=8.3 Hz, 2H), 7.24 (d, J=8.2 Hz, 2H), 7.05 (d, J=2.3 Hz, 1H), 6.86-6.82 (m, 2H), 4.24 (s, 2H), 3.91 (s, 3H).

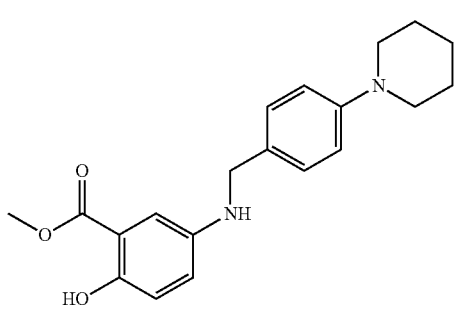 [SMILES: COC(=O)c1cc(NCc2ccc(N3CCCCC3)cc2)ccc1O]

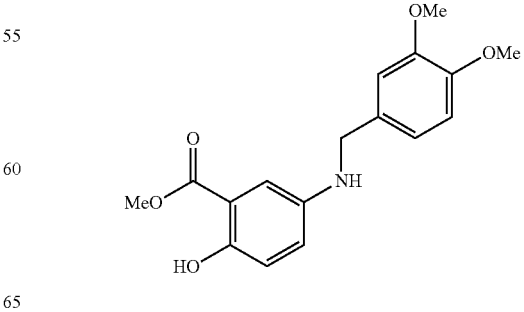

Methyl 5-(3,4-dimethoxybenzylamino)-2-hydroxybenzoate (6k). A solution of 3,4-dimethoxybenzaldehyde (0.546 g, 3.28 mmol), methyl 4-aminosalicylic acid (4)(0.551 g, 3.29 mmol) and Et₃N (0.5 ml) in anhydrous methanol (12 mL), was heated under reflux overnight. The solvent was then removed under reduced pressure. The obtained solid was then suspended in methanol (12 mL) and NaBH₄ (0.239 g, 6.26 mmol) was added portion-wise. The reaction mixture was then stirred at room temperature overnight. The solvent was removed under reduced pressure, water (10 mL) was added and the mixture extracted with EtOAc (2×10 mL). The organic extracts were combined, dried (Na₂SO₄), filtered and the solvent removed under reduced pressure to provide a brown solid. The obtained crude material was slurried with Et₂O (10 mL), filtered and dried under vacuum to yield compound 6k as an orange solid (0.483 g, 1.52 mmol, 46%). ¹H NMR (400 MHz, CDCl₃) δ 10.18 (s, 1H), 7.24 (d, J=3.0 Hz, 1H), 7.08 (s, 1H), 6.89-6.81 (m, 6H), 4.19 (s, 2H), 3.91 (s, 3H), 3.86 (s, 6H). LCMS (ESI+ve) m/z [M+Na]⁺ found 340.1

Synthesis of acids 7

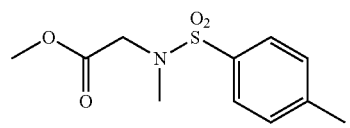

Methyl 2-(N,4-dimethylphenylsulfonamido)acetate (12a). To a stirred solution of N-methylglycine methyl ester (11) (0.500 g, 3.58 mmol) in acetonitrile (15 mL) was added DIPEA (1.87 mL, 10.75 mmol) and TsCl (0.819 g, 4.3 mmol) was added in portions at 0° C. After the addition was complete, the ice bath was removed and the reaction was stirred at room temperature overnight. The solvents were evaporated and the crude mixture was taken up in CH₂Cl₂ and washed with 0.1 N HCl, Sat. NaHCO₃ and brine. The organic layer was dried over Na₂SO₄ and evaporated in vacuo. The product 12a (0.791 g, 86%) was directly carried to the next step without further purification. ¹H NMR (400 MHz, CDCl₃) δ 7.69 (d, J=8.3 Hz, 2H), 7.31 (d, J=8.5 Hz, 2H), 3.96 (s, 2H), 3.66 (s, 3H), 2.87 (s, 3H), 2.42 (s, 3H).

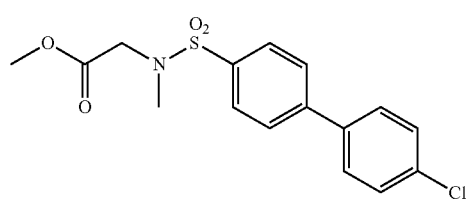 [SMILES: COC(=O)CN(C)S(=O)(=O)c1ccc(-c2ccc(Cl)cc2)cc1]

Methyl 2-(N,4-dimethylphenylsulfonamido)acetate (12b). This was obtained as an oil from N-methylglycine methyl ester (11) (1.5 g, 10.75 mmol) and biphenylsulfonyl chloride (3.269 g, 12.9 mmol) in the same manner as described for 12a. ¹H NMR (400 MHz, CD₃OD) δ 7.87 (d, J=8.6 Hz, 2H), 7.83 (d, J=8.6 Hz, 2H), 7.69 (d, J=8.5 Hz, 2H), 7.49 (d, J=8. Hz, 2H), 4.04 (s, 2H), 3.64 (s, 3H), 2.90 (s, 3H).

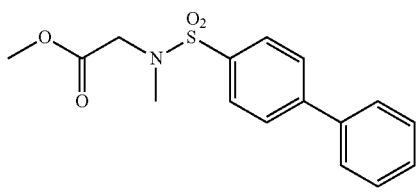 [SMILES: COC(=O)CN(C)S(=O)(=O)c1ccc(-c2ccccc2)cc1]

Methyl 2-(N-methylbiphenyl-4-ylsulfonamido)acetate (12c). This was obtained as an oil from N-methylglycine methyl ester (11) (1.5 g, 10.75 mmol) and 4-phenyl-benzenesulfonyl chloride (3.705 g, 12.9 mmol) in the same manner as described for 12a. ¹H NMR (400 MHz, CDCl₃) δ 7.87 (d, J=8.5 Hz, 2H), 7.72 (d, J=8.5 Hz, 2H), 7.61 (d, J=1.5 Hz, 2H), 7.50-7.45 (m, 2H), 7.43-7.38 (m, 1H), 4.02 (s, 2H), 3.66 (s, 3H), 2.93 (s, 3H).

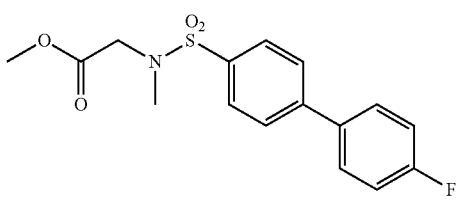 [SMILES: COC(=O)CN(C)S(=O)(=O)c1ccc(-c2ccc(F)cc2)cc1]

Methyl 2-(4'-fluoro-N-methylbiphenyl-4-ylsulfonamido) acetate (12d). This was obtained as a viscous oil (2.2 g) from N-methylglycine methyl ester (11) (1.9 g, 7.16 mmol) and 4-phenyl-benzenesulfonyl chloride (2.33 g, 8.6 mmol) in the same manner as described for 12a.

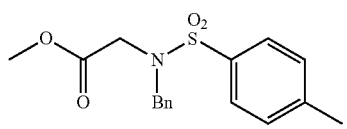

Methyl 2-(N-benzyl-4-methylphenylsulfonamido)acetate (12e). This was obtained as a viscous oil from N-benzylglycine methyl ester (10) (1.0 g, 5.58 mmol) and tosyl chloride (1.27 g, 6.70 mmol) in the same manner as described for 12a.

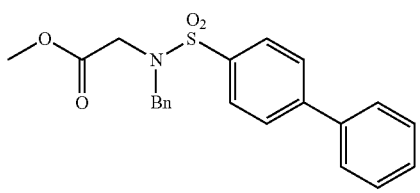 [SMILES: COC(=O)CN(Cc1ccccc1)S(=O)(=O)c1ccc(-c2ccccc2)cc1]

Methyl 2-(N-benzylbiphenyl-4-ylsulfonamido)acetate (12f). This was obtained as a viscous oil from N-benzylglycine methyl ester (10) (1.59 g, 8.37 mmol) and 4-phenyl-benzenesulfonyl chloride (2.53 g, 10.05 mmol) in the same manner as described for 12a.

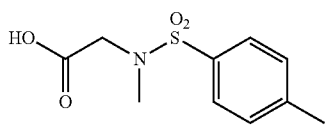 [SMILES: Cc1ccc(S(=O)(=O)N(C)CC(=O)O)cc1]

2-(N,4-Dimethylphenylsulfonamido)acetic acid (7a). Lithium hydroxide (0.146 g, 6.10 mmol) was added to a solution of 12a (0.705 g, 3.05 mmol) in MeOH-THF—H$_2$O (10 mL, 3:1:1) and was stirred overnight at room temperature. The organic solvent was then removed under reduced pressure. The resulting solution was acidified with HCl (aq. 1 M) and extracted with AcOEt. The organic extracts were combined, dried (Na$_2$SO$_4$), filtered, and the solvent removed under reduced pressure to afford 7a (97%). $^1$H NMR (400 MHz, CDCl$_3$) δ 8.79 (s, 1H), 7.69 (d, J=8.3 Hz, 2H), 7.32 (d, J=8.1 Hz, 2H), 3.98 (s, 2H), 2.87 (s, 3H), 2.43 (s, 3H).

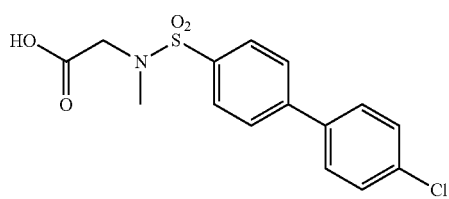 [SMILES: CN(CC(=O)O)S(=O)(=O)c1ccc(-c2ccc(Cl)cc2)cc1]

2-(4'-Chloro-N-methylbiphenyl-4-ylsulfonamido)acetic acid (7b). This was obtained as a solid from 12b (2.4 g, 7.16 mmol) in the same manner as described for 7a. $^1$H NMR (400 MHz, CDCl$_3$) δ 7.88 (d, J=8.5 Hz, 2H), 7.69 (d, J=8.6 Hz, 2H), 7.54 (d, J=8.6 Hz, 2H), 7.46 (d, J=8.6 Hz, 2H), 4.04 (s, 2H), 2.93 (s, 3H). HRMS (ESI–ve) Calcd for C$_{15}$H$_{16}$ClNO$_4$S 340.0404 [M+H]$^+$, found 340.0408.

2-(N-Methylbiphenyl-4-ylsulfonamido)acetic acid (7c). This was obtained as a solid (70%) 12c (0.551 g, 1.72 mmol) in the same manner as described for 7a. $^1$H NMR (400 MHz, CD$_3$OD) δ 7.76 (d, J=8.3 Hz, 2H), 7.38 (d, J=8.2 Hz, 2H), 7.33-7.25 (m, 3H), 7.23-7.18 (m, 2H), 4.47 (s, 3H), 2.44 (s, 3H). HRMS (ESI–ve) Calcd for C$_{15}$H$_{16}$NO$_4$S 306.0794 [M+H]$^+$, found 306.0808.

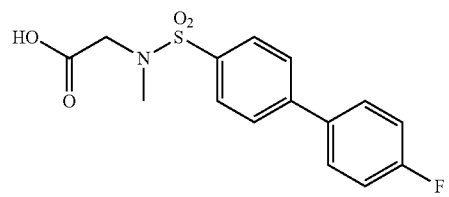 [SMILES: CN(CC(=O)O)S(=O)(=O)c1ccc(-c2ccc(F)cc2)cc1]

2-(4'-Fluoro-N-methylbiphenyl-4-ylsulfonamido)acetic acid (7d). This was obtained as a solid (0.500 g, 85%) from 12d (0.500 g, 1.41 mmol) in the same manner as described for 7a. $^1$H NMR (400 MHz, CD$_3$OD) δ 7.89 (d, J=8.7 Hz, 2H), 7.81 (d, J=8.6 Hz, 2H), 7.71 (dd, J=8.9, 5.2 Hz, 2H), 7.22 (t, J=8.8 Hz, 2H), 3.97 (s, 2H), 2.89 (s, 3H). HRMS (ESI–ve) Calcd for C$_{15}$H$_{15}$NFO$_4$S 324.0700 [M+H]$^+$, found 324.0708.

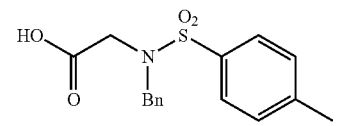 [SMILES: Cc1ccc(S(=O)(=O)N(CC(=O)O)Cc2ccccc2)cc1]

2-(N-Benzyl-4-methylphenylsulfonamido)acetic acid (7e). This was obtained (1.119 g, 62%) from 12e (1.896 g, 5.58 mmol) in the same manner as described for 7a. $^1$H NMR (400 MHz, CD$_3$OD) δ 7.76 (d, J=8.3 Hz, 2H), 7.38 (d, J=8.2 Hz, 2H), 7.31-7.25 (m, 3H), 7.23-7.19 (m, 2H), 4.47 (s, 2H), 3.85 (s, 2H), 2.44 (s, 3H).

2-(N-Benzylbiphenyl-4-ylsulfonamido)acetic acid (7l). This was obtained as solid (0.500 g, 85%) from 12f (0.500 g, 1.41 mmol) in the same manner as described for 7a. $^1$H NMR (400 MHz, CD$_3$OD) δ 7.94 (d, J=8.5 Hz, 2H), 7.81 (d, J=8.6 Hz, 2H), 7.71-7.66 (m, 2H), 7.48 (t, J=7.4 Hz, 2H), 7.41 (t, J=7.4 Hz, 1H), 7.33-7.20 (m, 6H), 4.53 (s, 3H), 3.90 (s, 2H).

Synthesis of Methyl Esters 8

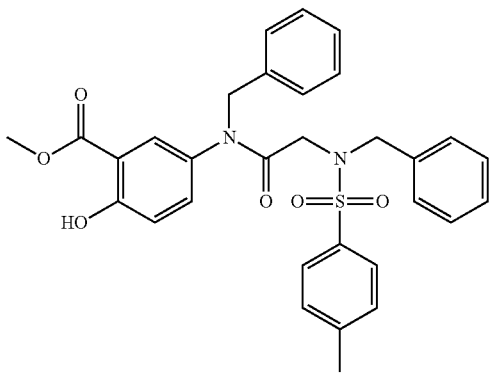 [SMILES: COC(=O)c1cc(N(Cc2ccccc2)C(=O)CN(Cc2ccccc2)S(=O)(=O)c2ccc(C)cc2)ccc1O]

Methyl 5-(N-benzyl-2-(N-benzyl-4-methylphenylsulfonamido)acetamido)-2-hydroxybenzoate (8a). To a solution of an amine 6a (0.100 g, 0.388 mmol) in CH$_2$Cl$_2$ (2 ml) was added the acid 7e (0.130 g, 0.408 mmol) and coupling reagent Ph$_3$PCl$_2$ (0.010 g, 0.932 mmol) under argon atmosphere. The resultant mixture was heated at 80° C. in a microwave reactor (Biotage) for 1 h. The reaction was cooled to room temperature, diluted with CH$_2$Cl$_2$ and washed with sat. NaHCO$_3$. The organic fractions are dried (Na$_2$SO$_4$) and evaporated in vacuo. The crude mixture was purified by column chromatography to afford the ester 8a (0.100 g, 0.179 mmol, 50%). $^1$H NMR (400 MHz, CDCl$_3$) δ 10.76 (s, 1H), 7.82 (d, J=8.3 Hz, 2H), 7.32 (d, J=8.0 Hz, 2H), 7.29-7.21 (m, 7H), 7.21-7.15 (m, 2H), 7.08-7.00 (m, 2H), 6.73 (d, J=8.8 Hz, 1H), 6.53 (dd, J=8.8, 2.7 Hz, 1H), 4.68 (s, 2H), 4.53 (s, 2H), 3.90 (s, 3H), 3.63 (s, 2H), 2.45 (s, 3H). HRMS (ESI–ve) Calcd for C$_{31}$H$_{31}$N$_2$O$_6$S 559.1897 [M+H]$^+$, found 559.1871.

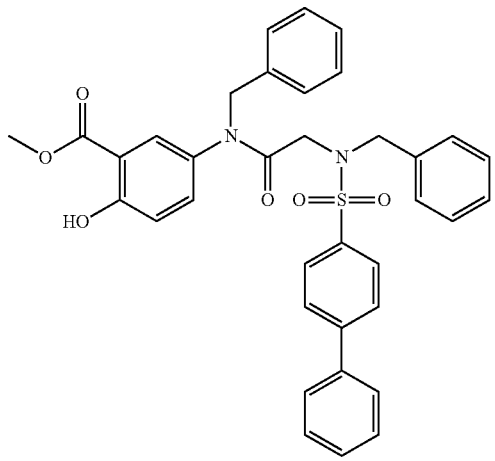 [SMILES: COC(=O)c1cc(N(Cc2ccccc2)C(=O)CN(Cc2ccccc2)S(=O)(=O)c2ccc(-c3ccccc3)cc2)ccc1O]

Methyl 5-(N-benzyl-2-(N-benzylbiphenyl-4-ylsulfonamido)acetamido)-2-hydroxybenzoate (8b). This was obtained as a solid (0.108 g, 75%) from acid 7f (0.093 g, 0.244 mmol) and amine 6a (0.060 g, 0.233 mmol) in the same manner as described for 8a. $^1$H NMR (400 MHz, CDCl$_3$) δ 10.77 (s, 1H), 8.00 (d, J=10.4 Hz, 1H), 7.73 (d, J=10.3 Hz, 1H), 7.65-7.62 (m, 1H), 7.49 (t, J=7.4 Hz, 2H), 7.44-7.39 (m, 1H), 7.30-7.16 (m, 9H), 7.07-7.04 (m, 2H), 6.74 (d, J=8.8 Hz, 1H), 6.55 (dd, J=8.8, 2.7 Hz, 1H), 4.69 (s, 2H), 4.58 (s, 2H), 3.91 (s, 3H), 3.68 (s, 2H). HRMS (ESI–ve) Calcd for C$_{36}$H$_{33}$N$_2$O$_6$S 621.2053 [M+H]$^+$, found 621.2022.

Methyl 5-(2-(N-benzyl-4-methylphenylsulfonamido)-N-(4-chlorobenzyl)acetamido)-2-hydroxybenzoate (8c). This was obtained as a solid (0.170 g, 70%) from acid 7c (0.153 g, 0.482 mmol) and amine 6d (0.120 g, 0.411 mmol) in the same manner as described for 8a. $^1$H NMR (400 MHz, CDCl$_3$) δ 10.78 (s, 1H), 7.80 (d, J=8.3 Hz, 2H), 7.31 (d, J=7.9 Hz, 2H), 7.26-7.22 (m, 6H), 7.18-7.13 (m, 2H), 6.99 (d, J=8.4 Hz, 2H), 6.76 (d, J=8.9 Hz, 1H), 6.56 (dd, J=8.7, 2.7 Hz, 1H), 4.64 (s, 2H), 3.92 (s, 2H), 3.63 (s, 3H), 2.45 (s, 3H). HRMS (ESI–ve) Calcd for C$_{31}$H$_{29}$ClN$_2$O$_6$S 593.1507 [M–H]$^-$, found 593.1482.

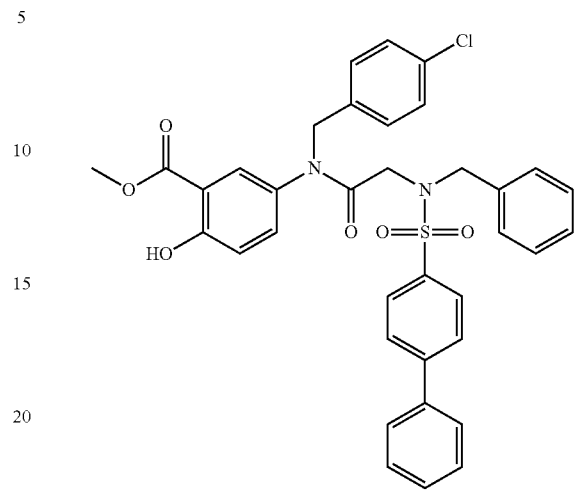

Methyl 5-(2-(N-benzylbiphenyl-4-ylsulfonamido)-N-(4-chlorobenzyl)acetamido)-2-hydroxybenzoate (8d). This was obtained as a solid (0.114 g, 75%) from acid 7f (0.093 g, 0.244 mmol) and amine 6d (0.068 g, 0.233 mmol) in the same manner as described for 8a. $^1$H NMR (400 MHz, CDCl$_3$) δ 10.79 (s, 1H), 7.99 (d, J=8.5 Hz, 2H), 7.73 (d, J=8.5 Hz, 2H), 7.64 (d, J=7.2 Hz, 2H), 7.54-7.47 (m, 1H), 7.44-7.38 (m, 1H), 7.25-7.20 (m, 4H), 7.02-7.16 (m, 4H), 7.00 (d, J=8.4 Hz, 1H), 6.78 (d, J=8.8 Hz, 1H), 6.58 (dd, J=8.8, 2.7 Hz, 1H), 4.65 (s, 2H), 4.57 (s, 2H), 3.92 (s, 3H), 3.67 (s, 2H). HRMS (ESI–ve) Calcd for C$_{36}$H$_{32}$ClN$_2$O$_6$S 655.1664 [M+H]$^+$, found 655.1634.

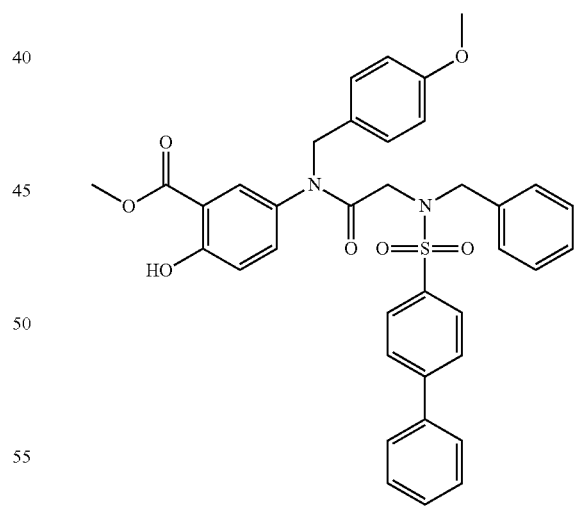

Methyl 5-(2-(N-benzylbiphenyl-4-ylsulfonamido)-N-(4-methoxybenzyl)acetamido)-2-hydroxybenzoate (8f). This was obtained as a solid (0.111 g, 89%) from acid 7f (0.084 g, 0.219 mmol) and amine 6c (0.060 g, 0.209 mmol) in the same manner as described for 8a. $^1$H NMR (400 MHz, CDCl$_3$) δ 10.77 (s, 1H), 8.00 (d, J=8.4 Hz, 2H), 7.74 (d, J=8.5 Hz, 2H), 7.65 (d, J=7.2 Hz, 2H), 7.51-7.45 (m, 1H), 7.44-7.37 (m, 1H), 7.29-7.14 (m, 7H), 6.96 (d, J=8.6 Hz, 1H), 6.77-6.70 (m, 3H), 6.53 (dd, J=8.8, 2.7 Hz, 1H), 4.63

(s, 2H), 4.59 (s, 2H), 3.74 (s, 3H), 3.66 (s, 2H). HRMS (ESI−ve) Calcd for $C_{37}H_{25}N_2O_7S$ 651.2159 [M+H]$^+$, found 651.2126.

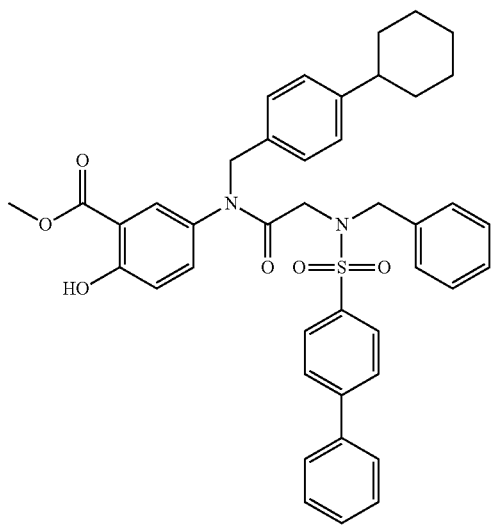 [SMILES: COC(=O)c1cc(N(Cc2ccc(C3CCCCC3)cc2)C(=O)CN(Cc2ccccc2)S(=O)(=O)c2ccc(-c3ccccc3)cc2)ccc1O]

Methyl 5-(2-(N-benzylbiphenyl-4-ylsulfonamido)-N-(4-cyclohexylbenzyl)acetamido)-2-hydroxybenzoate (8g). This was obtained as a solid (0.146 g, 71%) from acid 7f (0.118 g, 0.309 mmol) and amine 6b (0.100 g, 0.294 mmol) in the same manner as described for 8a. $^1$H NMR (400 MHz, CDCl$_3$) δ 10.78 (s, 1H), 8.01 (d, J=10.3 Hz, 1H), 7.75 (d, J=8.5 Hz, 2H), 7.66 (d, J=7.0 Hz, 2H), 7.53-7.46 (m, 2H), 7.45-7.38 (m, 1H), 7.24-7.20 (m, 7H), 7.05 (d, J=8.0 Hz, 2H), 6.96 (d, J=8.1 Hz, 2H), 6.76 (d, J=8.8 Hz, 1H), 6.58 (dd, J=8.8, 2.7 Hz, 1H), 4.65 (s, 2H), 4.61 (s, 2H), 3.91 (s, 3H), 3.67 (s, 2H), 2.49-2.35 (m, 1H), 1.78 (m, 6H), 1.44-1.14 (m, 4H).

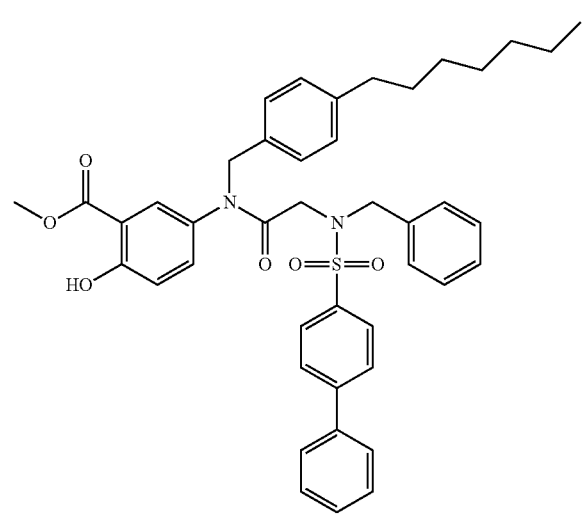 [SMILES: CCCCCCCc1ccc(CN(C(=O)CN(Cc2ccccc2)S(=O)(=O)c2ccc(-c3ccccc3)cc2)c2ccc(O)c(C(=O)OC)c2)cc1]

Methyl 5-(2-(N-benzylbiphenyl-4-ylsulfonamido)-N-(4-heptylbenzyl)acetamido)-2-hydroxybenzoate (8h). This was obtained as a solid (0.160 g, 79%) from acid 7f(0.112 g, 0.295 mmol) and amine 6i (0.100 g, 0.282 mmol) in the same manner as described for 8a. $^1$H NMR (400 MHz, CDCl$_3$) δ 10.78 (s, 1H), 8.01 (d, J=8.4 Hz, 2H), 7.75 (d, J=8.5 Hz, 2H), 7.65 (d, J=7.8 Hz, 1H), 7.50 (t, J=7.5 Hz, 2H), 7.43 (t, J=7.3 Hz, 1H), 7.29-7.13 (m, 6H), 7.03 (d, J=7.9 Hz, 2H), 6.96 (d, J=8.0 Hz, 2H), 6.75 (d, J=8.8 Hz, 1H), 6.55 (dd, J=8.8, 2.6 Hz, 1H), 4.66 (s, 2H), 3.92 (s, 2H), 3.68 (s, 3H), 2.66-2.35 (m, 2H), 1.66-1.46 (m, 1H), 1.35-1.17 (m, 9H), 0.88 (t, J=6.9 Hz, 3H). HRMS (ESI−ve) Calcd for $C_{43}H_{47}N_2O_6S$ 719.3149 [M+H]$^+$, found 719.3146.

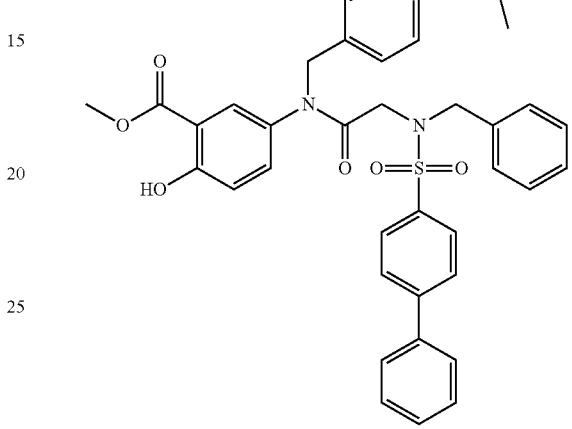

Methyl 5-(2-(N-benzylbiphenyl-4-ylsulfonamido)-N-(4-isobutylbenzyl)acetamido)-2-hydroxybenzoate (8i). This was obtained as a solid (0.120 g, 70%) from acid 7f (0.102 g, 0.344 mmol) and amine 6g (0.100 g, 0.319 mmol) in the same manner as described for 8a. $^1$H NMR (400 MHz, CDCl$_3$) δ 10.78 (s, 1H), 8.02 (d, J=8.5 Hz, 2H), 7.75 (d, J=8.5 Hz, 2H), 7.65 (d, J=8.0 Hz, 2H), 7.49 (t, J=7.5 Hz, 2H), 7.42 (t, J=7.3 Hz, 1H), 7.27-7.17 (m, 7H), 6.99 (d, J=8.0 Hz, 2H), 6.94 (d, J=8.1 Hz, 2H), 6.75 (d, J=8.8 Hz, 1H), 6.57 (dd, J=8.8, 2.6 Hz, 1H), 4.66 (s, 2H), 4.60 (s, 2H), 3.89 (s, 3H), 3.67 (s, 2H), 2.41 (d, J=7.2 Hz, 2H), 1.89-1.68 (m, 1H), 0.87 (d, J=6.6 Hz, 5H). HRMS (ESI−ve) Calcd for $C_{40}H_{41}N_2O_6S$ 677.2679 [M+H]$^+$, found 677.2686.

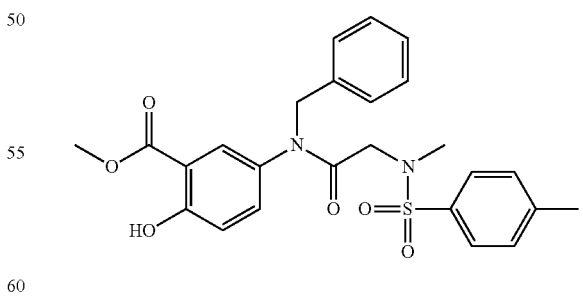

Methyl 5-(N-benzyl-2-(N,4-dimethylphenylsulfonamido)acetamido)-2-hydroxybenzoate (8j). This was obtained as a solid from acid 7f (0.083 g, 0.342 mmol) and amine 6a (0.084 g, 0.326 mmol) in the same manner as described for 8a and used immediately in the next step.

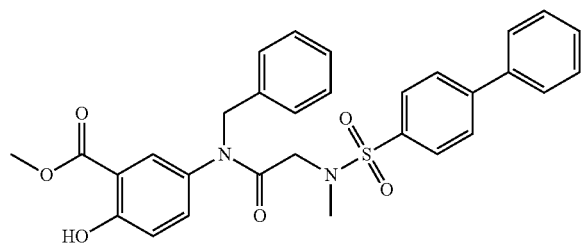 [SMILES: COC(=O)c1cc(N(Cc2ccccc2)C(=O)CN(C)S(=O)(=O)c2ccc(-c3ccccc3)cc2)ccc1O]

Methyl 5-(N-benzyl-2-(N-methylbiphenyl-4-ylsulfonamido)acetamido)-2-hydroxybenzoate (8k). This was obtained as a solid (50-55%) from acid 7c (0.250 g, 0.818 mmol) and amine 6a (0.200 g, 0.778 mmol) in the same manner as described for 8a. $^1$H NMR (400 MHz, CDCl$_3$) δ 10.86 (s, 1H), 7.84 (d, J=8.5 Hz, 2H), 7.69 (d, J=8.5 Hz, 2H), 7.60 (dd, J=8.3, 1.2 Hz, 3H), 7.51 (d, J=2.6 Hz, 1H), 7.48 (t, J=7.3 Hz, 2H), 7.41 (d, J=2.3 Hz, OH), 7.28-7.23 (m, 4H), 7.12 (d, J=2.6 Hz, 1H), 7.00 (dd, J=8.8, 2.6 Hz, 1H), 6.94 (d, J=8.8 Hz, 1H), 4.79 (s, 2H), 3.94 (s, 3H), 3.78 (s, 2H), 2.93 (s, 3H).

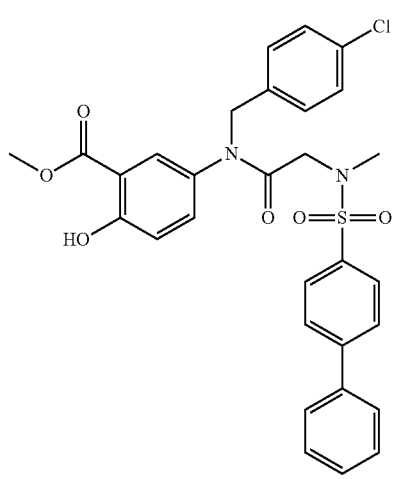 [SMILES: COC(=O)c1cc(N(Cc2ccc(Cl)cc2)C(=O)CN(C)S(=O)(=O)c2ccc(-c3ccccc3)cc2)ccc1O]

Methyl 5-(N-(4-chlorobenzyl)-2-(N-methylbiphenyl-4-ylsulfonamido)acetamido)-2-hydroxybenzoate (8l). This was obtained as a solid from acid 7c and amine 6d in the same manner as described for 8a and used immediately in the next step.

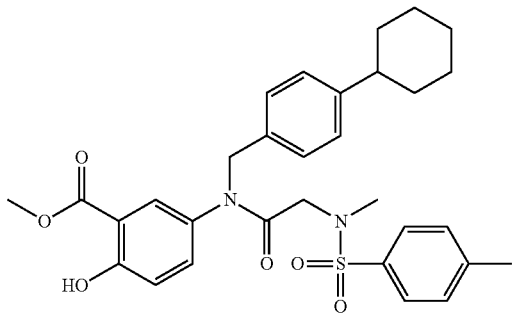

Methyl 5-(N-(4-cyclohexylbenzyl)-2-(N,4-dimethylphenylsulfonamido)acetamido)-2-hydroxybenzoate (8m). This was obtained as a solid (40-45%) from acid 7a (0.075 g, 0.309 mmol) and amine 6b (0.100 g, 0.294 mmol) in the same manner as described for 8a. $^1$H NMR (400 MHz, CDCl$_3$) δ 10.85 (s, 1H), 7.64 (d, J=8.3 Hz, 2H), 7.45 (d, J=2.6 Hz, 1H), 7.27 (d, J=7.9 Hz, 2H), 7.10 (d, J=8.1 Hz, 2H), 7.05-6.97 (m, 3H), 6.93 (d, J=8.8 Hz, 1H), 4.73 (s, 2H), 3.93 (s, 3H), 3.70 (s, 2H), 2.86 (s, 3H), 2.47 (s, 3H), 2.48-2.41 (m, 1H), 1.79 (m, 6H), 1.46-1.15 (m, 4H).

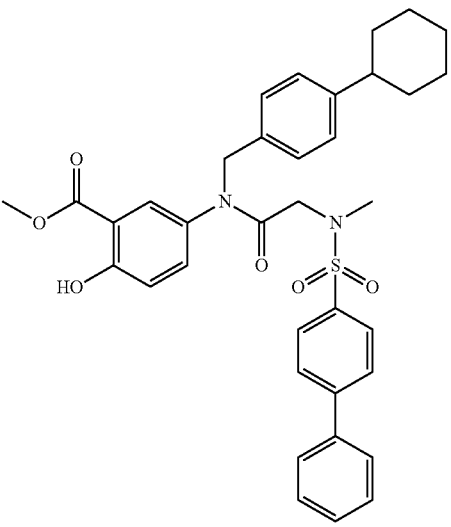 [SMILES: COC(=O)c1cc(N(Cc2ccc(C3CCCCC3)cc2)C(=O)CN(C)S(=O)(=O)c2ccc(-c3ccccc3)cc2)ccc1O]

Methyl 5-(N-(4-cyclohexylbenzyl)-2-(N-methylbiphenyl-4-ylsulfonamido)acetamido)-2-hydroxy-benzoate (8n). This was obtained as a solid (0.060 g, 0.096 mmol, 45%) from acid 7c (0.076 g, 0.248 mmol) and 6b (0.080 g, 0.236 mmol) in the same manner as described for 8a. $^1$H NMR (400 MHz, CDCl$_3$) δ 10.86 (s, 1H), 7.84 (d, J=8.4 Hz, 2H), 7.69 (d, J=8.5 Hz, 2H), 7.63-7.59 (m, 3H), 7.50-7.45 (m, 2H), 7.44-7.40 (m, 1H), 7.07 (m, J=8.1 Hz, 2H), 7.03-6.98 (m, 3H), 6.94 (d, J=8.8 Hz, 1H), 4.73 (s, 2H), 3.93 (s, 3H), 2.93 (s, 3H), 2.44-2.42 (m, 1H), 1.82-1.73 (m, 6H), 1.42-1.14 (m, 2H). HRMS (ESI–ve) Calcd for C$_{36}$H$_{39}$N$_2$O$_6$S 627.2523 [M+H]$^+$, found 637.2529.

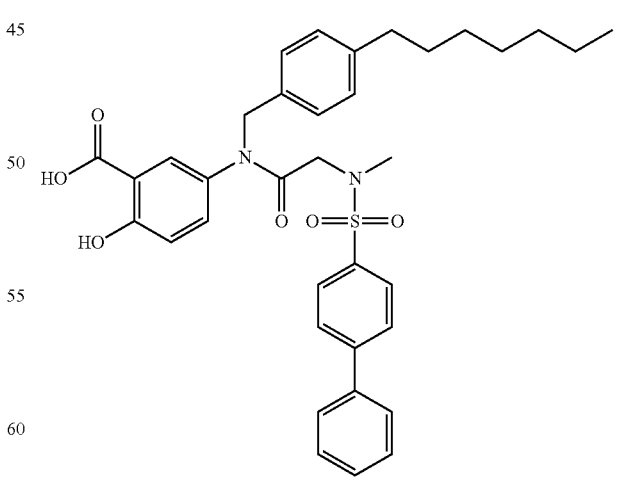

5-(N-(4-Heptylbenzyl)-2-(N-methylbiphenyl-4-ylsulfonamido)acetamido)-2-hydroxybenzoic acid (8o). This was obtained as a solid (0.088 g, 50%) from acid 7c (0.090 g, 0.294 mmol) and amine 6i (0.100 g, 0.282 mmol) in the same manner as described for 8a. ¹H NMR (400 MHz, CDCl₃) δ 10.86 (s, 1H), 7.84 (d, J=8.5 Hz, 2H), 7.69 (d, J=6.7 Hz, 1H), 7.63-7.59 (m, 2H), 7.52-7.45 (m, 2H), 7.44-7.39 (m, 1H), 7.10-6.97 (m, 5H), 6.93 (d, J=8.8 Hz, 1H), 4.75 (s, 2H), 3.93 (s, 3H), 3.76 (s, 2H), 2.93 (s, 3H), 2.63-2.42 (m, 2H), 1.60-1.46 (m, 1H), 1.37-1.18 (m, 9H), 1.03-0.71 (m, 3H).

7b (0.083 g, 0.244 mmol) and amine 6d (0.068 g, 0.233 mmol) in the same manner as described for 8a. ¹H NMR (400 MHz, CDCl₃) δ 10.87 (s, 1H), 7.83 (d, J=8.5 Hz, 2H), 7.64 (d, J=8.5 Hz, 2H), 7.52 (d, J=8.7 Hz, 1H), 7.48 (d, J=2.5 Hz, 1H), 7.44 (d, J=8.7 Hz, 1H), 7.22 (d, J=8.4 Hz, 1H), 7.07 (d, J=6.7 Hz, 1H), 7.03-6.90 (m, 2H), 4.74 (s, 2H), 3.94 (s, 3H), 3.76 (s, 2H), 2.89 (s, 3H).

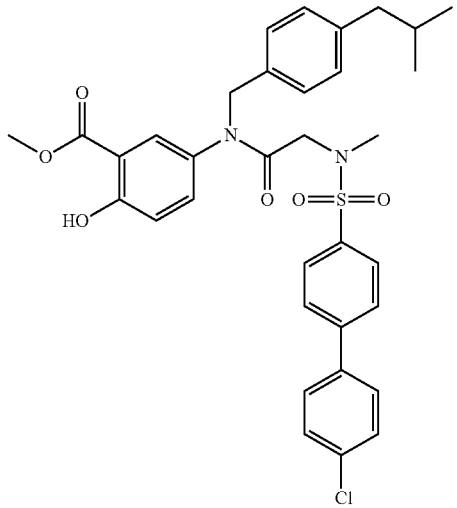 [SMILES: COC(=O)c1cc(N(Cc2ccc(CC(C)C)cc2)C(=O)CN(C)S(=O)(=O)c2ccc(-c3ccc(Cl)cc3)cc2)ccc1O]

Methyl 5-(2-(4'-chloro-N-methylbiphenyl-4-ylsulfonamido)-N-(4-isobutylbenzyl)acetamido)-2-hydroxy-benzoate (8p). This was obtained as a solid (0.141g, 87%) from acid 7b (0.091 g, 0.268 mmol) and amine 6g (0.080 g, 0.255 mmol) in the same manner as described for 8a. ¹H NMR (400 MHz, CDCl₃) δ 10.86 (s, 1H), 7.87 (d, J=1.5 Hz, 1H), 7.65 (d, J=1.5 Hz, 1H), 7.54 (d, J=8.5 Hz, 1H), 7.47-7.42 (m, 3H), 7.02-7.98 (m, 4H), 6.94 (d, J=8.8 Hz, 1H), 4.75 (s, 2H), 3.92 (s, 3H), 3.78 (s, 2H), 2.93 (s, 3H), 2.42 (d, J=7.2 Hz, 2H), 1.76-1.86 (m, 1H), 0.87 (d, J=6.6 Hz, 6H). HRMS (ESI–ve) Calcd for C₃₄H₃₆ClN₂O₆S 635.1977 [M+H]¹, found 635.1982.

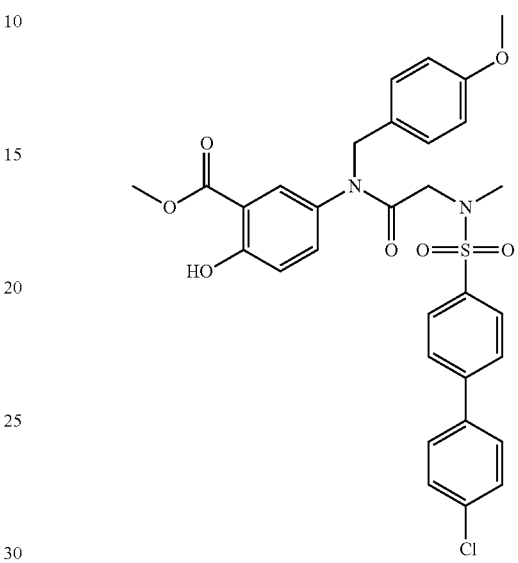

Methyl 5-(2-(4'-chloro-N-methylbiphenyl-4-ylsulfonamido)-N-(4-methoxybenzyl)acetamido)-2-hydroxy-benzoate (8r). This was obtained as a solid (0.100 g, 73%) from acid 7b (0.075 g, 0.219 mmol) and amine 6c (0.060 g, 0.209 mmol) in the same manner as described for 8a. ¹H NMR (400 MHz, CDCl₃) δ 10.85 (s, 1H), 7.84 (d, J=8.4 Hz, 2H), 7.64 (d, J=8.5 Hz, 2H), 7.53 (d, J=8.6 Hz, 2H), 7.49 (d, J=2.3 Hz, 1H), 7.44 (d, J=8.6 Hz, 1H), 7.02 (d, J=8.6 Hz, 1H)., 6.98-6.87 (m, 2H), 6.75 (d, J=8.6 Hz, 1H), 4.71 (s, 2H), 3.94 (s, 3H), 3.76 (s, 5H), 2.90 (s, 3H). HRMS (ESI–ve) Calcd for C₃₁H₂₉ClN₂O₇S 609.1456 [M+H]⁺, found 609.1448.

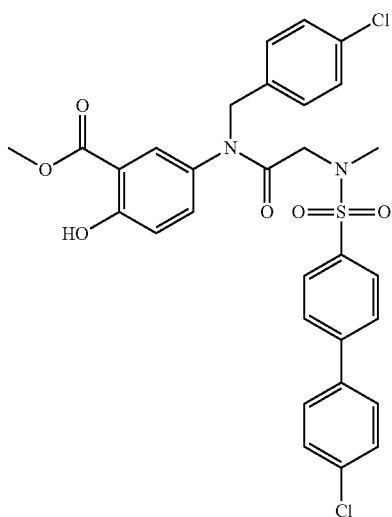 [SMILES: COC(=O)c1cc(N(Cc2ccc(Cl)cc2)C(=O)CN(C)S(=O)(=O)c2ccc(-c3ccc(Cl)cc3)cc2)ccc1O]

Methyl 5-(2-(4'-chloro-N-methylbiphenyl-4-ylsulfonamido)-N-(4-chlorobenzyl)acetamido)-2-hydroxy-benzoate (8q). This was obtained as a solid (0.085 g, 60%) from acid

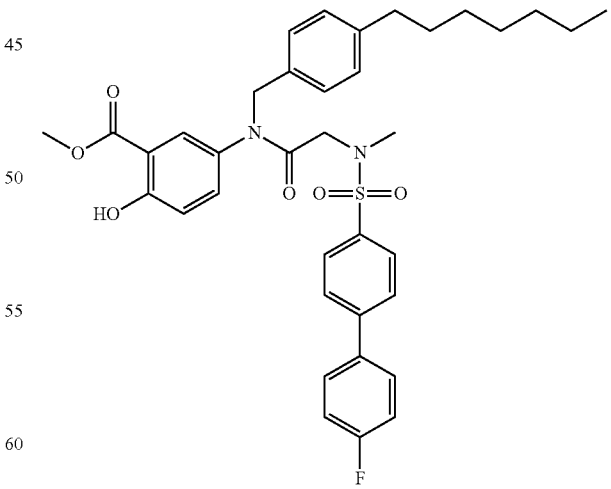

Methyl 5-(2-(4'-fluoro-N-methylbiphenyl-4-ylsulfonamido)-N-(4-heptylbenzyl)acetamido)-2-hydroxy-benzoate (8s). This was obtained as a solid from acid 7d (0.095 g, 0.295 mmol) and amine 6i (0.100 g, 0.282 mmol) in the same manner as described for 8a. ¹H NMR (400 MHz, CDCl$_3$) δ 10.86 (s, 1H), 7.85 (d, J=8.5 Hz, 2H), 7.66 (d, J=8.5 Hz, 2H), 7.58 (dd, J=8.8, 5.2 Hz, 2H), 7.50 (d, J=2.5 Hz, 1H), 7.17 (t, J=8.6 Hz, 2H), 7.05 (d, J=8.1 Hz, 2H), 7.03-6.90 (m, 4H), 4.75 (s, 2H), 3.94 (s, 3H), 3.78 (s, 2H), 2.92 (s, 3H), 2.64-2.46 (m, 2H), 1.56 (s, 1H), 1.42-1.17 (m, 9H), 0.99-0.77 (m, 3H).

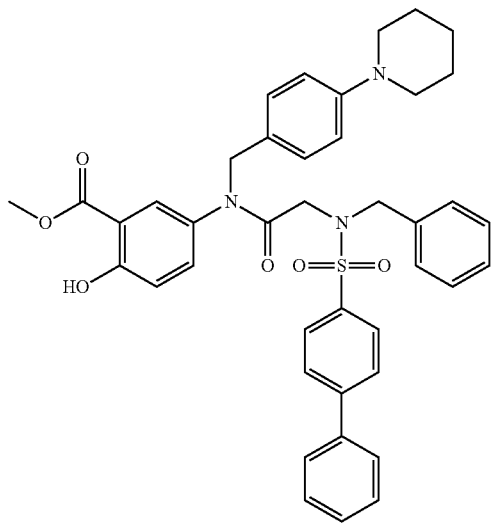

Methyl 5-(2-(N-benzylbiphenyl-4-ylsulfonamido)-N-(4-(piperidin-1-yl)benzyl)acetamido)-2-hydroxy-benzoate (8t). This was obtained as a solid (0.113 g, 55%) from acid 7f (0.117 g, 0.308 mmol) and amine 6h (0.100 g, 0.294 mmol) in the same manner as described for 8a and was used in the next step without purification. $^1$H NMR (400 MHz, CDCl$_3$) δ 10.78 (s, 1H), 8.01 (d, J=8.5 Hz, 2H), 7.75 (d, J=8.5 Hz, 2H), 7.68-7.65 (m, 3H), 7.53-7.46 (m, 2H), 7.30-7.20 (m, 6H), 6.90-6.87 (m, 2H), 6.74 (dd, J=8.7, 1.7 Hz, 2H), 6.55 (dd, J=8.8, 2.7 Hz, 1H), 4.63 (s, 2H), 3.94 (s, 2H), 3.92 (s, 3H), 3.66 (s, 2H), 3.21-2.84 (m, 4H), 1.77-1.42 (m, 6H). HRMS (ESI−ve) Calcd for C$_{41}$H$_{42}$N$_3$O$_6$S 704.2788 [M+H]$^+$, found 704.2788.

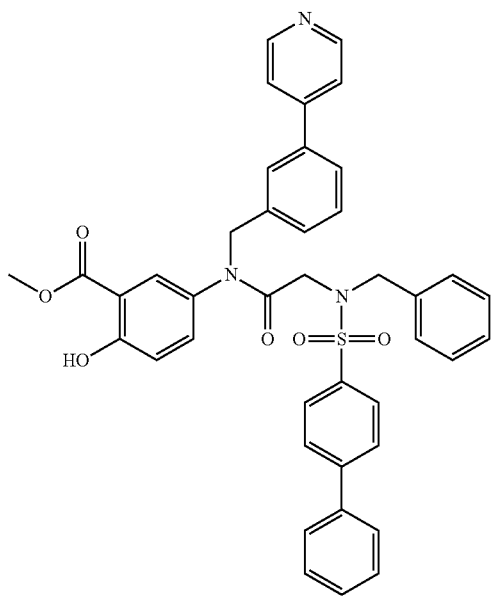 [SMILES: COC(=O)c1cc(N(Cc2cccc(-c3ccncc3)c2)C(=O)CN(Cc2ccccc2)S(=O)(=O)c2ccc(-c3ccccc3)cc2)ccc1O]

Methyl 5-(2-(N-benzylbiphenyl-4-ylsulfonamido)-N-(3-(pyridin-4-yl)benzyl)acetamido)-2-hydroxy-benzoate (8u). This was obtained as a solid (0.085 g, 50%) from acid 7f (0.119 g, 0.313 mmol) and amine 6f (0.100 g, 0.299 mmol) in the same manner as described for 8a. $^1$H NMR (400 MHz, CDCl$_3$) δ 10.80 (s, 1H), 8.63 (s, 2H), 8.00 (d, J=8.5 Hz, 2H), 7.73-7.60 (m, 8H), 7.59-7.33 (m, 16H), 7.29-7.12 (m, 7H), 6.80 (d, J=8.8 Hz, 1H), 6.65 (dd, J=8.8, 2.7 Hz, 1H), 4.79 (s, 2H), 4.56 (s, 2H), 3.90 (s, 2H), 3.71 (s, 3H). HRMS (ESI−ve) Calcd for C$_{41}$H$_{36}$N$_3$O$_6$S 698.2319 [M+H]$^+$, found 698.2330.

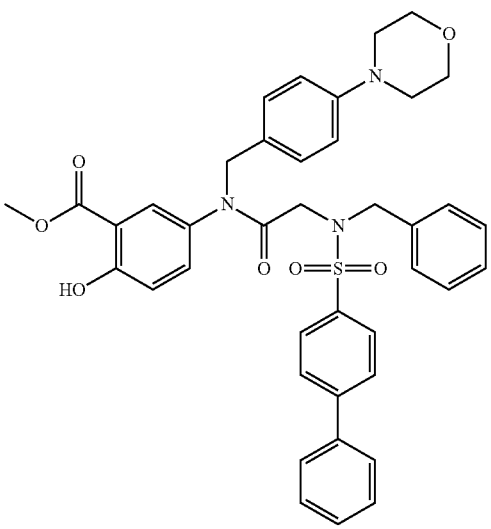

Methyl 5-(2-(N-benzylbiphenyl-4-ylsulfonamido)-N-(4-morpholinobenzyl)acetamido)-2-hydroxybenzoate (8v). This was obtained as a solid (0.100 g, 60%) from acid 7f (0.117 g, 0.308) and amine 6e (0.100 g, 0.294 mmol) in the same manner as described for 8a. $^1$H NMR (400 MHz, CDCl$_3$) δ 10.78 (s, 1H), 8.01 (d, J=8.5 Hz, 2H), 7.75 (d, J=8.5 Hz, 2H), 7.69-7.62 (m, 3H), 7.53-7.48 (m, 2H), 7.45-7.39 (m, 1H), 7.34-7.20 (m, 7H), 6.92 (d, J=8.7 Hz, 2H), 6.77 (s, 1H), 6.71 (d, J=8.7 Hz, 2H), 6.57 (dd, J=8.9, 2.7 Hz, 1H), 4.64 (s, 3H), 3.93 (s, 4H), 3.87-3.81 (m, 7H), 3.66 (s, 2H), 3.12-3.02 (m, 7H).

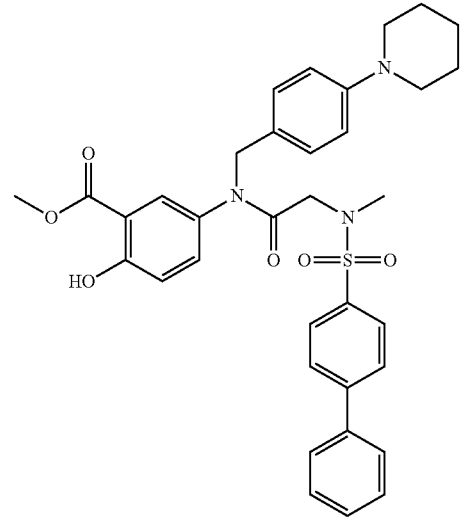 [SMILES: COC(=O)c1cc(N(Cc2ccc(N3CCCCC3)cc2)C(=O)CN(C)S(=O)(=O)c2ccc(-c3ccccc3)cc2)ccc1O]

Methyl 2-hydroxy-5-(2-(N-methylbiphenyl-4-ylsulfonamido)-N-(4-(piperidin-1-yl)benzyl)acetamido)-benzoate (8w). This was obtained as a solid (0.080 g, 45%) from acid 7c (0.094g, 0.308 mmol) and amine 6h (0.100 g, 0.294 mmol) in the same manner as described for 8a. $^1$H NMR (400 MHz, CDCl$_3$) δ 10.85 (s, 1H), 7.83 (d, J=8.5 Hz, 2H), 7.69 (d, J=8.5 Hz, 2H), 7.63-7.58 (m, 2H), 7.51-7.44 (m, 3H), 7.41-7.40 (m, 1H), 6.99-6.89 (m, 5H), 6.76 (d, J=8.7 Hz, 2H), 4.67 (s, 2H), 3.95 (s, 3H), 3.74 (s, 2H), 3.13-3.01 (m, 4H), 2.93 (s, 3H), 1.67-1.65 (m, 4H), 1.59-1.48 (m, 1H). HRMS (ESI-ve) Calcd for C$_{35}$H$_{36}$N$_3$O$_6$S 628.2475 [M+H],$^+$, found 628.2575.

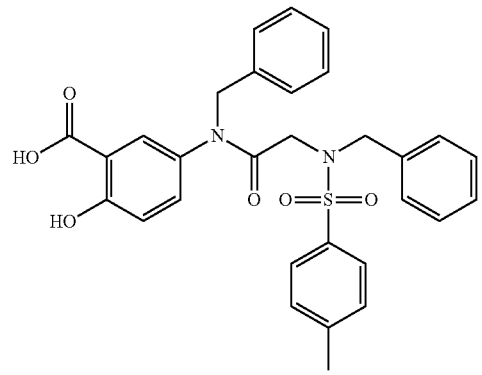

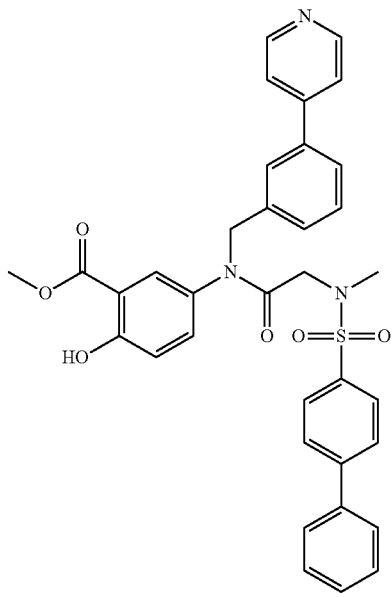 [SMILES: COC(=O)c1cc(N(Cc2cccc(-c3ccncc3)c2)C(=O)CN(C)S(=O)(=O)c2ccc(-c3ccccc3)cc2)ccc1O]

Methyl 2-hydroxy-5-(2-(N-methylbiphenyl-4-ylsulfonamido)-N-(3-(pyridin-4-yl)benzyl)acetamido)-benzoate (8x). This was obtained as a solid (0.050 g, 27%) from acid 7c (0.096 g, 0.313 mmol) and amine 6f (0.100 g, 0.299 mmol) in the same manner as described for 8a. $^1$H NMR (400 MHz, CDCl$_3$) δ 10.88 (s, 1H), 8.67-8.57 (m, 2H), 7.83 (d, J=8.4 Hz, 1H), 7.66-7.65 (m, 3H), 7.61-7.51 (m, 5H), 7.51-7.32 (m, 8H), 7.24 (d, J=7.7 Hz, 1H), 7.08 (dd, J=8.8, 2.7 Hz, 1H), 6.98 (d, J=8.8 Hz, 1H), 4.88 (s, 2H), 3.92 (s, 3H), 3.78 (s, 2H), 2.98 (s, 3H).

Synthesis of Carboxylic Acids 9

General Protocol: Methyl ester 8 (0.1 mmol) was dissolved in THF (2 ml) and 2M NaOH (excess) was added. The resultant biphasic mixture was refluxed overnight and then acidified to pH 2 with 4N HCl. The precipitated solids were collected by filtration and dried to afford the desired acids in 70-80% yields.

5-(N-Benzyl-2-(N-benzyl-4-methylphenylsulfonamido)acetamido)-2-hydroxybenzoic acid (9a). A mixture of 8a (0.107 g, 0.107 mmol) in THF (2 mL) and sodium hydroxide (aq. 1 M, 2 mL) was refluxed overnight. The solvent was then removed under reduced pressure. The resulting solid was slurried in HCl(aq. 4 M), filtered, washed with HCl and dried under vacuum to afford 9a as a solid (0.046 g, 79%). $^1$H NMR (400 MHz, DMSO-d$_6$) δ 7.69 (d, J=8 Hz, 2H), 7.36 (d, J=8 Hz, 2H), 7.26-7.16 (m, 7H), 7.15 (m, 2H), 7.05 (m, 2H), 6.70 (m, 1H), 6.57 (m, 1H), 4.63 (s, 2H), 4.42 (s, 2H), 2.55 (s, 2H), 2.38 (s, 3H); HPLC 99.58% (t$_R$=9.3 min, 60% acetonitrile in water); HRMS (ESI-ve) m/z calcd for C$_{30}$H$_{27}$N$_2$O$_6$S 543.15953 [M-H]$^-$, found 543.15962; LC-MS (ESI-ve) 543.16.

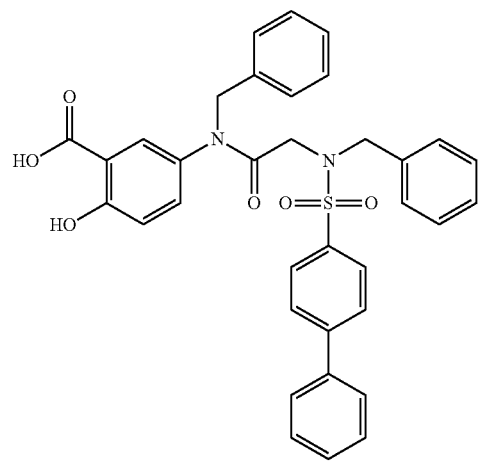 [SMILES: O=C(O)c1cc(N(Cc2ccccc2)C(=O)CN(Cc2ccccc2)S(=O)(=O)c2ccc(-c3ccccc3)cc2)ccc1O]

5-(N-Benzyl-2-(N-benzylbiphenyl-4-ylsulfonamido)acetamido)-2-hydroxybenzoic acid (9b). This was obtained as a solid (0.054 g, 92%) from 8b (0.060 g, 0.097 mmol) in the same manner as described for 9a. $^1$H NMR (400 MHz, DMSO-d$_6$) δ 7.87 (q, J=8 Hz, 4H), 7.75 (d, J=8 Hz, 2H), 7.51 (t, J=8 Hz, 2H), 7.44 (m, 1H), 7.33-7.18 (m, 9H), 7.05 (d, J=8 Hz, 2H), 6.72-6.50 (m, 2H), 4.63 (s, 2H), 4.49 (s, 2H), 3.65 (s, 1H); HPLC 99.95% (t$_R$=17.8 min, 60% acetonitrile in water); HRMS (ESI-ve) calcd for C$_{35}$H$_{29}$N$_2$O$_6$S 605.17518 [M-H]$^-$, found 605.17545; LC-MS (ESI) 605.18.

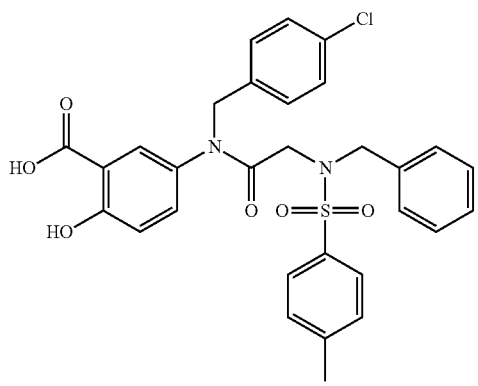 [SMILES: Cc1ccc(S(=O)(=O)N(CC(=O)N(Cc2ccc(Cl)cc2)c2ccc(O)c(C(=O)O)c2)Cc2ccccc2)cc1]

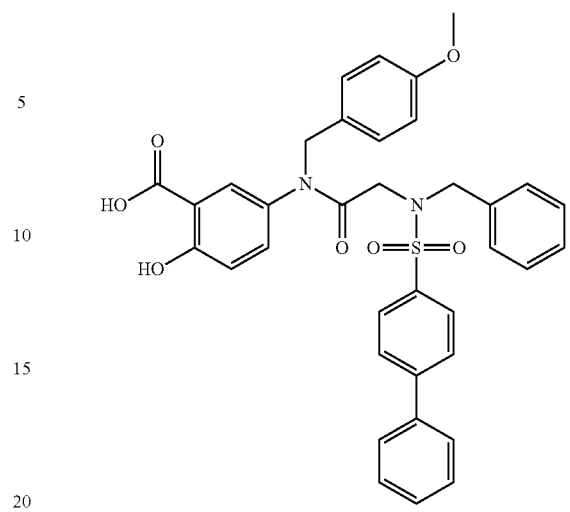

5-(2-(N-Benzyl-4-methylphenylsulfonamido)-N-(4-chlorobenzyl)acetamido)-2-hydroxybenzoic acid (9c). This was obtained as a solid (0.050 g, mmol, 86%) from 8c (0.060 g, 0.101 mmol) in the same manner as described for 9a. $^1$H NMR (400 MHz, DMSO-d$_6$) δ 7.68 (d, J=8 Hz, 2H), 7.36-7.25 (m, 8H), 7.16 (m, 2H), 7.08 (d, J=8 Hz, 2H), 6.67 (m, 1H), 6.55 (m, 1H), 4.61 (s, 2H), 4.42 (s, 2H), 3.58 (s, 2H), 3.35 (s, 3H); HPLC 99.96% (t$_R$=8.9 min, 60% acetonitrile in water); HRMS (ESI-ve) calcd for C$_{30}$H$_{26}$ClN$_2$O$_6$S 577.12056 [M−H]$^-$, found 577.12096; LC-MS (ESI-ve) 577.11.

5-(2-(N-Benzylbiphenyl-4-ylsulfonamido)-N-(4-methoxybenzyl)acetamido)-2-hydroxybenzoic acid (9f). This was obtained as a solid (0.054 g, 92%) from 8f (0.060 g, 0.092 mmol) in the same manner as described for 9a. $^1$H NMR (400 MHz, DMSO-d$_6$) δ 7.87 (m, 1H), 7.76 (m, 2H), 7.52 (m, 2H), 7.44 (m, 1H), 7.28-7.25 (m, 4H), 7.18 (m, 2H), 6.93 (d, J=8 Hz, 2H), 6.74 (d, J=8 Hz, 2H), 6.56 (m, 1H), 6.49 (m, 1H), 4.54 (s, 2H), 4.51 (s, 2H), 3.65 (s, 3H), 3.60 (s, 2H); HPLC 97.98% (t$_R$=16.51 min, 60% acetonitrile in water); HRMS (ESI-ve): calcd for C$_{36}$H$_3$,N$_2$O$_7$S 635.18575 [M−H]$^-$, found 635.18566; LC-MS (ESI-ve) 635.138.

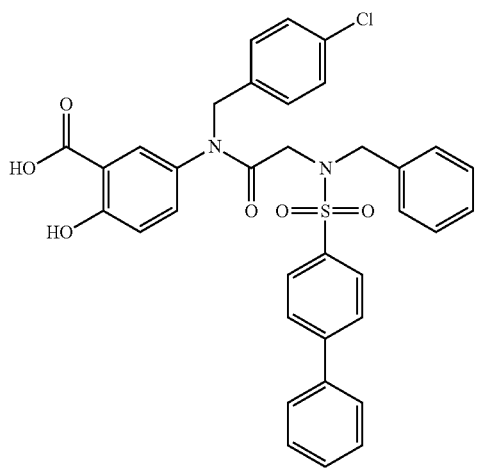 [SMILES: O=C(O)c1cc(N(Cc2ccc(Cl)cc2)C(=O)CN(Cc2ccccc2)S(=O)(=O)c2ccc(-c3ccccc3)cc2)ccc1O]

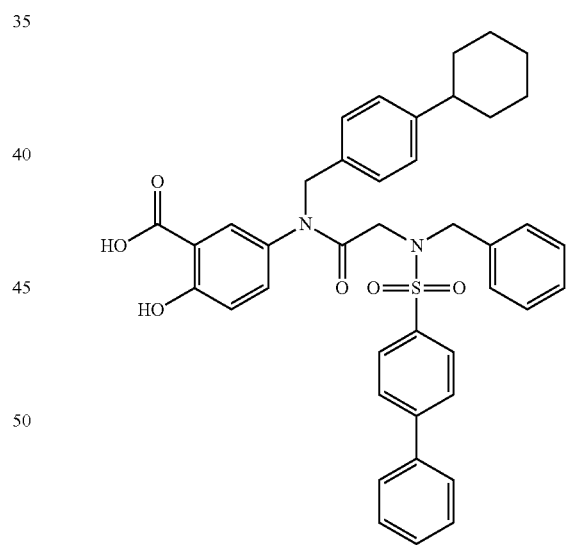

5-(2-(N-Benzylbiphenyl-4-ylsulfonamido)-N-(4-chlorobenzyl)acetamido)-2-hydroxybenzoic acid (9d). This was obtained as a solid (0.052 g, mmol, 88%) from 8d (0.060 g, 0.092 mmol) in the same manner as described for 9a. $^1$H NMR (400 MHz, DMSO-d$_6$) δ 7.86 (q, J=8 Hz, 4H), 7.75 (d, J=8 Hz, 2H), 7.51 (t, J=8 Hz, 2H), 7.45 (m, 1H), 7.30-7.26 (m, 6H), 7.19 (m, 2H), 7.1 (d, J=8 Hz, 2H), 6.70 (m, 1H), 6.57 (m, 1H), 4.61 (s, 2H), 4.49 (s, 2H), 3.65 (s, 2H); HPLC 98.96% (t$_R$=9.9 min, 70% acetonitrile in water); HRMS (ESI-ve) calcd for C$_{35}$H$_{28}$ClN$_2$O$_6$S 639.13621 [M−H]$^-$, found 639.13644; LC-MS (ESI-ve) 639.13.

5-(2-(N-Benzylbiphenyl-4-ylsulfonamido)-N-(4-cyclohexylbenzyl)acetamido)-2-hydroxybenzoic acid (9g). This was obtained as a solid (69%) from 8g (0.100 g) in the same manner as described for 9a. $^1$H NMR (400 MHz, DMSO-d$_6$) δ 7.89 (m, 4H), 7.76 (m, 2H), 7.53-7.44 (m, 3H), 7.32-7.18 (m, 4H), 7.0 (d, J=8 Hz, 2H), 6.90 (d, J=8 Hz, 2H), 6.80 (m, 1H), 6.65 (m, 1H), 4.57 (s, 2H), 4.53 (s, 2H), 3.65 (s, 3H), 2.36 (m, 1H), 1.72-1.68 (m, 6H), 1.29-1.25 (m, 4H); HPLC 99.10% (t$_R$=7.32 min, 80% acetonitrile in water); HRMS (ESI-ve) calcd for C$_{41}$H$_{40}$N$_2$O$_6$S 687.25343 [M−H]$^-$, found 635.25259; LC-MS (ESI) 687.26.

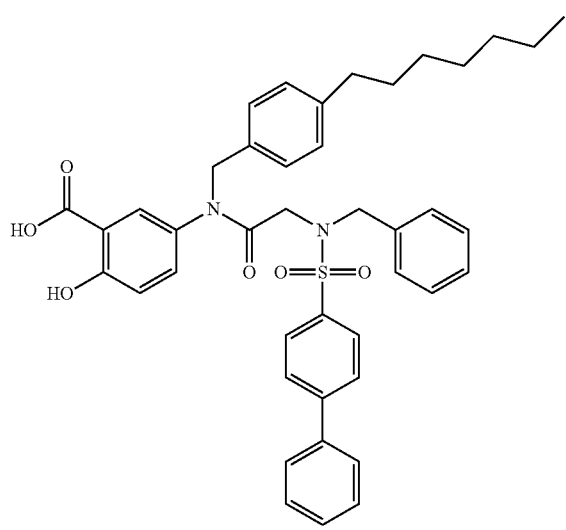 [SMILES: CCCCCCCc1ccc(CN(C(=O)CN(Cc2ccccc2)S(=O)(=O)c2ccc(-c3ccccc3)cc2)c2ccc(O)c(C(=O)O)c2)cc1]

5-(2-(N-Benzylbiphenyl-4-ylsulfonamido)-N-(4-heptylbenzyl)acetamido)-2-hydroxybenzoic acid (9h). This was obtained as a solid (0.058 g) from 8h in the same manner as described for 9a. $^1$H NMR: (400 MHz, DMSO-d$_6$) δ 7.87 (m, 4H), 7.76 (m, 2H), 7.52-7.41 (m, 3H), 7.24-7.08 (m, 5H), 6.99 (d, J=8 HZ, 2H), 6.91 (d, J=8 Hz, 2H), 6.73 (m, 1H), 6.59 (m, 1H), 4.58 (s, 2H), 4.51 (s, 2H), 3.64 (s, 2H), 2.44 (m, 2H), 1.46 (m, 2H), 1.21 (m, 8H), 0.82 (t, J=8 Hz, 3H); HPLC purity 97.82% (t$_R$=7.97 min, 90% acetonitrile in water); HRMS (ESI+ve) Calcd for C$_{42}$H$_{45}$N$_2$O$_6$S 705.29928 [M+H]$^+$, found 705.29862; Calcd for C$_{42}$H$_{44}$N$_2$O$_6$SNa 727.28123 [M+Na], found 727.28083; LC-MS (ESI+ve) 705.32.

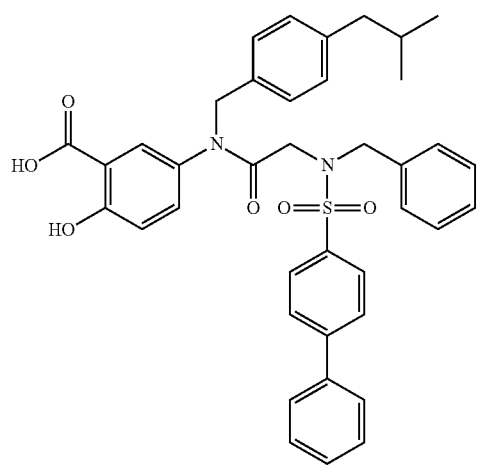 [SMILES: CC(C)Cc1ccc(CN(C(=O)CN(Cc2ccccc2)S(=O)(=O)c2ccc(-c3ccccc3)cc2)c2ccc(O)c(C(=O)O)c2)cc1]

5-(2-(N-Benzylbiphenyl-4-ylsulfonamido)-N-(4-isobutylbenzyl)acetamido)-2-hydroxybenzoic acid (9i). This was obtained as a solid (0.050 g) from 8i in the same manner as described for 9a. $^1$H NMR (400 MHz, DMSO-d$_6$) δ 7.87 (m, 4H), 7.76 (m, 2H), 7.53-7.41 (m, 3H), 7.28-7.17 (m, 6H), 6.95 (dd, J=8, 24 Hz, 4H), 6.59 (m, 1H), 6.48 (m, 1H), 4.57 (s, 1H), 4.52 (s, 1H), 3.62 (s, 1H), 2.33 (d, J=4 Hz, 2H), 1.71 (m, 1H), 0.79 (s, 3H), 0.77 (s, 3H); HPLC 98.27% (t$_R$=7.89 min, 80% acetonitrile in water); HRMS (ESI) Calcd for C$_{39}$H$_{39}$N$_2$O$_6$S 663.25233 [M+H]$^+$, found 663.25210; Calcd for C$_{39}$H$_{38}$N$_2$O$_6$SNa 685.23428 [M+Na], found 685.23256; LC-MS (ESI) 663.27.

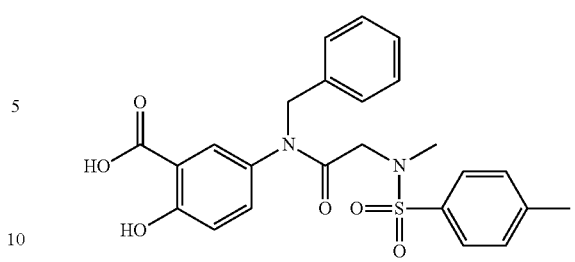

5-(N-Benzyl-2-(N,4-dimethylphenylsulfonamido)acetamido)-2-hydroxybenzoic acid (9j). This was obtained as a solid (0.030g, 78%) from 8j (0.040 g, 0.083 mmol) in the same manner as described for 9a. $^1$H NMR (400 MHz, DMSO-d$_6$) δ 7.52 (m, 3H), 7.36-7.24 (m, 6H), 7.15 (m, 2H), 6.96 (m, 2H), 4.76 (s, 2H), 3.70 (s, 2H), 2.78 (s, 3H), 2.37 (s, 3H); HPLC 99.45% (t$_R$=10.98 min, 50% acetonitrile in water); HRMS (ESI-ve) Calcd for C$_{24}$H$_{24}$N$_2$O$_6$S 467.12823, [M-H]$^-$, found 467.12914; LC-MS (ESI-ve) 469.15.

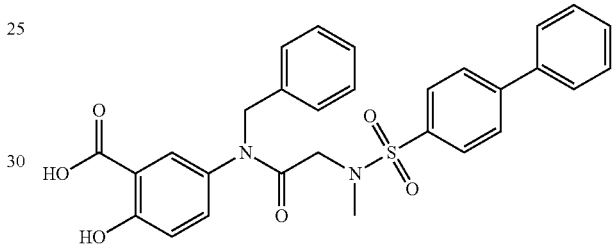

5-(N-Benzyl-2-(N-methylbiphenyl-4-ylsulfonamido)acetamido)-2-hydroxybenzoic acid (9k). This was obtained as a solid (0.034 g, 0.064 mmol, 87%) from 8k (0.040 g, 0.074 mmol) in the same manner as described for 9a. $^1$H NMR (400 MHz, DMSO-d$_6$) δ 7.84-7.71 (m, 6H), 7.51-7.42 (m, 4H), 7.32-7.22 (m, 4H), 7.15 (m, 2H), 6.97 (m, 1H), 4.76 (s, 2H), 3.79 (s, 2H), 2.86 (s, 3H); HPLC 96.06% (t$_R$=7.93 min, 60% acetonitrile in water); HRMS (ESI-ve) Calcd for C$_{29}$H$_{25}$N$_2$O$_6$S 529.14388 [M-H]$^-$, found 529.14508; LC-MS (ESI+ve) 531.17.

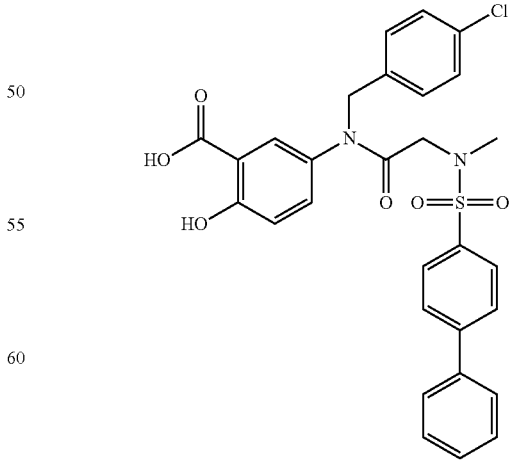

5-(N-(4-Chlorobenzyl)-2-(N-methylbiphenyl-4-ylsulfonamido)acetamido)-2-hydroxybenzoic acid (9l). This was obtained as a solid from 8l (0.060 g, 0.104 mmol) in the same manner as described for 9a. $^1$H NMR (400 MHz, DMSO-d$_6$) δ 7.83 (d, J=8 Hz, 2H), 7.73-7.70 (m, 4H), 7.51-7.42 (m, 3H), 7.30 (m, 2H), 7.15 (d, J=8 Hz, 2H), 7.08 (m, 1H), 6.78 (d, J=8 Hz, 2H), 4.70 (s, 1H), 3.75 (s, 2H), 2.84 (s, 3H); HPLC purity 94.5% (t$_R$=6.97 min, 65% acetonitrile in water); HRMS (ESI+ve) Calcd for C$_{29}$H$_{25}$ClN$_2$O$_6$S 565.11946 [M+H]$^+$, found 565.11781; Calcd for C$_{29}$H$_{24}$ClN$_2$O$_6$SNa [M+Na] 587.10141, found 587.10001.

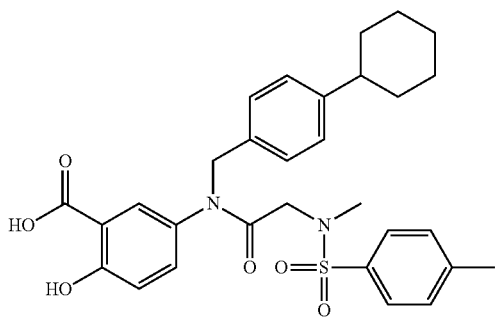 [SMILES: Cc1ccc(S(=O)(=O)N(C)CC(=O)N(Cc2ccc(C3CCCCC3)cc2)c2ccc(O)c(C(=O)O)c2)cc1]

5-(N-(4-Cyclohexylbenzyl)-2-(N,4-dimethylphenylsulfonamido)acetamido)-2-hydroxybenzoic acid (9m). This was obtained as a solid (80%) from (0.030 g, 0.053 mmol) in the same manner as described for 9a. $^1$H NMR (400 MHz, DMSO-d$_6$) δ 7.51 (d, J=8 Hz, 2H), 7.45 (d, J=4 Hz, 1H), 7.33 (d, J=8 Hz, 2H), 7.24 (dd, J=4, 8 Hz, 1H), 7.11 (d, J=8 Hz, 2H), 7.02 (d, J=8 Hz, 2H), 6.91 (d, J=8 Hz, 1H), 4.68 (s, 2H), 3.66 (s, 2H), 2.75 (s, 3H), 2.42 (m, 1H), 2.35 (s, 3H), 1.73 (m, 5H), 1.33-121 (m, 5H); HPLC purity 97.8% (t$_R$=8.83 min, 70% acetonitrile in water); HRMS (ESI-ve): Calcd for C$_{30}$H$_{33}$N$_2$O$_6$S 549.20648 [M-H]$^-$, found 549.20724; LC-MS (ESI-ve) 549.21.

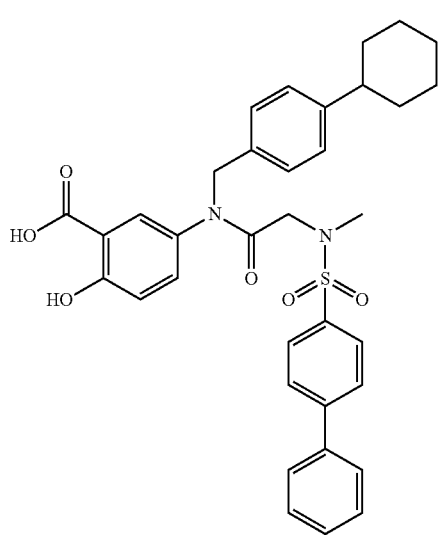 [SMILES: CN(CC(=O)N(Cc1ccc(C2CCCCC2)cc1)c1ccc(O)c(C(=O)O)c1)S(=O)(=O)c1ccc(-c2ccccc2)cc1]

5-(N-(4-Cyclohexylbenzyl)-2-(N-methylbiphenyl-4-ylsulfonamido)acetamido)-2-hydroxybenzoic acid (9n). This was obtained as a solid from 8n (0.045 g, 0.0719 mmol) in the same manner as described for 9a. $^1$H NMR (400 MHz, DMSO-d$_6$) δ 7.85 (d, J=8 Hz, 2H), 7.74 (m, 4H), 7.53-7.44 (m, 4H), 7.25 (dd, J=4, 8 Hz, 1H), 7.07 (d, J=8 Hz, 2H), 6.97 (d, J=8 Hz, 2H), 6.93 (d, J=8 Hz, 1H), 4.68 (s, 2H), 3.77 (s, 2H), 2.87 (s, 3H), 2.40 (m, 1H), 1.74-1.69 (m, 5H), 1.31-1.50 (m, 5H); HPLC 93.41% (t$_R$=14.74 min, 70% acetonitrile in water); HRMS (ESI-ve) Calcd for C$_{35}$H$_{35}$N$_2$O$_6$S 611.22213 [M-H], found 611.22258; LC-MS (ESI) 611.23.

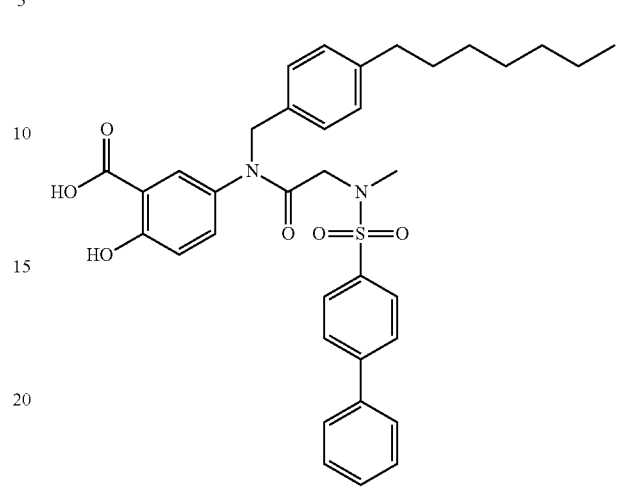

5-(N-(4-Heptylbenzyl)-2-(N-methylbiphenyl-4-ylsulfonamido)acetamido)-2-hydroxybenzoic acid (9o). This was obtained as a solid from 8o (0.050 g) in the same manner as described for 9a. $^1$H NMR (400 MHz, DMSO-d$_6$) δ 7.84 (d, J=8 Hz, 2H), 7.70 (m, 4H), 7.51-7.42 (m, 4H), 7.12-6.98 (m, 5H), 6.81 (d, J=8 Hz, 1H), 4.67 (s, 2H), 3.75 (s, 2H), 2.85 (s, 3H), 2.45 (m, 2H), 1.47 (m, 2H), 1.21 (m, 8H), 0.82 (t, J=8 Hz, 3H); HPLC 96.5% (t$_R$=10.72 min, 80% acetonitrile in water); HRMS (ESI+ve) Calcd for C$_{36}$H$_4$,N$_2$O$_6$S [M+H]$^1$ 629.26798, found 629.26692; Calcd for C$_{36}$H$_{40}$N$_2$O$_6$S [M+Na] 651.24993, found 651.24895; LC-MS (ESI) 629.28.

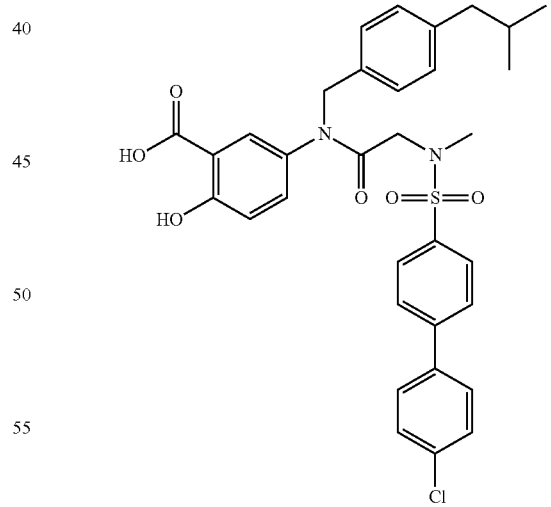

5-(2-(4'-Chloro-N-methylbiphenyl-4-ylsulfonamido)-N-(4-isobutylbenzyl)acetamido)-2-hydroxybenzoic acid (9p). This was obtained as a solid (0.040 g) from 8p (0.050 g, 0.079 mmol) in the same manner as described for 9a. $^1$H NMR (400 MHz, DMSO-d$_6$) δ 7.84 (d, J=8 Hz, 2H), 7.75 (m, 4H), 7.55 (d, J=8 Hz, 2H), 7.41 (d, J=4 Hz, 1H), 7.05 (dd, J=4, 8 Hz, 1H), 6.97 (M, 4H), 6.76 (d, J=8 Hz, 1H), 4.65 (s, 2H), 3.74 (s, 2H), 2.86 (s, 3H), 2.34 (d, J=8 Hz, 2H), 1.72

(m, 1H), 0.79 (s, 3H), 0.78 (s, 3H); HPLC purity 99.10% ($t_R$=6.01 min, 80% acetonitrile in water); HRMS (ESI+ve): Calcd for $C_{33}H_{34}ClN_2O_6S$ 621.18206 [M+H]$^+$, found 621.18084; Calcd for $C_{33}H_{33}ClN_2O_6SNa$ 643.16401 [M+Na]$^+$, found 643.16841; LC-MS (ESI+ve) 621.02.

NMR (400 MHz, DMSO-$d_6$) δ 7.84 (d, J=8 Hz, 2H), 7.74 (m, 4H), 7.55 (d, J=8 Hz, 2H), 7.43 (d, J=4 Hz, 1H), 7.0 (m, 4H), 6.78 (d, J=8 Hz, 2H), 4.63 (s, 2H), 3.72 (s, 2H), 3.67 (s, 3H), 2.84 (s, 3H); HPLC 96.31% ($t_R$=11.31 min, 60% acetonitrile in water); HRMS (ESI-ve) Calcd for $C_{30}H_{26}ClN_2O_6S$ 593.11547 [M-H]$^-$, found 593.11538; LC-MS (ESI-ve) 593.11.

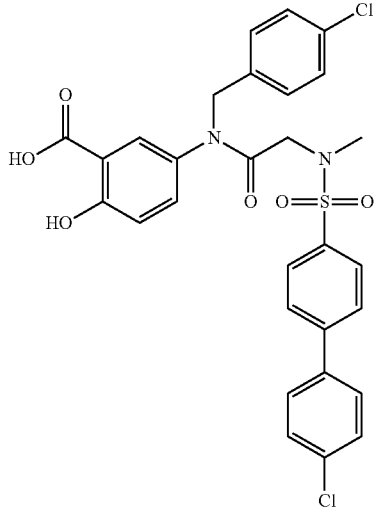 [SMILES: CN(CC(=O)N(Cc1ccc(Cl)cc1)c1ccc(O)c(C(=O)O)c1)S(=O)(=O)c1ccc(-c2ccc(Cl)cc2)cc1]

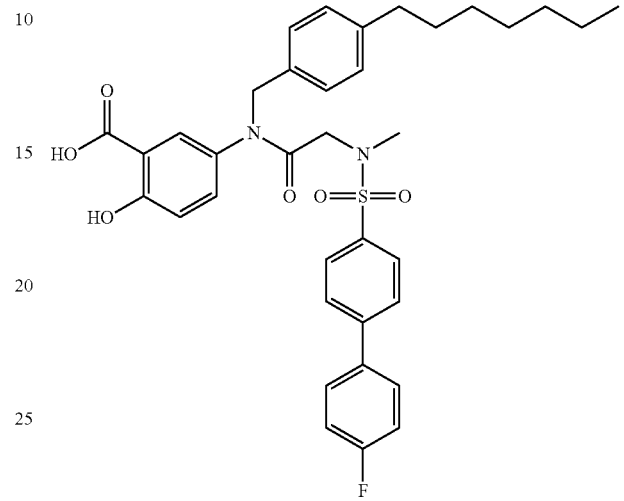

5-(2-(4'-Chloro-N-methylbiphenyl-4-ylsulfonamido)-N-(4-chlorobenzyl)acetamido)-2-hydroxybenzoic acid (9q). This was obtained as a solid (0.043 g, 73%) from 8q (0.060 g, 0.98 mmol) in the same manner as described for 9a. $^1$H NMR (400 MHz, DMSO-$d_6$) δ 7.83 (m, 2H), 7.74 (m, 4H), 7.55 (d, J=8 Hz, 2H), 7.44 (d, J=4H, 1H), 7.30 (d, J=8 Hz, 2H), 7.14 (d, J=8 Hz, 2H), 7.03 (dd, J=8, 4 Hz, 1H), 6.74 (d, J=8 Hz, 1H), 4.69 (s, 2H), 3.74 (s, 2H), 2.84 (s, 3H); HPLC purity 94.8% ($t_R$=17.33 min, 60% acetonitrile in water); HRMS (ESI-ve) Calcd for $C_{29}H_{23}ClN_2O_6S$ 597.06594 [M-H], found 597.06616; LC-MS (ESI-ve) 597.07.

5-(2-(4'-Fluoro-N-methylbiphenyl-4-ylsulfonamido)-N-(4-heptylbenzyl)acetamido)-2-hydroxybenzoic acid (9s). This was obtained as a solid from 8s (0.080 g) in the same manner as described for 9a. $^1$H NMR (400 MHz, DMSO-$d_6$) δ 7.83-7.71 (m, 6H), 7.45 (d, J=4 Hz, 1H), 7.33 (m, 2H), 7.04-6.97 (m, 5H), 6.75 (d, J=8 Hz, 1H), 4.66 (s, 2H), 3.74 (s, 2H), 2.85 (s, 3H), 1.41 (m, 2H), 1.22 (m, 10H), 0.83 (m, 3H); HPLC purity 95.05% ($t_R$=7.3 min, 60% acetonitrile in water); HRMS (ESI-ve) Calcd for $C_{36}H_{38}FN_2O_6S$ 645.24401 [M-H], found 645.24325; LC-MS (ESI-ve) 645.23.

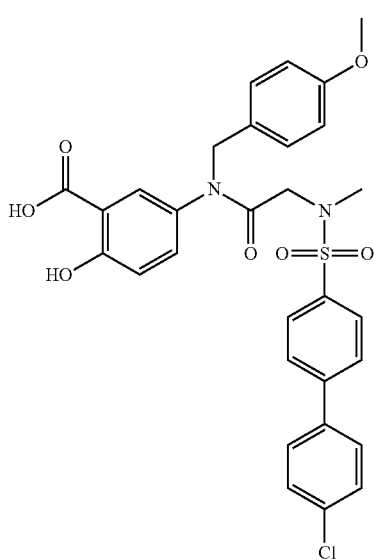 [SMILES: COc1ccc(CN(C(=O)CN(C)S(=O)(=O)c2ccc(-c3ccc(Cl)cc3)cc2)c2ccc(O)c(C(=O)O)c2)cc1]

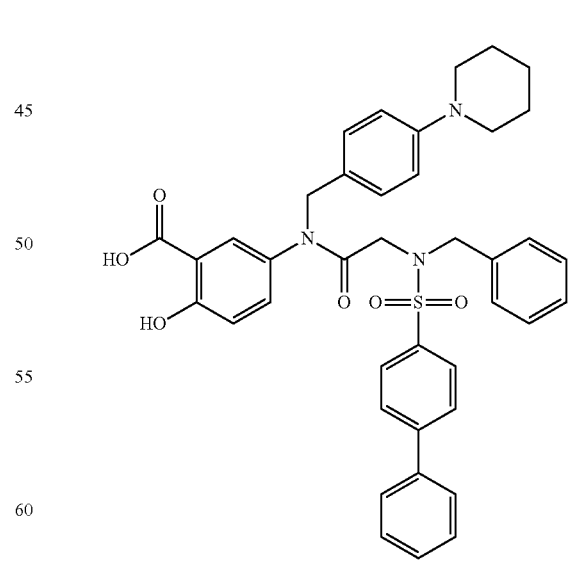

5-(2-(4'-Chloro-N-methylbiphenyl-4-ylsulfonamido)-N-(4-methoxybenzyl)acetamido)-2-hydroxybenzoic acid (9r). This was obtained as a solid (0.035 g, 60%) from 8r (0.060 g, 0.099 mmol) in the same manner as described for 9a. $^1$H 5-(2-(N-Benzylbiphenyl-4-ylsulfonamido)-N-(4-(piperidin-1-yl)benzyl)acetamido)-2-hydroxybenzoic acid (9t). This was obtained as a solid (0.050 g) from 8t in the same manner as described for 9a. $^1$H NMR (400 MHz, DMSO-d6)

δ 7.91-7.86 (m, 4H), 7.77-7.75 (m, 2H), 7.53-7.49 (m, 2H), 7.47-7.42 (m, 1H), 7.32-7.26 (m, 4H), 7.21-7.15 (m, 2H), 6.95-6.91 (m, 1H), 6.81-6.78 (m, 3H), 6.73 (d, J=8.4 Hz, 2H), 4.52 (s, 2H), 4.51 (s, 2H), 3.63 (s, 2H), 3.01-2.98 (m, 4H), 1.72-1.34 (m, 6H). HPLC purity 71.7% ($t_R$=2.753 min, 65% acetonitrile in water); HRMS (ESI–ve) Calcd for $C_{40}H_{40}N_3O_6S$ 690.2632 [M+H]$^+$, found 690.2638.

2H), 7.44 (t, J=7.3 Hz, 1H), 7.32 (d, J=2.7 Hz, 1H), 7.29-7.23 (m, 3H), 7.21-7.17 (m, 2H), 6.95 (dd, J=8.7, 2.7 Hz, 1H), 6.82 (dd, J=8.7, 2.4 Hz, 4H), 6.71 (d, J=8.7 Hz, 2H), 4.53 (s, 4H), 3.68-3.65 (m, 2H), 3.64 (s, 2H), 2.97-2.90 (m, 4H). HPLC purity 92.1% ($t_R$=7.94 min, 50% acetonitrile in water); HRMS (ESI–ve) Calcd for $C_{39}H_{36}N_3O_7S$ 690.2279 [M–H], found 690.2278.

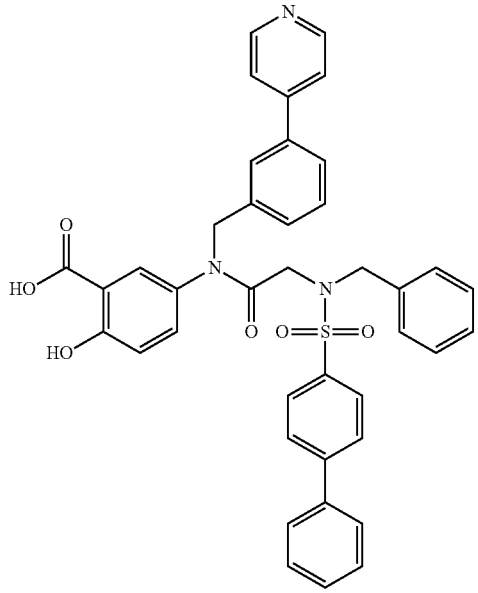 [SMILES: O=C(O)c1cc(N(Cc2cccc(-c3ccncc3)c2)C(=O)CN(Cc2ccccc2)S(=O)(=O)c2ccc(-c3ccccc3)cc2)ccc1O]

5-(2-(N-Benzylbiphenyl-4-ylsulfonamido)-N-(3-(pyridin-4-yl)benzyl)acetamido)-2-hydroxybenzoic acid (9u). This was obtained as a solid (0.050 g) from 8u in the same manner as described for 9a. $^1$H NMR (400 MHz, DMSO-d6) δ 8.67 (d, J=6.3 Hz, 2H), 7.90 (d, J=8.5 Hz, 2H), 7.83-7.77 (m, 4H), 7.73-7.68 (m, 4H), 7.64-7.41 (m, 15H), 7.27-7.17 (m, 6H), 7.12 (d, J=2.7 Hz, 1H), 6.85 (d, J=8.8 Hz, 1H), 4.78 (s, 2H), 4.46 (s, 2H), 3.65 (s, 2H). HPLC purity 95.7% ($t_R$=3.96 min, 60% acetonitrile in water); HRMS (ESI–ve) Calcd for $C_{40}H_{34}N_3O_6S$ 684.2162 [M+H]$^+$, found 684.2163.

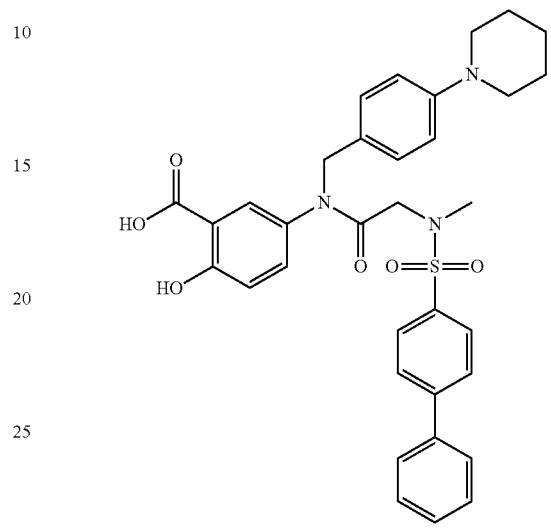

2-Hydroxy-5-(2-(N-methylbiphenyl-4-ylsulfonamido)-N-(4-(piperidin-1-yl)benzyl)acetamido)benzoic acid (9w). This was obtained as a solid (0.050 g) in the same manner as described for 9a. $^1$H NMR (400 MHz, DMSO-d6) δ 7.84 (m, 3H), 7.75-7.67 (m, 4H), 7.56-7.40 (m, 4H), 7.26 (d, J=7.2 Hz, 1H), 7.06-6.94 (m, 4H), 4.65 (s, 2H), 3.75 (s, 2H), 3.14 (s, 4H), 2.85 (s, 3H), 1.64-1.52 (m, 6H). HPLC purity 98.3% ($t_R$=13.5 min, 40% acetonitrile in water); HRMS (ESI–ve) Calcd for $C_{34}H_{34}N_3O_6S$ 614.2319 [M–H]$^-$, found 614.2305.

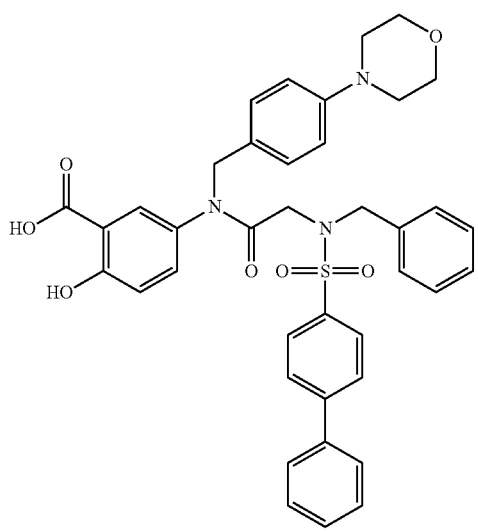 [SMILES: O=C(O)c1cc(N(Cc2ccc(N3CCOCC3)cc2)C(=O)CN(Cc2ccccc2)S(=O)(=O)c2ccc(-c3ccccc3)cc2)ccc1O]

5-(2-(N-Benzylbiphenyl-4-ylsulfonamido)-N-(4-morpholinobenzyl)acetamido)-2-hydroxybenzoic acid (9v). This was obtained as a solid (0.056 g) from 8v in the same manner as described for 9a. $^1$H NMR (400 MHz, DMSO-d6) δ 7.91-7.86 (s, 4H), 7.77 (d, J=7.4 Hz, 1H), 7.52 (t, J=7.5 Hz, 2-Hydroxy-5-(2-(N-methylbiphenyl-4-ylsulfonamido)-N-(3-(pyridin-4-yl)benzyl)acetamido)benzoic acid (9x).

This was obtained as a solid from 8x (0.050 g) in the same manner as described for 9a. $^1$H NMR (400 MHz, DMSO-d6) δ 8.65 (d, J=6.2 Hz, 2H), 7.83-7.78 (m, 1H), 7.76-7.67 (m, 8H), 7.64-7.57 (m, 3H), 7.53-7.41 (m, 5H), 7.37 (dd, J=8.7, 2.8 Hz, 1H), 7.30 (d, J=7.7 Hz, 1H), 6.97 (d, J=8.8 Hz, 1H), 4.86 (s, 2H), 3.81 (s, 3H), 2.83 (s, 4H). HPLC purity 95.30% ($t_R$=11.9 min, 40% acetonitrile in water); HRMS (ESI-ve) Calcd for $C_{34}H_{28}N_3O_6S$ 608.1849 [M-H]$^-$, found 608.1832.

Synthesis of Diethyl Phosphonylanilines 25

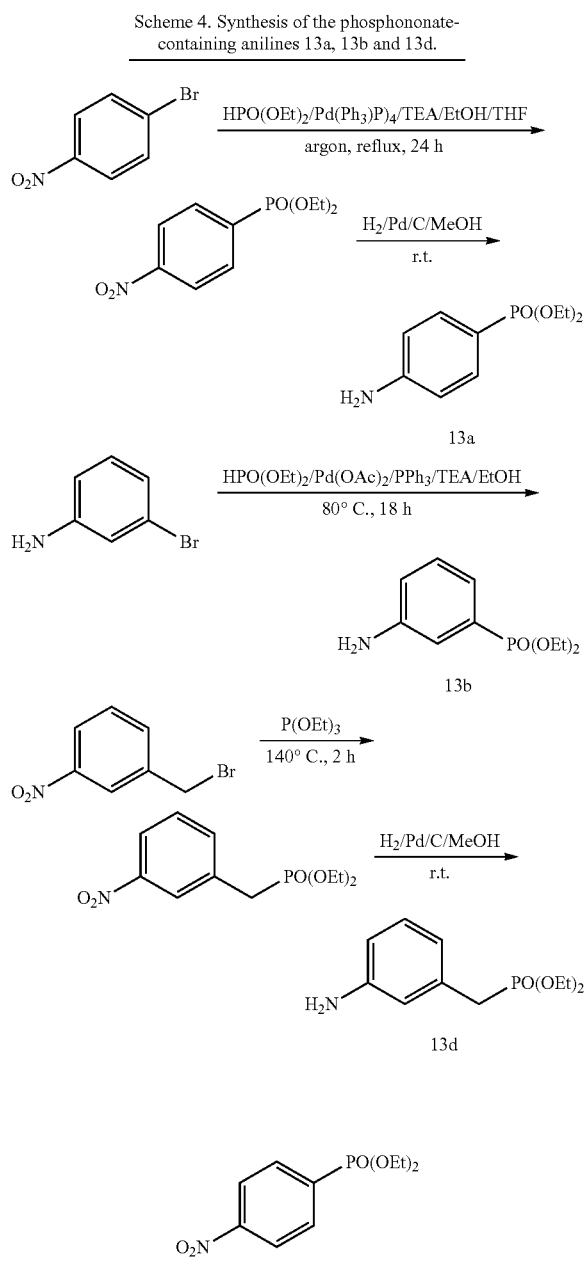

Diethyl 4-nitrophenylphosphonate. 1-bromo-4-nitrobenzene (2.02 g, 10 mmol) was suspended in EtOH (10 ml) and THF (5 ml) was added to afford a homogeneous solution. The solution was degassed, a vacuum applied to the flask, which was then filled with argon. This process was repeated 3 times. The catalyst Pd(Ph$_3$P)$_4$ (0.578 g, 0.5 mmol) was added under argon atmosphere and the mixture was again degassed, a vacuum applied to the flask which was then refilled with argon. Triethylamine (2.8 ml, 20 mmol) and diethyl phosphite (1.93 ml, 15 mmol) were added via syringe. The resulting solution was refluxed for 24 h under argon and cooled to room temperature. The insoluble material was filtered and the filtrate concentrated to provide the crude product which was dissolved in EtOAc (50 ml) and filtered. The residue was washed with EtOAc (2×25 ml) The combined filtrates were concentrated and the crude product was purified via flash chromatography (50 silica gel, DCM/CH$_3$OH gradient) affording diethyl 4-nitrophenylphosphonate (3.44 g, containing ca. 14% diethyl phosphite in weight) as a yellow oil. $^1$H NMR (400 MHz, CDCl$_3$) δ 8.33-8.28 (m, 2H), 8.04-7.97 (m, 2H), 4.25-4.07 (m, 4H), 1.34 (t, J=7.1 Hz, 6H). LC-MS (ESI+) m/z 204.01 (M+H-2×C$_2$H$_4$)$^+$; HRMS (ESI+) m/z calculated for C$_{10}$H$_{15}$NO$_5$P (M+H)$^+$ 260.0682, found 260.0679.

Diethyl 4-aminophenylphosphonate (13a). Diethyl 4-nitrophenylphosphonate (1.700 g, containing ca. 14% diethyl phosphite) was dissolved in methanol (20 ml) and was stirred in the presence of Pd (10% on carbon, 0.100g) under H$_2$ (balloon) at room temperature for 14 h. The Pd/C was filtered through a pad of celite. The filtrate was concentrated to dryness affording the title compound 13a (1.200 g, 80%) as a brown solid. $^1$H NMR (400 MHz, CDCl$_3$) δ 7.63-7.54 (m, 2H), 6.76-6.70 (m, 2H), 4.16-3.96 (m, 4H), 3.81 (br s, 2H), 1.30 (2t, J=7.5 Hz, 6H). LC-MS (ESI+) m/z 174.04 (M+H-2×C$_2$H$_4$)$^+$; HRMS (ESI+) m/z calculated for C$_{10}$H$_{17}$NO$_3$P (M+H)$^+$ 230.0941, found 230.0936.

Diethyl 3-aminophenylphosphonate (13b). Anhydrous EtOH (10 mL), 3-bromoaniline (3.16 g, 18.36 mmol), diethyl phosphite (3.11 g, 22.53 mmol), and anhydrous Et$_3$N (3.9 mL) were added under Argon at room temperature to a round-bottom flask previously charged with Pd(OAc)$_2$ (0.245 g, 1.09 mmol) and PPh$_3$ (0.764 g, 2.91 mmol). The reaction mixture was stirred at 80° C. (oil bath temperature) for 18 h. The solvent was removed under reduced pressure to provide a yellow oil. Flash chromatography (SiO$_2$) afforded 13b as a yellow oil (1.54 g, 35%). $^1$H NMR (400 MHz, CDCl$_3$) δ 7.25-7.21 (m, 1H), 7.18-7.09 (m, 2H), 6.86-6.82 (m, 1H), 4.30-3.99 (m, 4H), 1.40-0.97 (m, 6H). LC-MS (ESI+ve) m/z found 230.2.

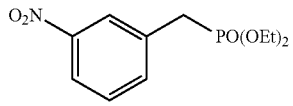

Diethyl 3-nitrobenzylphosphonate. 3-nitrobenzyl bromide (1.080g, 5.00 mmol) was mixed with triethyl phosphite (1.04 ml, 6.00 mmol). The mixture was heated to 140° C. in an oil bath for 2 h and cooled to room temperature. The excess of triethyl phosphite and the byproduct ethyl bromide were evaporated in vacuo to provide diethyl 3-nitrobenzylphosphonate as a yellow oil (1.460 g, 100%) which did not require further purification. $^1$H NMR (400 MHz, CDCl$_3$) δ 8.17-8.14 (m, 1H), 8.14-8.10 (m, 1H), 7.69-7.62 (m, 1H), 7.50 (t, J=7.9 Hz, 1H), 4.09-4.02 (m, 4H), 3.23 (d, J=21.8 Hz, 2H), 1.26 (t, J=7.1 Hz, 6H). LC-MS (ESI+) m/z 218.02 (M+H-2×C$_2$H$_4$)$^+$; HRMS (ESI+) m/z calculated for C$_{11}$H$_{17}$NO$_5$P (M+H)$^+$ 274.0839, found 274.0843.

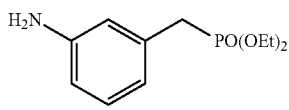

Diethyl 3-aminobenzylphosphonate (13d). Diethyl 3-nitrobenzylphosphonate (1.366 g, 5.00 mmol) was dissolved in THF (5 ml). The solution was hydrogenated with Pd/C (10%, 0.100 g) catalyst under H$_2$ atmosphere at room temperature overnight. The catalyst was filtered off through a pad of celite and washed with THF (5 ml×2). The filtrate was concentrated to dryness affording the aniline 13c (1.300g, 100%) as yellow oil which was used without further purification.

Compounds 14

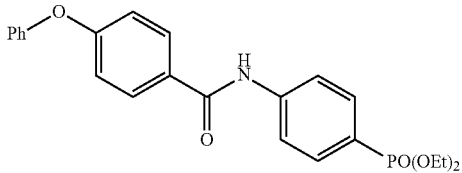

Diethyl 4-(4-phenoxybenzamido)phenylphosphonate (14a). This compound was synthesized according to the procedure used to prepare 14c using 4-phenoxybenzoic acid (0.214 g, 1 mmol), 13a (0.229 g, 1 mmol), EDC (0.211 g, 1.1 mmol) and DMAP (0.012g, 0.1 mmol) in DCM (5 ml). The reaction mixture was concentrated and the residue suspended in EtOAc (50 ml) and washed with HCl (1 N, 3×10 ml), water (2×10 ml) and brine (10 ml). The organic phase was dried over Na$_2$SO$_4$ and concentrated to give the crude product. Flash chromatography (SiO$_2$, DCM/CH$_3$OH gradient) afforded the title compound 14a (0.180 g, 42%) as a yellow oil. $^1$H NMR (400 MHz, CDCl$_3$) δ 7.96 (s, 1H), 7.89-7.85 (m, 2H), 7.85-7.74 (m, 4H), 7.43-7.37 (m, 2H), 7.23-7.18 (m, 1H), 7.10-7.03 (m, 4H), 4.20-4.01 (m, 4H), 1.34-1.30 (m, 6H). LC-MS (ESI+) m/z 426.15 (M+H)$^+$; HRMS (ESI+) m/z calculated for C$_{23}$H$_{25}$NO$_5$P (M+H)$^+$ 426.1465, found 426.1458.

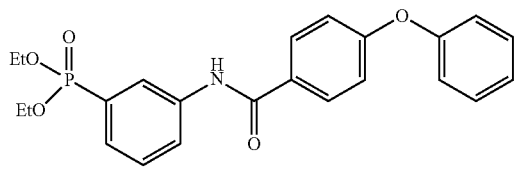 [SMILES: CCOP(=O)(OCC)c1cccc(NC(=O)c2ccc(Oc3ccccc3)cc2)c1]

Diethyl 3-(4-phenoxybenzamido)phenylphosphonate (14b). Anhydrous DCM (2 mL) was added at 0° C. under Argon to a round-bottom flask previously charged with 13b (0.504 g, 2.20 mmol), 4-phenoxybenzoic acid (0.364 g, 1.69 mmol), DMAP (0.035 g, 0.286 mmol), EDC hydrochloride (0.399 g, 2.08 mmol). The reaction mixture was first allowed to warm up to room temperature without removing the ice-bath and then stirred at room temperature overnight. HCl (aq., 1M, 20 mL) was added, the organic layer extracted with DCM (2×20 mL), separated, dried (Na$_2$SO$_4$), filtered and the solvent removed under reduced pressure. Chromatography (SiO$_2$) afforded 14b as a yellow solid (0.643 g, 1.51 mmol, 90%). $^1$H NMR (400 MHz, CDCl$_3$) δ 8.84-8.71 (m, 1H), 8.29 (s, 1H), 8.03-7.88 (m, 3H), 7.52-7.45 (m, 2H), 7.44-7.36 (m, 2H), 7.23-7.17 (m, 1H), 7.08-7.06 (m, 4H), 4.07-3.99 (m, 4H), 1.40-1.13 (m, 6H). HRMS (ESI+ve) m/z calculated for C$_{23}$H$_{25}$N$_2$O$_5$P (M+H)$^+$ 426.1464, found 426.1458.

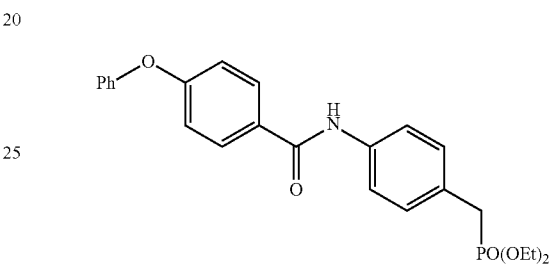

Diethyl 4-(4-phenoxybenzamido)benzylphosphonate (14c). 1-Ethyl-3-(3-dimethylaminopropyl) carbodiimide (0.211 g, 1.1 mmol) and DMAP (0.012 g, 0.1 mmol) were added sequentially to a cooled mixture (0° C.) of 4-phenoxybenzoic acid (0.243 g, 1 mmol) and diethyl 4-aminobenzylphosphonate (Acros Organic)(0.214 g, 1 mmol) in DCM (5 ml). The mixture was stirred at room temperature for 16 h and concentrated. The residue was slurried in HCl (1 N, 20 ml) and sonicated. The solid was isolated by filtration, washed with water (3×10 ml) and dried under vacuum to afford the title compound 14c (0.423 g, 96%) as a white solid. m.p. 144-146° C. $^1$H NMR (400 MHz, CDCl$_3$) δ 8.02 (br s, 1H), 7.89-7.84 (m, 2H), 7.60 (d, J=8.5 Hz, 2H), 7.42-7.37 (m, 2H), 7.31-7.26 (m, 2H), 7.22-7.17 (m, 1H), 7.09-7.02 (m, 4H), 4.06-3.94 (m, 4H), 3.13 (d, J=21.4 Hz, 2H), 1.24 (t, J=7.1 Hz, 6H). $^{31}$P NMR (162 MHz, CDCl$_3$) δ 27.38. LC-MS (ESI+) m/z 440.17 (M+H)$^+$; HRMS (ESI+) m/z calculated for C$_{24}$H$_{27}$NO$_5$P (M+H)$^+$ 440.1621, found 440.1625.

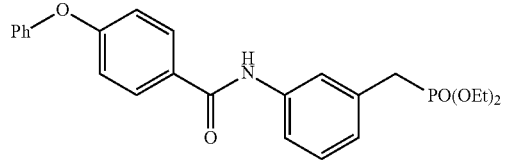

Diethyl 3-(4-phenoxybenzamido)benzylphosphonate (14d). This compound was synthesized according to the procedure used to prepare 14c using 4-phenoxybenzoic acid (0.0.428 g, 2 mmol), 13d (0.600 g, 2.5 mmol), EDC (0.383 g, 2 mmol) and DMAP (0.024 g, 0.2 mmol) in DCM (5 ml). The workup and purification procedure was following that for 14a affording the title compound 14d (0.860 g, 98%) as colorless oil. $^1$H NMR (400 MHz, CDCl$_3$) δ 7.91 (br s, 1H), 7.88-7.83 (m, 2H), 7.68 (d, J=7.4 Hz, 1H), 7.53 (d, J=1.8 Hz, 1H), 7.44-7.36 (m, 2H), 7.31 (t, J=7.8 Hz, 1H), 7.22-7.16 (m, 1H), 7.10-7.02 (m, 5H), 4.08-3.97 (m, 4H), 3.16 (d, J=21.6 Hz, 2H), 1.25 (t, J=7.1 Hz, 6H). LC-MS (ESI+) m/z 440.20 (M+H)⁺; HRMS (ESI+) m/z calculated for $C_{24}H_{27}NO_5P$ (M+H)⁺ 440.1621, found 440.1628.

Compound 15

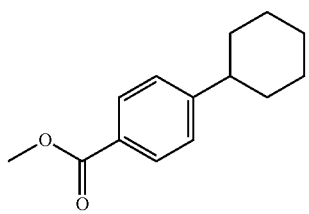 [SMILES: COC(=O)c1ccc(C2CCCCC2)cc1]

Methyl 4-cyclohexylbenzoate. 4-Cyclohexylbenzoic acid (3.94 g, 18.28 mmol) in MeOH (35 mL) was refluxed under Argon for 40 h in presence of $H_2SO_4$ (conc., 0.40 mL). The reaction mixture was concentrated and $NaHCO_3$ (aq., sat., 100 mL) added to the residue. The mixture was extracted with EtOAc (100 mL×2). The organic phase was dried over $Na_2SO_4$ and concentrated to give methyl 4-cyclohexylbenzoate (4.014 g, 96%) as a white solid. ¹H NMR (400 MHz, CDCl₃) δ 7.95 (d, J=8.4 Hz, 1H), 7.27 (d, J=8.4 Hz, 1H), 3.89 (s, 2H), 2.66-2.39 (m, 1H), 1.92-1.72 (m, 5H), 1.52-1.18 (m, 5H).

(4-Cyclohexylphenyl)methanol. Methyl 4-cyclohexylbenzoate (3.934 g, 18.04 mmol) in anhydrous THF (10 mL) was added dropwise to a suspension of LiAlH₄ (1.693 g, 44.55 mmol) in anhydrous THF (15 mL) under Argon at 0° C. The reaction mixture was first allowed to warm up to room temperature and then stirred at room temperature for 16 h. The reaction mixture was then cooled to 0° C. and sodium sulfate decahydrate (20 g) was added portionwise, followed by the addition of Et₂O (160 mL). The formed solid was filtered, washed with Et₂O (3×30 mL). The organic extracts were combined, washed with water (2×100 mL), separated, dried (Na₂SO₄), filtered and the solvent removed under reduced pressure to provide (4-cyclohexylphenyl)methanol (2.908 g, 85%) as a white solid. ¹H NMR (400 MHz, CDCl₃) δ 7.29 (d, J=8.2 Hz, 2H), 7.21 (d, J=8.1 Hz, 2H), 4.64 (s, 2H), 2.53-2.49 (m, 1H), 1.90-1.70 (m, 5H), 1.50-0.99 (m, 5H).

1-(Bromomethyl)-4-cyclohexylbenzene (15). Supported triphenylphosphine PS-Ph₃P (1 g, 2 mmol) was added to (4-cyclohexylphenyl)methanol (0.190 g, 1 mmol) in DCM (10 ml). After 30 min, CBr₄ (0.332 g, 1 mmol) was added. The mixture was shaken at room temperature for 16 h and filtered. The resin was washed with DCM and the combined filtrates were concentrated to dryness affording the title compound 15 (0.260 g, 100%) as a colorless oil. ¹H NMR (400 MHz, CDCl₃) δ 7.31 (d, J=8.1 Hz, 2H), 7.17 (d, J=8.2 Hz, 2H), 4.49 (s, 2H), 2.54-2.43 (m, 1H), 1.91-1.70 (m, 5H), 1.46-1.15 (m, 5H).

Compounds 16

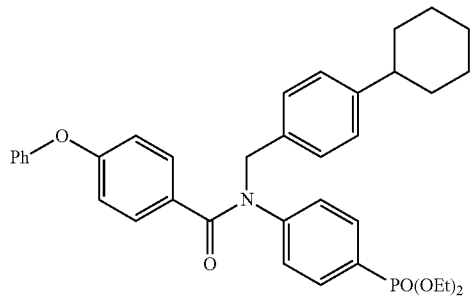

Diethyl 4-(N-(4-cyclohexylbenzyl)-4-phenoxybenzamido)phenylphosphonate (16a). This compound was prepared, according to the procedure used to make 16d, from 14a (0.115 g, 0.27 mmol), NaH (0.011 g, 0.27 mmol), 15 (0.076 g, 0.3 mmol) affording the title compound 16a (0.041 g, 25%) as a colorless oil and the starting 14a (0.041 g, 36%) was recovered. ¹H NMR (400 MHz, CDCl₃) δ 7.61 (dd, J=12.9, 8.1 Hz, 2H), 7.37-7.29 (m, 4H), 7.20 (d, J=7.9 Hz, 2H), 7.16-7.10 (m, 3H), 7.04 (dd, J=8.1, 3.5 Hz, 2H), 6.99-6.94 (m, 2H), 6.75 (d, J=8.4 Hz, 2H), 5.11 (s, 2H), 4.16-3.98 (m, 4H), 2.53-2.40 (m, 1H), 1.90-1.70 (m, 5H), 1.45-1.30 (m, 5H), 1.27 (t, J=7.1 Hz, 6H). LC-MS (ESI+) m/z 598.27 (M+H)¹; HRMS (ESI+) m/z calculated for $C_{36}H_{41}NO_5P$ (M+H)⁺ 598.2717, found 598.2711.

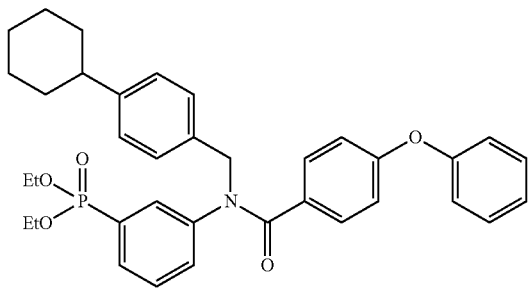

Diethyl 3-(N-(4-cyclohexylbenzyl)-4-phenoxybenzamido)phenylphosphonate (16b). Compound 14b (0.256 g, 0.602 mmol) was added to a suspension of NaH (0.029 g, 0.727 mmol, 60% dispersion in mineral oil) in anhydrous THF (0.6 mL) under Argon at 0° C. The reaction mixture was stirred at 0° C. under Argon for 1 h, followed by the addition of a solution of 15 (0.175 g, 0.694 mmol) in anhydrous THF (0.6 mL). After stirring at room temperature overnight, the reaction mixture was quenched with aq. HCl (1 M, 5 mL) and extracted with DCM (5 mL x 2). The

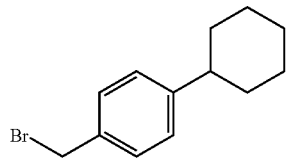 [SMILES: BrCc1ccc(C2CCCCC2)cc1]

organic layers were combined, dried (Na₂SO₄), filtered and the solvent removed under reduced pressure. Chromatography (SiO₂) afforded 16b as a yellow oil (0.124 g, 0.207 mmol, 35%). ¹H NMR (400 MHz, CDCl₃) δ 8.05 (d, J=8.1 Hz, 1H), 7.58 (dd, J=12.8, 7.5 Hz, 1H), 7.40 (t, J=7.8 Hz, 1H), 7.34-7.28 (m, 4H), 7.22-7.18 (m, 3H), 7.14-7.06 (m, 3H), 7.00 (d, J=8.1 Hz, 1H), 6.92 (d, J=8.0 Hz, 1H), 6.74 (d, J=8.7 Hz, 2H), 5.10 (s, 2H), 3.97-3.89 (m, 2H), 3.85-3.78 (m, 2H), 2.47-2.47 (m, 1H), 1.82-1.61 (m, 5H), 1.41-1.31 (m, 4H) 1.25-1.18 (m, 7H). HRMS (ESI+ve) m/z calculated for $C_{36}H_{41}N_2O_5P$ (M+H)⁺ 598.2716, found 598.2721.

CDCl₃) δ 7.35-7.29 (m, 4H), 7.20 (d, J=8.2 Hz, 2H), 7.14-7.07 (m, 5H), 6.96-6.92 (m, 2H), 6.88 (d, J=7.9 Hz, 2H), 6.74-6.69 (m, 2H), 5.06 (s, 2H), 3.99-3.80 (m, 4H), 3.04 (d, J=21.7 Hz, 2H), 2.50-2.39 (m, 1H), 1.88-1.69 (m, 5H), 1.44-1.19 (m, 5H), 1.16 (t, J=7.1 Hz, 6H). ³¹P NMR (162 MHz, CDCl₃) δ 26.90. LC-MS (ESI+) m/z 612.29 (M+H)⁺; HRMS (ESI+) m/z calculated for $C_{37}H_{43}NO_5P$ (M+H)⁺ 612.2873, found 612.2855.

Compounds 17

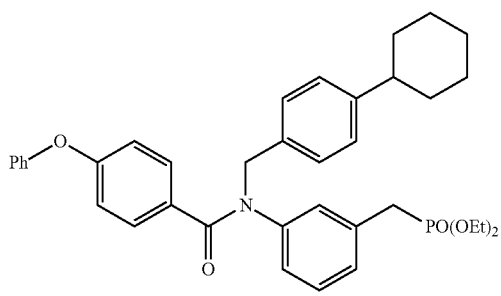

Diethyl 3-(N-(4-cyclohexylbenzyl)-4-phenoxybenzamido)benzylphosphonate (16c). This compound was prepared, according to the procedure used to make 16d, from 14c (0.439 g, 1 mmol), NaH (0.04 g, 1 mmol), 15 (0.253 g, 1 mmol) affording the title compound 16c (0.441 g, 72%) as a colorless oil. ¹H NMR (400 MHz, CDCl₃) δ 7.36-7.28 (m, 4H), 7.21 (d, J=8.1 Hz, 2H), 7.14-7.03 (m, 5H), 7.01 (s, 1H), 6.96-6.90 (m, 2H), 6.79-6.69 (m, 3H), 5.07 (s, 2H), 3.99-3.80 (m, 4H), 3.01 (d, J=21.7 Hz, 2H), 2.48-2.42 (m, 1H), 1.83-1.71 (m, 5H), 1.45-1.22 (m, 5H). LC-MS (ESI+) m/z 612.29 (M+H)⁺; HRMS (ESI+) m/z calculated for $C_3H_{43}NO_5P$ (M+H)⁺ 612.2873, found 612.2872.

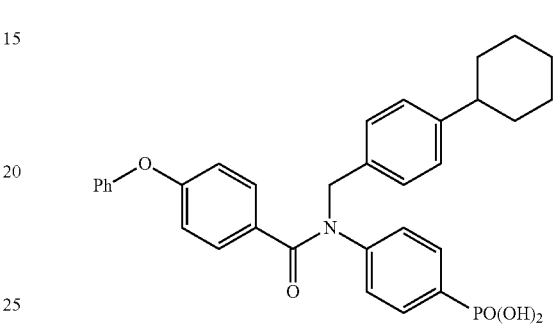

4-(N-(4-Cyclohexylbenzyl)-4-phenoxybenzamido)phenylphosphonic acid (17a). This compound was prepared, according to the procedure used to make 17c, from 16a (0.030 g, 0.05 mmol) and bromotrimethylsilane (0.1 ml, 0.5 mmol) in DCM (3 ml) affording the title compound 17a (0.015 mg, 56%) as a white solid. m.p. 182.7° C. (dec.). ¹H NMR (400 MHz, CD₃OD) δ 7.62 (dd, J=12.8, 8.3 Hz, 2H), 7.40-7.30 (m, 4H), 7.20-7.11 (m, 7H), 6.94 (d, J=7.8 Hz, 2H), 6.76 (d, J=8.7 Hz, 2H), 5.14 (s, 2H), 2.51-2.40 (m, 1H), 1.90-1.70 (m, 5H), 1.49-1.20 (m, 5H). LC-MS (ESI−) m/z 540.20 (M−H)⁻; HRMS (ESI−) m/z calculated for $C_{32}H_3NO_5P$ (M−H)⁻ 540.1945, found 540.1935.

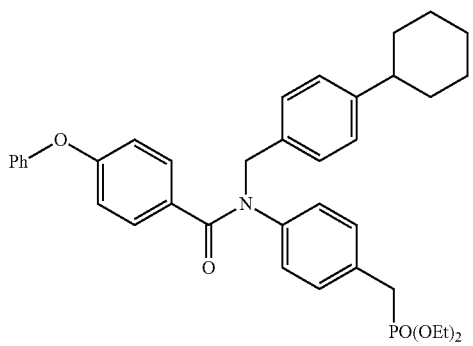

Diethyl 4-(N-(4-cyclohexylbenzyl)-4-phenoxybenzamido)benzylphosphonate (16d). Sodium hydride (60% in mineral oil, 0.012 g, 0.3 mmol) was suspended in THF (3 ml) and the mixture cooled to 0° C. The phosphonate 14c (0.132 g, 0.3 mmol) was added and the mixture stirred at 0° C. for 1 h. The alkyl bromide 15 (0.091 g, 0.36 mmol) was then added and the mixture was stirred at room temperature for 16 h. The reaction mixture was diluted with EtOAc (30 ml) and washed with water (2×10 ml) and brine (10 ml). The organic phase was dried over Na₂SO₄ and concentrated. The crude product was purified via flash chromatography (SiO₂, DCM/CH₃OH gradient) affording the title compound 16d (0.126 g, 69%) as a colorless oil. ¹H NMR (400 MHz, 3-(N-(4-cyclohexylbenzyl)-4-phenoxybenzamido)phenylphosphonic acid (17b). This was prepared from the amide 16b (0.119 g, 0.199 mmol) in a similar manner as described for 18b. The obtained crude material was slurried with hexane/EtOAc (9/1, 1 ml), filtered, washed with hexane (1 mL), dried under vacuum to afford pure 17b as an off-white solid (0.059 g, 0.108 mmol, 55%). m.p 92.3-94.9° C. ¹H NMR (400 MHz, CD₃OD) δ 7.59-7.44 (m, 2H), 7.38-7.25 (m, 5H), 7.21-7.09 (m, 6H), 6.93 (d, J=8.0 Hz, 2H), 6.74 (d, J=8.4 Hz, 2H), 5.11 (s, 2H), 2.47-2.42 (m, 1H), 1.81-1.71 (m, 5H), 1.41-1.23 (m, 5H). HRMS (ESI+ve) m/z calculated for $C_{32}H_{33}N_2O_5P$ (M+H)⁺ 542.2090, found 542.2084.

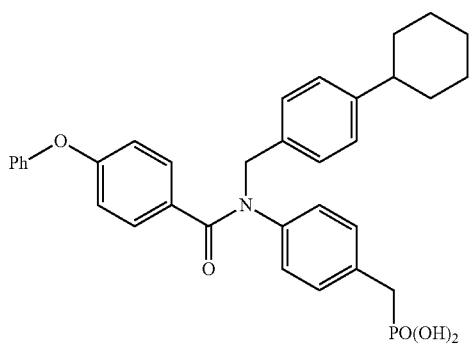

4-(N-(4-Cyclohexylbenzyl)-4-phenoxybenzamido)benzylphosphonic acid (17c). TMSBr (0.216 ml, 1.63 mmol) was added to a solution of 16c (0.100 g, 0.163 mmol) in DCM (3 ml) at 0° C. The mixture was stirred at room temperature for 4 h and concentrated. The residue was stirred with 90% CH$_3$OH/H$_2$O (10 ml) at room temperature for 1 h and concentrated. The crude product was slurried in acetone (2 ml) and filtered. The solid was washed with acetone (2×1 ml) and dried affording the title compound 17c (0.046 g, 51%) as an off-white solid. m.p. 188° C. (dec.). $^1$H NMR (400 MHz, CD$_3$OD) δ 7.40-7.27 (m, 4H), 7.23-7.08 (m, 7H), 6.96 (t, J=8.6 Hz, 4H), 6.75 (d, J=8.7 Hz, 2H), 5.08 (s, 2H), 3.03 (d, J=21.7 Hz, 2H), 2.54-2.40 (m, 1H), 1.92-1.70 (m, 5H), 1.51-1.21 (m, 5H). $^{31}$P NMR (162 MHz, CD$_3$OD) δ 24.54. LC-MS (ESI+) m/z 556.22 (M+H)$^+$; HRMS (ESI+) m/z calculated for C$_{33}$H$_{35}$NO$_5$P (M+H)$^+$ 556.2247, found 556.2250.

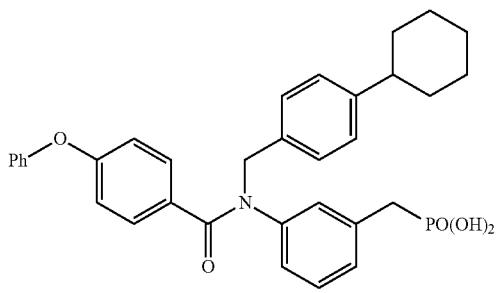

3-(N-(4-Cyclohexylbenzyl)-4-phenoxybenzamido)benzylphosphonic acid (17d). This compound was prepared, according to the procedure used to make 17c, from 16d (0.109 g, 0.18 mmol) and bromotrimethylsilane (0.24 ml, 1.78 mmol) in DCM (5 ml). Flash chromatography (SiO$_2$, DCM/CH$_3$OH gradient) afforded the title compound 17d (0.080 g, 81%) as a brown solid. m.p. 97° C. (dec.). $^1$H NMR (400 MHz, CD$_3$OD) δ 7.36-7.30 (m, 4H), 7.20 (d, J=8.1 Hz, 3H), 7.15-7.11 (m, 4H), 7.07 (t, J=7.6 Hz, 1H), 6.94 (d, J=7.9 Hz, 2H), 6.75 (d, J=8.5 Hz, 2H), 6.68 (d, J=7.4 Hz, 1H), 5.08 (s, 2H), 3.04 (d, J=21.7 Hz, 2H), 2.49-2.42 (m, 1H), 1.92-1.70 (m, 5H), 1.48-1.23 (m, 5H). LC-MS (ESI−) m/z 554.21 (M−H)$^-$; HRMS (ESI−) m/z calculated for C$_{33}$H$_{33}$NO$_5$P (M−H)$^-$ 554.2102, found 554.2088.

Compounds 18

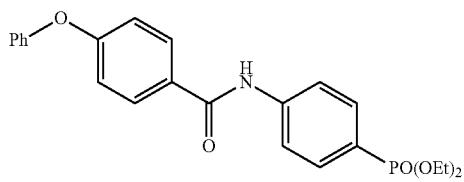

Diethyl 4-(4-phenoxybenzamido)phenylphosphonate (18a). This compound was synthesized according to the procedure used to prepare 14c using 4-phenoxybenzoic acid (0.214 g, 1 mmol), 14a (0.229 g, 1 mmol), EDC (0.211 g, 1.1 mmol) and DMAP (0.012 g, 0.1 mmol) in DCM (5 ml). The reaction mixture was concentrated and the residue suspended in EtOAc (50 ml) and washed with HCl (1 N, 3×10 ml), water (2×10 ml) and brine (10 ml). The organic phase was dried over Na$_2$SO$_4$ and concentrated to give the crude product. Flash chromatography (SiO$_2$, DCM/CH$_3$OH gradient) afforded the title compound 18a (0.180 g, 42%) as a yellow oil. $^1$H NMR (400 MHz, CDCl$_3$) δ 7.96 (s, 1H), 7.89-7.85 (m, 2H), 7.85-7.74 (m, 4H), 7.43-7.37 (m, 2H), 7.23-7.18 (m, 1H), 7.10-7.03 (m, 4H), 4.20-4.01 (m, 4H), 1.34-1.30 (m, 6H). LC-MS (ESI+) m/z 426.15 (M+H)$^+$; HRMS (ESI+) m/z calculated for C$_{23}$H$_{25}$NO$_5$P (M+H)$^+$ 426.1465, found 426.1458.

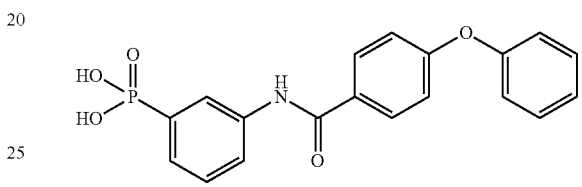

3-(4-Phenoxybenzamido)phenylphosphonic acid (18b). Bromotrimethylsilane (0.464 g, 3.03 mmol) was added dropwise under Argon to a solution of 14b (0.137 g, 0.322 mmol) in anhydrous DCM (0.5 mL). After stirring at room temperature overnight, the solvent and excess of TMS-Br were removed under reduced pressure. A mixture of MeOH/water (9/1, 2 mL) was added and the reaction mixture was stirred at room temperature for 1 h. The solvent was removed under reduced pressure to provide an orange oil. Water (10 mL) was added and the solid that precipitated was filtered, washed with water (5 mL) and dried under vacuum to afford pure 18b as an off-white solid (0.096 g, 0.260 mmol, 81%). m.p. 103.2-104.6° C. $^1$H NMR (400 MHz, CD$_3$OD) δ 8.15 (d, J=14.1 Hz, 1H), 7.95 (d, J=8.7 Hz, 2H), 7.91 (d, J=7.8 Hz, 1H), 7.59-7.57 (m, 1H), 7.52-7.46 (m, 1H), 7.42 (t, J=7.9 Hz, 2H), 7.21 (t, J=7.4 Hz, 1H), 7.08 (d, J=8.1 Hz, 2H), 7.05 (d, J=8.7 Hz, 2H). HRMS (ESI+ve) m/z calculated for C$_{19}$H$_{15}$NO$_5$P (M+H)$^+$ 370.0838, found 370.0831.

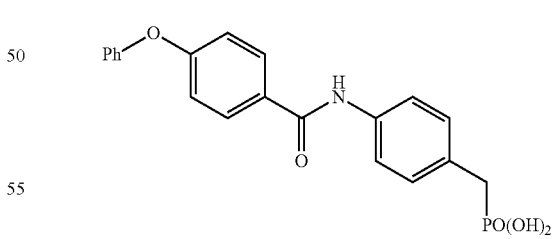

4-(4-Phenoxybenzamido)benzylphosphonic acid (18c). This compound was prepared according to the procedure used to make 17c from 14c (0.088 g, 0.2 mmol) and TMSBr (0.264 ml, 2.0 mmol). The crude product was slurried in DCM (20 ml) and filtered affording the title compound 18c (0.077 g, 100%) as a white solid. m.p.>250° C. $^1$H NMR (400 MHz, CD$_3$OD) δ 7.96-7.91 (m, 2H), 7.61 (d, J=8.1 Hz, 2H), 7.45-7.39 (m, 2H), 7.31 (dd, J=8.6, 2.5 Hz, 2H), 7.23-7.18 (m, 1H), 7.11-7.02 (m, 4H), 3.11 (d, J=21.5 Hz, 2H). $^{31}$P NMR (162 MHz, CD$_3$OD) δ 25.23. LC-MS (ESI+) m/z 384.11 (M+H)$^+$; HRMS (ESI+) m/z calculated for C$_{20}$H$_{19}$NO$_5$P (M+H)$^+$ 384.0995, found 384.0991.

Compound 19

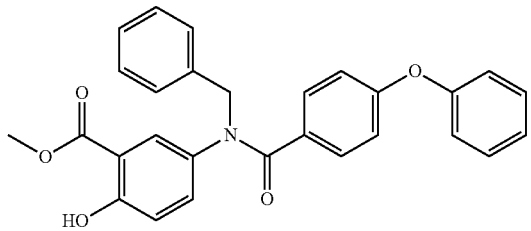 [SMILES: COC(=O)c1cc(N(Cc2ccccc2)C(=O)c2ccc(Oc3ccccc3)cc2)ccc1O]

Methyl 5-(N-benzyl-4-phenoxybenzamido)-2-hydroxybenzoate (19a). This was prepared as a yellow oil (0.301 g, 0.664 mmol, 83%) from 6a (0.205 g, 0.797 mmol) and 4-phenoxybenzoyl chloride (0.200 g, 0.862 mmol) in the same manner as described for 19g. $^1$H NMR (400 MHz, CDCl$_3$) δ 10.67 (s, 1H), 7.45 (d, J=2.5 Hz, 1H), 7.34-7.26 (m, 9H), 7.14-7.07 (m, 1H), 6.95-6.92 (m, 2H), 6.89 (dd, J=2.2, 9.1 Hz, 1H), 6.78-6.72 (m, 3H), 5.07 (s, 2H), 3.89 (s, 3H). HRMS (ESI+ve) m/z calculated for C$_{28}$H$_{24}$NO$_5$ (M+H)$^+$ 454.1649, found 454.1656.

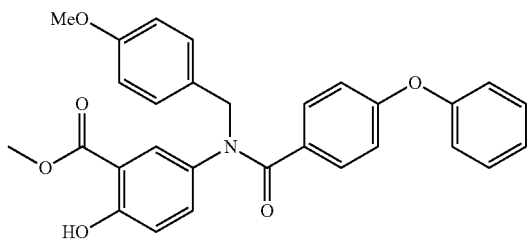 [SMILES: COC(=O)c1cc(N(Cc2ccc(OC)cc2)C(=O)c2ccc(Oc3ccccc3)cc2)ccc1O]

Methyl 2-hydroxy-5-(N-(4-methoxybenzyl)-4-phenoxybenzamido)benzoate (19b). This was prepared as a yellow oil (0.267 g, 0.552 mmol, 93%) from 6c (0.170 g, 0.592 mmol) and 4-phenoxybenzoyl chloride (0.044 g, 0.655 mmol) in the same manner as described for 19g. $^1$H NMR (400 MHz, CDCl$_3$) δ 10.68 (s, 1H), 7.43 (d, J=2.5 Hz, 1H), 7.34-7.27 (m, 4H), 7.18 (d, J=8.6 Hz, 2H), 7.15-7.08 (m, 1H), 6.96-6.90 (m, 2H), 6.86 (dd, J=1.9, 8.8 Hz, 1H), 6.81 (d, J=8.7 Hz, 2H), 6.75 (t, J=8.8 Hz, 3H), 5.00 (s, 2H), 3.90 (s, 1H), 3.78 (s, 3H). HRMS (ESI+ve) m/z calculated for C$_{29}$H$_{26}$NO$_6$ (M+H)$^+$ 484.1755, found 484.1743.

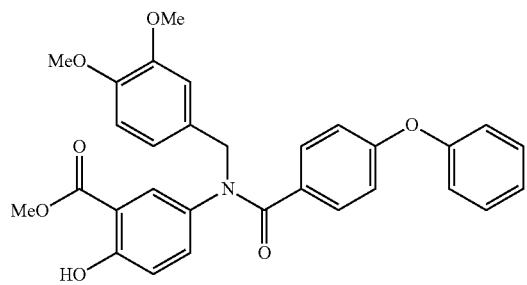 [SMILES: COC(=O)c1cc(N(Cc2ccc(OC)c(OC)c2)C(=O)c2ccc(Oc3ccccc3)cc2)ccc1O]

Methyl 2-hydroxy-5-(N-(4-methoxybenzyl)-4-phenoxybenzamido)benzoate (19c). A solution of 4-phenoxybenzoyl chloride (0.098 g, 0.422 mmol) in anhydrous THF (0.4 mL) was added to a mixture of 6k (0.113 g, 0.356 mmol), and NaHCO$_3$ (0.066 g, 0.785 mmol) in anhydrous THF (0.3 mL) at room temperature under argon overnight. The reaction mixture was quenched by the addition of NaHCO$_3$ (aq, sat, 5 mL) and extracted with EtOAc (5 mL). The organic layer was then washed HCl (aq., 1 M, 5 mL), separated, dried (Na$_2$SO$_4$) and the solvent removed under reduced pressure. Chromatography afforded 30c as a yellow oil (0.100 g, 0.194 mmol, 54%). $^1$H NMR (400 MHz, CDCl$_3$) δ 10.68 (s, 1H), 7.42 (s, 1H), 7.34-7.26 (m, 3H), 7.14-7.09 (m, 1H), 6.97-6.84 (m, 4H), 6.80-6.71 (m, 5H), 4.99 (s, 2H), 3.89 (s, 3H), 3.85 (s, 3H), 3.82 (s, 3H). HRMS (ESI+ve) m/z 514.1863 [M+H]$^+$ (calcd for C$_{30}$H$_{28}$NO$_7$ 514.1860).

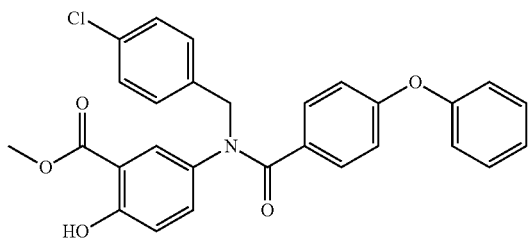

Methyl 5-(N-(4-chlorobenzyl)-4-phenoxybenzamido)-2-hydroxybenzoate (19d). This was prepared as a yellow oil (0.251 g, 0.515 mmol, 86%) from 6d (0.174 g, 0.597 mmol) and 4-phenoxybenzoyl chloride (0.152 g, 0.655 mmol) in the same manner as described for 19g. $^1$H NMR (400 MHz, CDCl$_3$) δ 10.69 (s, 1H), 7.42 (d, J=2.6 Hz, 1H), 7.36-7.18 (m, 8H), 7.15-7.08 (m, 1H), 6.94-6.92 (m, 2H), 6.89 (dd, J=8.8, 2.5 Hz, 1H), 6.78-6.75 (m, 3H), 5.02 (s, 2H), 3.90 (s, 3H). HRMS (ESI+ve) m/z calculated for C$_{28}$H$_{23}$ClNO$_5$ (M+H)$^+$ 488.1259, found 488.1261.

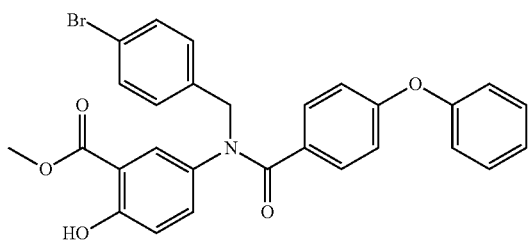 [SMILES: COC(=O)c1cc(N(Cc2ccc(Cl)cc2)C(=O)c2ccc(Oc3ccccc3)cc2)ccc1O]

Methyl 5-(N-(4-bromobenzyl)-4-phenoxybenzamido)-2-hydroxybenzoate (19e). This was prepared as a yellow oil (0.326 g, 0.612 mmol, 74%) from 6j (0.279 g, 0.830 mmol) and 4-phenoxybenzoyl chloride (0.222 g, 0.956 mmol) in the same manner as described for 19g. $^1$H NMR (400 MHz, CDCl$_3$) δ 10.69 (s, 1H), 7.43-7.39 (m, 3H), 7.35-7.27 (m, 4H), 7.18-7.08 (m, 3H), 6.95-6.92 (s, 2H), 6.89 (dd, J=8.8, 2.7 Hz, 1H), 6.7-6.75 (m, 3H), 5.01 (s, 2H), 3.90 (s, 3H). HRMS (ESI+ve) m/z calculated for C$_{28}$H$_{23}$BrNO$_5$ (M+H)$^+$ 532.0754, found 532.0674.

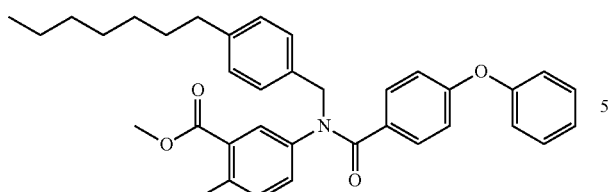

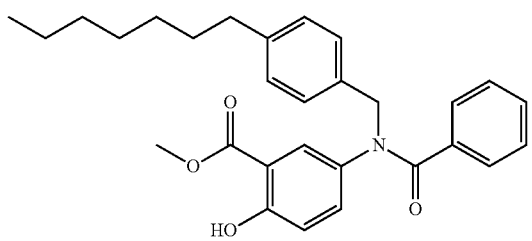 [SMILES: CCCCCCCc1ccc(CN(C(=O)c2ccccc2)c2ccc(O)c(C(=O)OC)c2)cc1]

Methyl 5-(N-(4-heptylbenzyl)-4-phenoxybenzamido)-2-hydroxybenzoate (19f). To amine 6i (0.100 g, 0.282 mmol) in CH$_2$Cl$_2$ (2 ml) was added 4-phenoxybenzoic acid (0.062 g, 0.294 mmol) and Ph$_3$PCl$_2$ (0.225 g, 0.677 mmol) under argon atmosphere. The mixture was heated at 80° C. in a microwave reactor (Biotage) for 1 h. The reaction was cooled to room temperature, diluted with CH$_2$Cl$_2$ and washed with sat. NaHCO$_3$. The organic fractions were dried (Na$_2$SO$_4$) and evaporated in vacuo. The crude mixture was purified by column chromatography to afford the amide 19f (0.130 g, 84%). $^1$H NMR (400 MHz, CDCl$_3$) δ 10.67 (s, 1H), 7.44 (d, J=2.3 Hz, 1H), 7.36-7.25 (m, 4H), 7.17 (d, J=8.0 Hz, 2H), 7.13-7.07 (m, 3H), 6.97-6.86 (m, 3H), 6.67-6.72 (m, 3H), 5.03 (s, 2H), 3.89 (s, 3H), 2.63-2.39 (m, 2H), 1.60-1.59 (m, 2H), 1.34-1.20 (m, 8H), 0.96-0.75 (m, 3H).

Methyl 5-(N-(4-heptylbenzyl)benzamido)-2-hydroxybenzoate (19h). This was prepared as a yellow oil (0.052 g, 0.119 mmol, 42%) from 6i (0.097 g, 0.284 mmol) and 4-phenoxybenzoyl chloride (0.044 g, 0.293 mmol) in the same manner as described for 19g. $^1$H NMR (400 MHz, CDCl$_3$) δ 10.63 (s, 1H), 7.42 (s, 1H), 7.31-7.28 (m, 2H), 7.25-7.16 (m, 5H), 7.09 (d, J=8.0 Hz, 2H), 6.87 (s, 1H), 6.70 (d, J=8.6 Hz, 1H), 5.00 (s, 2H), 3.88 (s, 3H), 2.56 (t, J=7.5 Hz, 2H), 1.31-1.25 (m, 10H), 0.87 (t, J=6.8 Hz, 3H). HRMS (ESI+ve) m/z calculated for C$_{29}$H$_{34}$NO$_4$ (M+H)$^+$ 460.2432, found 460.2503.

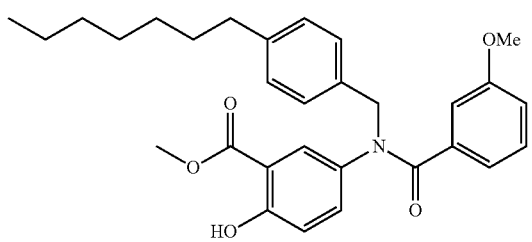 [SMILES: CCCCCCCc1ccc(CN(C(=O)c2cccc(OC)c2)c2ccc(O)c(C(=O)OC)c2)cc1]

Methyl 5-(N-(4-heptylbenzyl)-3-methoxybenzamido)-2-hydroxybenzoate (19i). This was prepared as a yellow oil (0.062 g, 0.130 mmol, 38%) from 6i (0.118 g, 0.345 mmol) and 3-methoxybenzoylchloride (0.064 g, 0.378 mmol) in the same manner as described for 19g. $^1$H NMR (400 MHz, CDCl$_3$) δ 10.65 (s, 1H), 7.42 (s, 1H), 7.17 (d, J=7.9 Hz, 2H), 7.11-7.03 (m, 3H), 6.96-6.68 (m, 5H), 5.02 (s, 2H), 3.88 (s, 3H), 3.69 (s, 3H), 2.56 (t, J=7.6 Hz, 2H), 1.31-1.25 (m, 10H), 0.87 (t, J=7.1 Hz, 3H). HRMS (ESI+ve) m/z calculated for C$_{30}$H$_{36}$NO$_5$ (M+H)$^+$ 490.2588, found 490.2580.

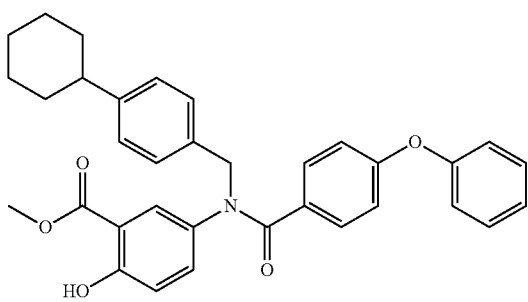

Methyl 5-(N-(4-cyclohexylbenzyl)-4-phenoxybenzamido)-2-hydroxybenzoate (19g). 4-Phenoxybenzoyl chloride (0.106 g, 0.456 mmol) was added to a mixture of 6b (0.130 g, 0.383 mmol) and NaHCO$_3$ (0.106 g, 1.26 mmol) in anhydrous THF (1.5 mL) at room temperature under Argon. After stirring at room temperature overnight, the reaction mixture was quenched with water (20 mL) and extracted with AcOEt (20 mL). The organic layer was then washed with water (20 mL), HCl(aq., 1M, 20 mL), separated, dried (Na$_2$SO$_4$), filtered and the solvent removed under reduced pressure. Chromatography (SiO$_2$) afforded 19g as a yellow oil (0.201 g, 0.375 mmol, 98%). $^1$H NMR (400 MHz, CDCl$_3$) δ 10.67 (s, 1H), 7.43 (d, J=2.9 Hz, 1H), 7.36-7.27 (m, 4H), 7.18 (d, J=8.0 Hz, 2H), 7.16-7.08 (m, 4H), 7.04-6.99 (m, 1H), 6.94 (d, J=9.6 Hz, 2H), 6.75 (t, J=8.9 Hz, 2H), 5.02 (s, 2H), 3.88 (s, 3H), 2.50-2.40 (m, 1H), 1.87-1.68 (m, 5H), 1.14-1.35 (m, 4H), 1.27-2.21 (m, 1H). HRMS (ESI+ve) m/z calculated for C$_{34}$H$_{35}$NO$_5$ (M+H)$^+$ 536.2431, found 536.2415.

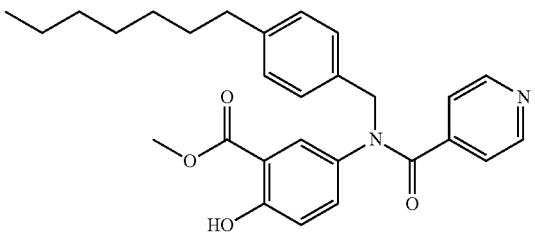 [SMILES: CCCCCCCc1ccc(CN(C(=O)c2ccncc2)c2ccc(O)c(C(=O)OC)c2)cc1]

Methyl 5-(N-(4-heptylbenzyl)isonicotinamido)-2-hydroxybenzoate (19j). This was prepared as a yellow oil (0.083 g, 0.180 mmol, 53%) from 6i (0.115 g, 0.337 mmol) and isonicotinoyl chloride hydrochloride (0.072 g, 0.404 mmol) in the same manner as described for 19g. $^1$H NMR (400 MHz, CDCl$_3$) δ 10.70 (s, 1H), 8.47 (s, 2H), 7.35 (d, J=2.7 Hz, 1H), 7.18-7.13 (m, 4H), 7.10 (d, J=8.1 Hz, 2H), 6.87 (dd, J=8.7, 2.3 Hz, 1H), 6.74 (d, J=8.9 Hz, 1H), 5.01 (s, 2H), 3.88 (s, 3H), 2.55 (t, J=7.0 Hz, 2H), 1.35-1.18 (m, 10H), 0.86 (t, J=7.1 Hz, 3H). HRMS (ESI+ve) m/z calculated for C$_{28}$H$_{33}$N$_2$O$_4$ (M+H)$^+$ 461.2434, found 461.2419.

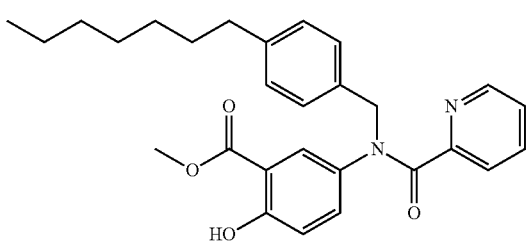 [SMILES: CCCCCCCc1ccc(CN(C(=O)c2ccccn2)c2ccc(O)c(C(=O)OC)c2)cc1]

Methyl 5-(N-(4-heptylbenzyl)picolinamido)-2-hydroxybenzoate (19k). This was prepared as a yellow oil (0.037 g, 0.080 mmol, 30%) from 6i (0.065 g, 0.269 mmol) and picolinoyl chloride hydrochloride (0.057 g, 0.320 mmol) in the same manner as described for 19g. $^1$H NMR (400 MHz, CDCl$_3$) δ 10.63 (s, 1H), 8.32 (s, 1H), 7.63-7.54 (m, 1H), 7.48-7.38 (m, 2H), 7.20 (d, J=7.8 Hz, 2H), 7.12-7.07 (m, 4H), 6.91 (dd, J=9.3, 1.9 Hz, 1H), 6.66 (d, J=8.9 Hz, 1H), 5.05 (s, 2H), 3.85 (s, 3H), 2.56 (t, J=7.8 Hz, 2H), 1.28-1.24 (m, 10H), 0.86 (t, J=7.1 Hz, 3H). HRMS (ESI+ve) m/z calculated for $C_{28}H_{33}N_2O_4$ (M+H)$^+$ 461.2434, found 461.2434.

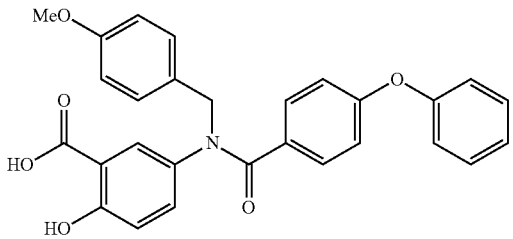

Methyl 5-(N-(4-heptylbenzyl)nicotinamido)-2-hydroxybenzoate (19l). This was prepared as a yellow oil (0.060 g, 0.130 mmol, 40%) from 6i (0.110 g, 0.322 mmol) and nicotinoyl chloride (0.057 g, 0.403 mmol) in the same manner as described for 19g. $^1$H NMR (400 MHz, CDCl$_3$) δ 10.69 (s, 1H), 8.53 (s, 1H), 7.63 (d, J=7.8 Hz, 1H), 7.41 (s, 1H), 7.15-7.08 (m, 5H), 7.09 (d, J=7.9 Hz, 2H), 6.86 (d, J=8.7 Hz, 1H), 6.73 (d, J=8.8 Hz, 1H), 5.02 (s, 2H), 3.87 (s, 3H), 2.55 (t, J=7.9 Hz, 2H), 1.27-1.24 (m, 10H), 0.86 (t, J=6.8 Hz, 3H). HRMS (ESI+ve) m/z calculated for $C_{28}H_{33}N_2O_4$ (M+H)$^+$ 461.2434, found 461.2431.

Compounds 20

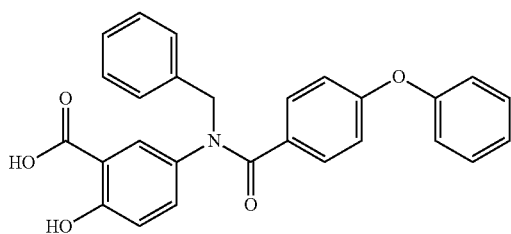 [SMILES: O=C(O)c1cc(N(Cc2ccccc2)C(=O)c2ccc(Oc3ccccc3)cc2)ccc1O]

5-(N-Benzyl-4-phenoxybenzamido)-2-hydroxybenzoic acid (20a). This was prepared as a white solid (0.155 g, 0.353 mmol, 92%) from 19a (0.174 g, 0.384 mmol) in the same manner as described for 20g. m.p.>191° C. (dec.). $^1$H NMR (400 MHz, CD$_3$OD) δ 7.46 (d, J=2.2 Hz, 1H), 7.37-7.19 (m, 9H), 7.15-7.08 (m, 1H), 6.98 (dd, J=8.7, 2.4 Hz, 1H), 6.91 (d, J=8.4 Hz, 2H), 6.78 (d, J=8.6 Hz, 2H), 6.68 (d, J=8.8 Hz, 1H), 5.09 (s, 2H). HPLC purity 96.6% {$t_R$=3.97 min, flow 1 ml/min, [(CH$_3$CN/(0.1% TFA in H$_2$O):70/30]}.HRMS (ESI-ve) m/z calculated for $C_{27}H_{20}NO_5$ (M−H)$^-$ 438.1347, found 438.1349.

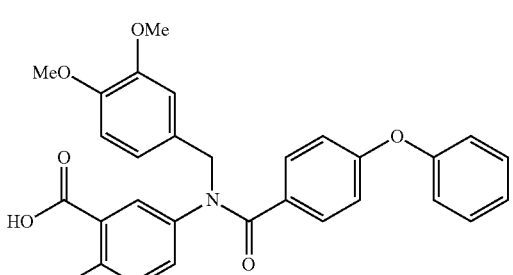

2-Hydroxy-5-(N-(4-methoxybenzyl)-4-phenoxybenzamido)benzoic acid (20b). This was prepared from 19b (0.097 g, 0.200 mmol) in the same manner as described for 20g. The crude product was slurried with methanol (1 mL), filtered and dried under vacuum to afford pure 20b as a white solid (0.035 g, 0.074 mmol, 37%). m.p. 187-189° C. $^1$H NMR (400 MHz, CD$_3$OD) δ 7.42-7.25 (m, 5H), 7.18 (d, J=8.3 Hz, 2H), 7.12 (t, J=7.4 Hz, 1H), 7.06 (dd, J=8.8, 2.7 Hz, 1H), 6.91 (d, J=8.0 Hz, 2H), 6.86-6.81 (m, 2H), 6.79-6.73 (m, 3H), 5.02 (s, 2H), 3.75 (s, 3H). HPLC purity 97.3% {$t_R$=2.733 min, flow 1 ml/min, [(CH$_3$CN/(0.1% TFA in H$_2$O):70/30]}.HRMS (ESI-ve) m/z calculated for $C_{28}H_{22}NO_6$ (M−H)$^-$ 468.1452, found 468.1451.

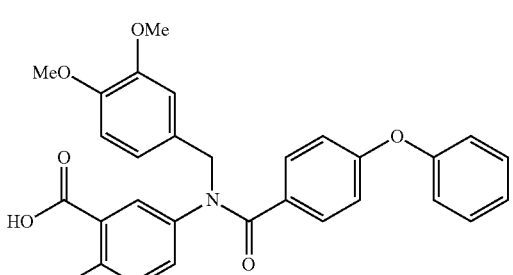

2-Hydroxy-5-(N-(3,4-dimethoxybenzyl)-4-phenoxybenzamido)benzoic acid (20c). A mixture of 19c (0.081 g, 0.157 mmol) in THF (1 mL) and sodium hydroxide (aq. 1 M, 1 mL) was heated at 70° C. in a sealed tube overnight. The solvent was then removed under reduced pressure. Hydrochloric acid (aq. 1 M, 2 mL) was added to the mixture which was then extracted with EtOAc (2×5 mL). The organic extracts were combined, dried (Na$_2$SO$_4$), filtered and the solvent removed under reduced pressure to provide 13c as a white solid (0.053 g, 0.106 mmol, 68%). $^1$H NMR (400 MHz, CD$_3$OD) δ 7.54 (s, 1H), 7.37-7.26 (m, 4H), 7.16-7.05 (m, 1H), 6.96-6.87 (m, 3H), 6.86-6.70 (m, 5H), 6.58 (d, J=8.6 Hz, 1H), 5.01 (s, 2H), 3.78 (s, 3H), 3.75 (s, 3H); HRMS (ESI+ve) m/z 500.1683 [M+H]$^+$ (calcd for $C_{29}H_{26}NO_7$ 500.1704); HPLC purity 97% {$t_R$=8.5 min, flow 1 ml/min, [CH$_3$CN:(0.1% TFA in H$_2$O), 50:50]}.

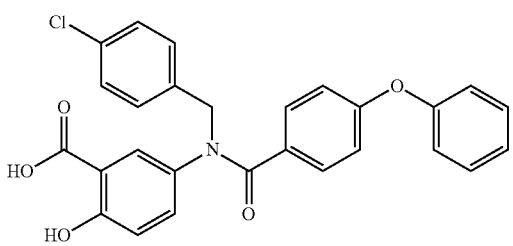

5-(N-(4-Chlorobenzyl)-4-phenoxybenzamido)-2-hydroxybenzoic acid (20d). This was prepared as a white solid (0.060 g, 0.126 mmol, 73%) from 19d (0.084 g, 0.172 mmol) in the same manner as described for 20g. m.p.>150° C. (dec.). $^1$H NMR (400 MHz, CD$_3$OD) δ 7.42 (d, J=2.4 Hz, 1H), 7.35-7.26 (m, 8H), 7.14-7.07 (m, 2H), 6.92 (d, J=8.3 Hz, 2H), 6.80-6.75 (m, 3H), 5.08 (s, 2H). HPLC purity 95.2% {t$_R$=3.27 min, flow 1 ml/min, [(CH$_3$CN/(0.1% TFA in H$_2$O):70/30]}.HRMS (ESI-ve) m/z calculated for C$_{27}$H$_{19}$ClNO$_5$ (M-H)$^-$472.0957, found 472.0955.

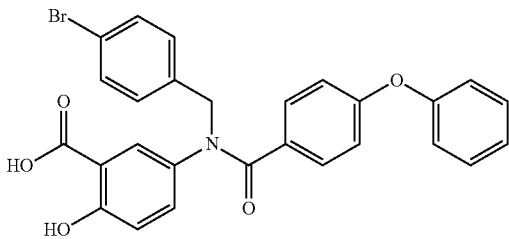 [SMILES: O=C(O)c1cc(N(Cc2ccc(Cl)cc2)C(=O)c2ccc(Oc3ccccc3)cc2)ccc1O]

5-(N-(4-Bromobenzyl)-4-phenoxybenzamido)-2-hydroxybenzoic acid (20e). This was prepared as a white solid (0.105 g, 0.202 mmol, 87%) from 19e (0.125 g, 0.234 mmol) in the same manner as described for 20g. m.p.>198° C. (dec.). $^1$H NMR (400 MHz, CD$_3$OD) δ 7.46-7.43 (m, 3H), 7.35-7.33 (m, 4H), 7.22 (d, J=8.3 Hz, 2H), 7.14-7.10 (m, 1H), 7.01 (dd, J=8.5, 2.6 Hz, 1H), 6.92 (d, J=7.8 Hz, 2H), 6.78 (d, J=8.6 Hz, 2H), 6.72 (d, J=8.7 Hz, 1H), 5.06 (s, 2H). HPLC purity 95.3% {t$_R$=3.39 min, flow 1 ml/min, [(CH$_3$CN/(0.1% TFA in H$_2$O):70/30]}. HRMS (ESI-ve) m/z calculated for C$_{27}$H$_{19}$BrNO$_5$ (M-H)$^-$ 516.0452, found 516.0455.

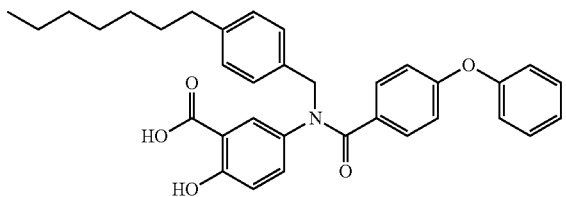 [SMILES: CCCCCCCc1ccc(CN(C(=O)c2ccc(Oc3ccccc3)cc2)c2ccc(O)c(C(=O)O)c2)cc1]

5-(N-(4-heptylbenzyl)-4-phenoxybenzamido)-2-hydroxybenzoic acid (20f). This was prepared from 19f (0.050 g, 0.090 mmol) in the same manner as described for 20g. $^1$H NMR (400 MHz, DMSO-d$_6$) δ 7.40-7.33 (m, 2H), 7.30-7.28 (m, 3H), 7.15-7.11 (m, 3H), 7.09-7.05 (m, 3H), 6.94 (d, J=8.6 Hz, 2H), 6.80 (d, J=8.6 Hz, 2H), 6.67 (d, J=8.7 Hz, 1H), 4.97 (s, 2H), 1.61-1.42 (m, 2H), 1.22 (d, J=8.2 Hz, 10H), 0.9-0.70 (m, 3H). HPLC purity 99.8% {t$_R$=10.460 min, flow 1 ml/min, [(CH$_3$CN/(0.1% TFA in H$_2$O): 80/20]}.HRMS (ESI-ve) m/z calculated for C$_{34}$H$_{36}$NO$_5$ (M+H)$^+$ 538.2580, found 538.2595.

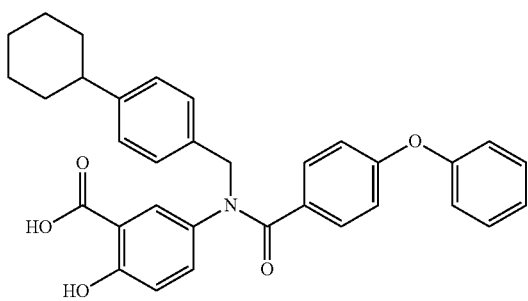 [SMILES: O=C(O)c1cc(N(Cc2ccc(C3CCCCC3)cc2)C(=O)c2ccc(Oc3ccccc3)cc2)ccc1O]

5-(N-(4-Cyclohexylbenzyl)-4-phenoxybenzamido)-2-hydroxybenzoic acid (20g). A mixture of 19g (0.160 g, 0.299 mmol) in THF (1 mL) and sodium hydroxide (aq. 1 M, 1 mL) was heated at 70° C. in a sealed tube for 7 h. The solvent was then removed under reduced pressure. The resulting solid was slurried in HCl (aq. 1 M, 10 mL), filtered, washed with HCl (aq. 1 M, 5 mL), water (10 mL) and dried under vacuum to afford 20g as a white solid (0.139 g, 0.261 mmol, 90%). m.p.>208° C. (dec.). $^1$H NMR (400 MHz, CD$_3$OD) δ 7.47 (d, J=1.7 Hz, 1H), 7.37-7.26 (m, 4H), 7.19 (d, J=8.1 Hz, 2H), 7.13-7.09 (m, 3H), 6.91 (d, J=8.0 Hz, 3H), 6.77 (d, J=8.6 Hz, 2H), 6.65 (d, J=8.7 Hz, 1H), 5.04 (s, 2H), 2.49-2.44 (m, 1H), 1.88-1.17 (m, 5H), 1.43-1.38 (m, 4H), 1.32-1.21 (m, 1H). HPLC purity 98.3% {t$_R$=6.28 min, flow 1 ml/min, [(CH$_3$CN/(0.1% TFA in H$_2$O):80/20]}. HRMS (ESI-ve) m/z calculated for C$_{33}$H$_{30}$NO$_5$ (M-H)$^-$ 520.2129, found 520.2130.

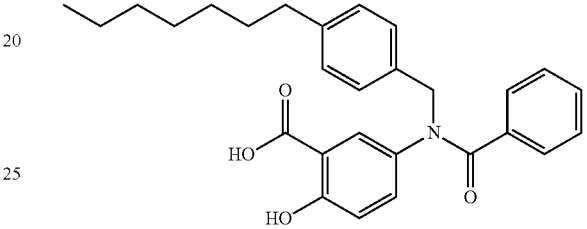

5-(N-(4-Heptylbenzyl)benzamido)-2-hydroxybenzoic acid (20h). The ester 19h (0.045 g, 0.101 mmol) in THF (1 mL) and NaOH (aq. 1 M, 1 mL) were heated at 70° C. overnight in a sealed tube. The solvent was then removed under reduced pressure. The resulting solid was slurried in HCl (aq. 1M, 2 mL), filtered, water (3 mL) and dried under vacuum to afford pure 20h as a white solid (0.039 g, 0.090 mmol, 89%). m.p. 142.8-143.6° C. $^1$H NMR (400 MHz, CD$_3$OD) δ 7.38 (s, 1H), 7.35-7.13 (m, 7H), 7.11 (d, J=8.0 Hz, 2H), 7.01 (s, 1H), 6.67 (d, J=8.8 Hz, 1H), 5.06 (s, 2H), 2.55 (t, J=6.4 Hz, 2H), 1.70-1.51 (m, 2H), 1.40-1.14 (m, 8H), 0.88 (t, J=7.1 Hz, 3H). HPLC purity 96.6% {t$_R$=15.55 min, flow 1 ml/min, [(CH$_3$CN/(0.1% TFA in H$_2$O):70/30]}. HRMS (ESI-ve) m/z calculated for C$_{28}$H$_{30}$NO$_4$ (M-H)$^-$ 444.2180, found 444.2187.

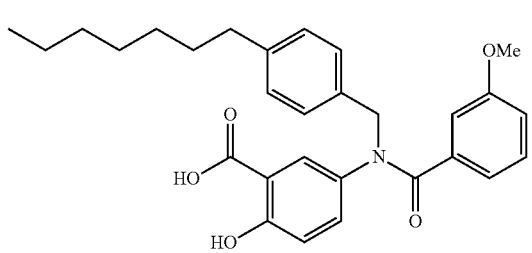 [SMILES: CCCCCCCc1ccc(CN(C(=O)c2cccc(OC)c2)c2ccc(O)c(C(=O)O)c2)cc1]

5-(N-(4-Heptylbenzyl)-3-methoxybenzamido)-2-hydroxybenzoic acid (20i). This was prepared as a white solid (0.046 g, 0.099 mmol, 81%) from 19i (0.058 g, 0.122 mmol) in the same manner as described for 20h. m.p.>81° C. (dec.). $^1$H NMR (400 MHz, CD$_3$OD) δ 7.33 (s, 1H), 7.14-7.04 (m, 8H), 6.83-6.80 (m, 4H), 5.03 (s, 2H), 3.66 (s, 3H), 2.56 (t, J=7.6 Hz, 2H), 1.59-1.53 (m, 2H), 1.29-1.26 (m, 8H), 0.87 (t, J=6.9 Hz, 3H). HPLC purity 99.3% {t$_R$=11.73 min, flow 1 ml/min, [(CH$_3$CN/(0.1% TFA in H$_2$O):70/30]}. HRMS (ESI-ve) m/z calculated for C$_{29}$H$_{32}$NO$_5$ (M-H)$^-$ 474.2286, found 474.2277.

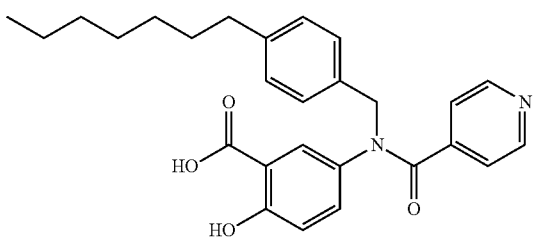 [SMILES: CCCCCCCc1ccc(CN(C(=O)c2ccncc2)c2ccc(O)c(C(=O)O)c2)cc1]

5-(N-(4-Heptylbenzyl)isonicotinamido)-2-hydroxybenzoic acid (20j). This was prepared from 19j (0.079 g, 0.182 mmol) in the same manner as described for 20h. The solvent was then removed under reduced pressure. The obtained solid was slurried in citric acid (aq. sat., 10 mL), filtered, water (2×5 mL) and dried under vacuum to afford 20j as a yellow solid (0.067 g, 0.154 mmol, 85%). m.p. 157.3-158.9° C. $^1$H NMR (400 MHz, CD$_3$OD) δ 8.42 (s, 2H), 7.41 (d, J=2.7 Hz, 1H), 7.32 (d, J=5.0 Hz, 2H), 7.18 (d, J=8.0 Hz, 2H), 7.12 (d, J=7.9 Hz, 2H), 7.06 (dd, J=8.8, 2.8 Hz, 1H), 6.70 (d, J=8.8 Hz, 1H), 5.05 (s, 2H), 2.57 (t, J=7.7 Hz, 2H), 1.59-1.55 (m, 2H), 1.35-1.18 (m, 8H), 0.88 (t, J=6.7 Hz, 3H). HPLC purity 97.8% {t$_R$=4.23 min, flow 1 ml/min, [(CH$_3$CN/(0.1% TFA in H$_2$O):70/30]}. HRMS (ESI-ve) m/z calculated for C$_{27}$H$_{29}$N$_2$O$_5$ (M-H)$^-$ 445.2132 found 445.2134.

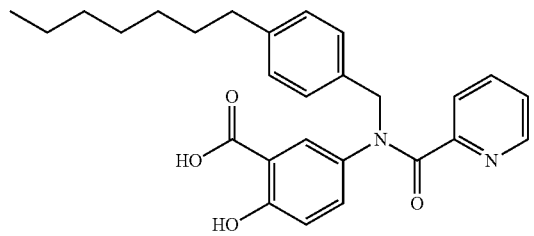 [SMILES: CCCCCCCc1ccc(CN(C(=O)c2ccccn2)c2ccc(O)c(C(=O)O)c2)cc1]

5-(N-(4-Heptylbenzyl)picolinamido)-2-hydroxybenzoic acid (20k). This was obtained as a yellow solid (0.027 g, 0.062 mmol, 87%) from 19k (0.045 g, 0.101 mmol) in the same manner as described for 20j. m.p. required $^1$H NMR (400 MHz, CD$_3$OD) δ 8.35 (s, 1H), 7.71 (t, J=7.7 Hz, 1H), 7.42-7.38 (m, 2H), 7.26 (s, 1H), 7.21 (d, J=7.7 Hz, 2H), 7.11 (d, J=7.8 Hz, 2H), 7.05 (d, J=9.3 Hz, 1H), 6.64 (d, J=8.9 Hz, 1H), 5.07 (s, 2H), 2.57 (t, J=7.7 Hz, 2H), 1.51-1.53 (m, 2H), 1.30-1.26 (m, 8H), 0.88 (t, J=6.6 Hz, 3H). HPLC purity 98.8% {t$_R$=8.72 min, flow 1 ml/min, [(CH$_3$CN/(0.1% TFA in H$_2$O):70/30]}. HRMS (ESI-ve) m/z calculated for C$_{27}$H$_{29}$N$_2$O$_5$ (M-H)$^-$ 445.2132, found 445.2133.

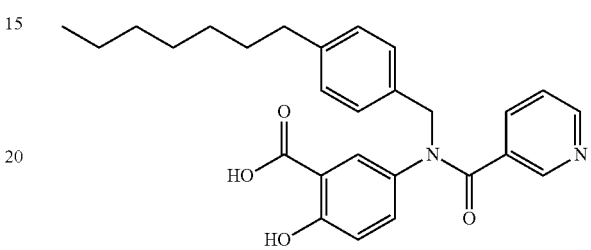

5-(N-(4-Heptylbenzyl)nicotinamido)-2-hydroxybenzoic acid (20l). This was obtained as a yellow solid (0.027 g, 0.062 mmol, 37%) from 19l (0.050 g, 0.111 mmol) in the same manner as described for 20j. $^1$H NMR (400 MHz, CD$_3$OD) δ 8.46 (s, 1H), 7.76 (d, J=9.7 Hz, 1H), 7.43 (s, 1H), 7.32 (s, 1H), 7.18 (d, J=7.7 Hz, 2H), 7.11 (d, J=8.1 Hz, 2H), 7.06 (d, J=7.8 Hz, 1H), 6.71 (d, J=8.6 Hz, 1H), 5.07 (s, 2H), 2.56 (t, J=7.6 Hz, 2H), 1.64-1.52 (m, 2H), 1.34-1.23 (m, 8H), 0.88 (t, J=6.8 Hz, 3H). HPLC purity 97.0% {t$_R$=5.283 min, flow 1 ml/min, [(CH$_3$CN/(0.1% TFA in H$_2$O):70/30]}. HRMS (ESI-ve) m/z calculated for C$_{27}$H$_{29}$N$_2$O$_5$ (M-H)$^-$ 445.2132, found 445.2132.

Scheme 5. Synthesis of the benzamide 33 derived from methyl 4-amino-2-hydroxybenzonate.

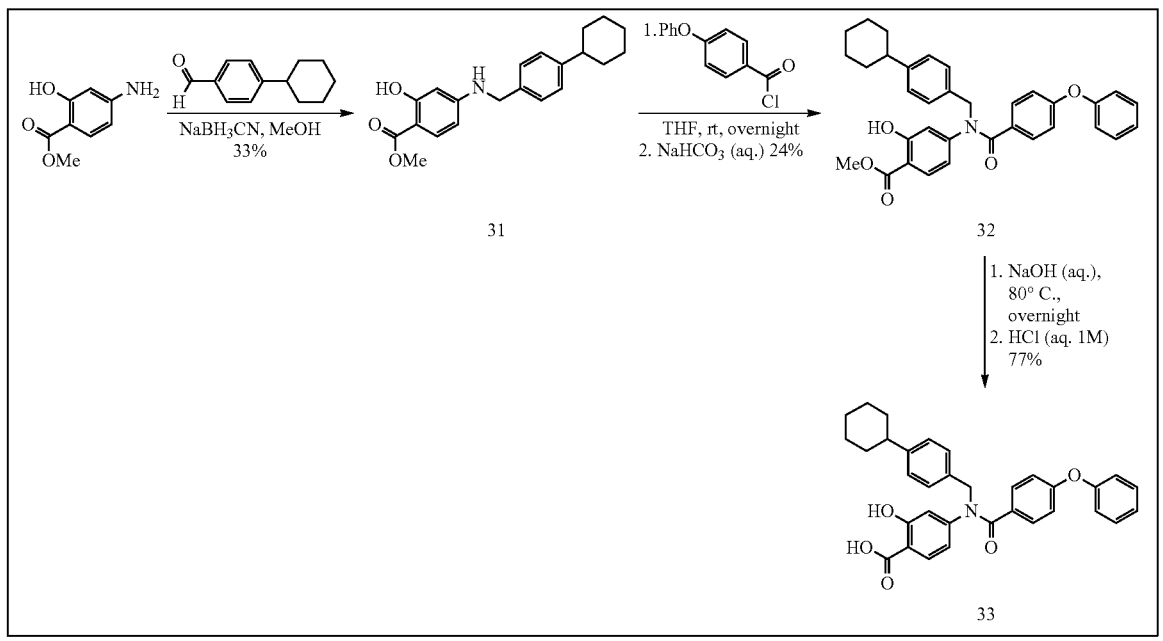

Synthesis of carboxylic acid 33

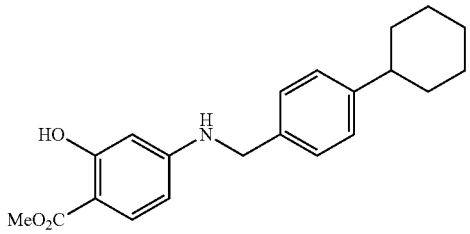 [SMILES: COC(=O)c1ccc(NCc2ccc(C3CCCCC3)cc2)cc1O]

Methyl 4-(4-cyclohexylbenzylamino)-2-hydroxybenzoate (31). To a solution of methyl 4-amino-2-hydroxybenzoate (0.283 g, 1.69 mmol) and 4-cyclohexylbenzaldehyde (0.318 g; 1.68 mmol) in AcOH (1 M in 1,2-dichloroethane, 1.68 mL) was added NaBH(OAc)$_3$ (0.508 g; 2.39 mmol) in one portion and the reaction mixture was stirred at room temperature for 48 h. Water (10 mL) was added and the mixture neutralized using NaHCO$_3$ (sat. aq., 10 mL). The organic layer was extracted with DCM (2×10 mL), dried and evaporated. Chromatography afforded the ester 31(0.191 g, 33%) as a white solid. $^1$H NMR (400 MHz, CDCl$_3$) δ 10.99 (s, 1H), 7.59 (d, J=9.3 Hz, 1H), 7.25 (d, J=7.2 Hz, 2H), 7.19 (d, J=8.2 Hz, 2H), 6.14-6.08 (m, 1H), 4.47 (t, J=5.4 Hz, 1H), 4.30 (d, J=5.3 Hz, 2H), 3.87 (s, 3H), 2.55-2.43 (m, 1H), 1.90-1.68 (m, 5H), 1.49-1.17 (m, 6H); HRMS (ESI+ve) m/z 340.1902 [M+H]$^+$ (calcd for C$_{21}$H$_{26}$NO$_3$ 340.1907).

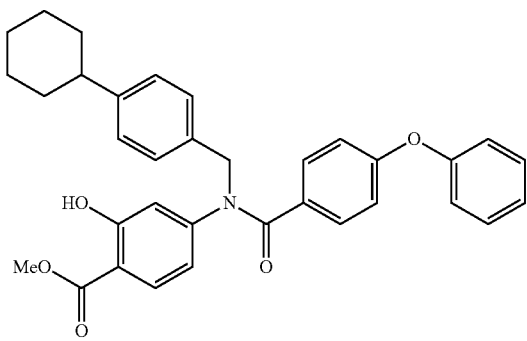 [SMILES: O=C(O)c1ccc(N(Cc2ccc(C3CCCCC3)cc2)C(=O)c2ccc(Oc3ccccc3)cc2)cc1O]

Methyl 4-(N-(4-cyclohexylbenzyl)-4-phenoxybenzamido)-2-hydroxybenzoate (32). This was prepared from 31(0.093 g, 0.274 mmol) and 4-phenoxybenzoyl chloride (0.083 g, 0.357 mmol) in the same manner as described for 30c. Chromatography afforded pure 32 as a colorless oil (0.035 g, 0.065 mmol, 24%). $^1$H NMR (400 MHz, CDCl$_3$) δ 10.77 (s, 1H), 7.59 (d, J=8.6 Hz, 1H), 7.38 (d, J=8.8 Hz, 2H), 7.35-7.31 (m, 1H), 7.22 (d, J=8.1 Hz, 2H), 7.14-7.11 (m, 3H), 7.00-6.93 (m, 2H), 6.79 (d, J=8.8 Hz, 2H), 6.66 (d, J=2.1 Hz, 1H), 6.42 (dd, J=8.6, 2.2 Hz, 1H), 5.09 (s, 2H), 3.90 (s, 3H), 2.63-2.35 (m, 1H), 1.89-1.65 (m, 5H), 1.48-1.08 (m, 6H); HRMS (ESI+ve) m/z 558.2277 (M+Na)$^+$ (calcd for C$_{34}$H$_{34}$NO$_5$ 558.2251).

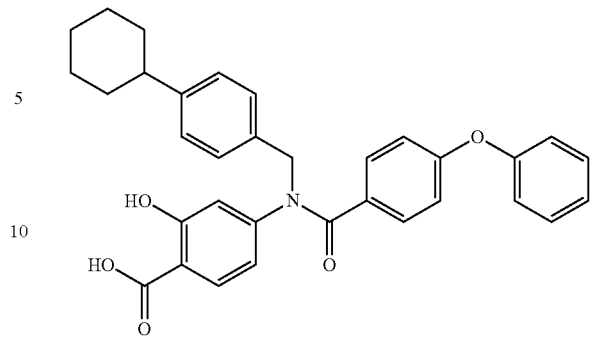

4-(N-(4-Cyclohexylbenzyl)-4-phenoxybenzamido)-2-hydroxybenzoate (33). This was prepared from 32 (0.033 g, 0.061 mmol) in the same manner as described for 13c as a white solid oil (0.025 g, 0.047 mmol, 77%). $^1$H NMR (400 MHz, CD$_3$OD) δ 7.65 (d, J=8.4 Hz, 1H), 7.42-7.32 (m, 4H), 7.21 (d, J=8.1 Hz, 2H), 7.17-7.08 (m, 3H), 6.99-6.89 (m, 2H), 6.80 (d, J=8.8 Hz, 2H), 6.55 (d, J=2.0 Hz, 1H), 6.50 (d, J=2.0 Hz, 1H), 5.10 (s, 2H), 2.63-2.35 (m, 1H), 2.011.75 (m, 5H), 1.49-1.09 (m, 6H); HRMS (ESI+ve) m/z 522.2264 [M+H]$^+$ (calcd for C$_{33}$H$_{32}$NO$_5$ 522.2275); HPLC purity 97% {t$_R$=6.51 min, flow 1 ml/min, [(MeCN:(0.1% TFA in H$_2$O), 80:20]}.

Generation of HA-STAT3 and FLAG-STAT3 Constructs and Generation of HEK293 Cells Stably Expressing HA-STAT3 and FLAG-STAT3

FLAG-Stat3 plasmid was obtained from Addgene (Cambridge, Mass., USA). HA-Stat3 DNA was amplified from FLAG-Stat3 using PCR with HA-pcDNA3 as a vector as described for RhoB. The primers used for PCR were STAT3F-BamH1 CGCGGATCCGCCACCATGGCTCA-GTGGAACCAGCTG (SEQ ID NO:1) and STAT3R-EcoR1 CCGGAATTCTCACATGGGGGAGGTAGCACA (SEQ ID NO:2). The PCR product was digested with BamH1 and EcoR1, and cloned into HA-pcDNA3 vector, further confirmed by sequencing. Ratio (1:1) of pFLAGSTAT3 and pHA-STAT3 plasmid DNAs were co-transfected into HEK-293 cells, and stable G418-resistant (800 µg/ml) clones were selected. Transfections were carried out with LipofectAmine Plus (Invitrogen, Carlsbad, Calif.), according to the manufacturers protocol.

Nuclear Extract Preparation and STAT3 Filter Plate Assay

Nuclear extract preparation was carried out as described in Yu, et al., *Science* 1995; 269(5220):81-83. The STAT3-DNA binding filter plate assay was performed following the manual of the filter plate assay kit (Signosis, Sunnyvale, Calif.), as described for NFκB (Ying, et al., *Blood* 2011; 117(4):1301-1307). The TF Binding buffer was mixed with the STAT3 probe (biotin labeled STAT3 DNA binding sequence) and nuclear extract and incubated at 16° C. for 30 minutes to form the STAT3-DNA complex. The STAT3-DNA complex was then separated from free probe by using a filter plate. After several steps of binding and washing, bound STAT3 probe is retained on the filter in the corresponding well of Filer Plate and the free DNA probe is removed. The bound pre-labeled STAT3 probe was then eluted from the filter plate by centrifuge with elution buffer. Eluted probes were then hybridized into 96-well Hybridization Plate for quantitative analysis. The captured STAT3 probe was further detected by conjugation with streptavidin-HRP. The chemiluminescence of each well was detected by 2104 EnVisionR Multilabel Reader of PerkinElmer (Pekin Elmer, Waltham, Mass., USA) within 5 minutes after mixture with substrates.

Fluorescence Polarization Assay

Fluorescence polarization (FP) assay was conducted based on fluorescence signal differences between free and STAT3-bound fluorescently labeled peptide as described by Schust and Berg (*Anal. Biochem.* 2004; 330(1):114-118; *Chem. Biol.* 2006; 13(11):1235-1242). All reactions contained 10 nM of the fluorescent peptide 5-FAM-G(pTyr) LPQTV-CONH$_2$ (Genscript, Piscataway, N.J., USA) and 100 nM GST-tagged, full-length human STAT3 protein (SignalChem, Richmond, BC, Canada) in 96-well half-area black plates (Corning, Tewksbury, Mass., USA). For evaluating compounds, STAT3 protein was incubated with various concentrations of S3I-1757 or S3I-1756 at room temperature for 60 min in the assay buffer (50 mM NaCl, 10 mM Hepes, pH 7.5, 1 mM EDTA, 0.01% Triton-X100, 2 mM dithiothreitol). Fluorescent peptide was added at a final concentration of 10 nM and incubated for 30 min at room temperature following which the FP measurements were examined by 2104 EnVisionR Multilabel Reader (Pekin Elmer, Waltham, Mass., USA) using FITC FP Dual module with excitation filter of FITC FP 480 and emission filter of FITC FP P-pol535 and S-pol535. The Z' value was derived per the equation $Z'=1-(3SD_{bound}+3SD_{free}) \backslash (mP_{bound}-mP_{free})$, where SD is the standard deviation and mP is the average of fluorescence polarization.

STAT3 Transcriptional Activity

MDA-MB-468 cells were plated into 12-well plate with $4\times10^5$ cells per well. The cells were transiently transfected with pLucSRE, pLucTKS3 or STAT3-C with β-gal and then were treated with vehicle, S3I-1756 or S3I-1757 for 48 hours. Then cytosolic extracts of equal total protein were prepared from S3I-1757-treated or -untreated and analyzed for luciferase activity using a TD-20/20 luminometer (Turner Designs, Sunnyvale, Calif., USA) described by us previously.

Co-localization

HEK-293/FLAG-Stat3/HA-Stat3 cells were cultured (4000 cells per well) with G418 400 ug/ml in 8 well chamber slide. The cells were treated with S3I-1757 or S3I-1756 for 1 hour, 2 hours, or 4 hours. The cells were then rinsed with phosphate buffered saline (PBS), fixed with ice-cold methanol for 15 minutes, washed 3 times in PBS, permeabilized with 0.2% Triton X-100 for 15 minutes, and further washed 3-4 times with PBS. Cells were then blocked in 1% bovine serum albumin (BSA) for 30 min and incubated with anti-HA (Santa Cruz, Santa Cruz, Calif., USA) or anti-FLAG (Sigma, St. Louis, Mo., USA) primary antibody at 1:100 dilution at 4° C. overnight. Subsequently, cells were rinsed 4-5 times in PBS, incubated with Alexa fluor secondary antibody (Invitrogen, Carlsbad, Calif., USA) for 1 hour at room temperature in the dark. Cells were then washed 5 times with PBS, covered with cover slides with VECTASHIELD mounting medium containing DAPI (Vector Lab, Inc., Burlingame, Calif.), and examined immediately under Zeiss Upright Fluorescence Microscope (Zeiss, Thornwood, N.Y., USA).

STAT3 Nuclear accumulation

MDA-MB-468 cells were plated at 4000 cells/well in 8-chamber slide. The cells were treated the following day with Vehicle, S3I-1756 or S3I-1757 for 2 hours, 4 hours, or 18 hours. Cells were fixed, washed, and permeabilized as describe above. Specimens were then blocked in 1% bovine serum albumin (BSA) for 30 min and incubated with anti-pSTAT3 (Cell Signaling), antibody at 1:50 dilution at 4° C. overnight. Subsequently, cells were rinsed 4-5 times in PBS, incubated with Alexa Fluor secondary antibody for 1 hour at room temperature in the dark. Specimens were then washed 5 times with PBS, covered with cover slides with VECTASHIELD mounting medium containing DAPI (Vector Lab, Inc., Burlingame, Calif.), and examined immediately under Zeiss Upright Fluorescence Microscope (Zeiss, Thornwood, N.Y., USA).

MTT Assay

MTT assay was performed exactly as described by Balasis, et al., *Clin. Cancer Res.* 2011; 17(9):2852-2862, to determine the effects of S3I-1757 on cell proliferation. Cells were plated in a 96 well tissue culture plate (2000 cells per well) and incubated for 12 hours. After incubation the cells were treated with vehicle S3I-1757 or S3I-1756 for 48 hours. After incubation, freshly prepared MTT (3 mg/ml) in 1×PBS was added to each well and incubated for 3 hours and the plate was read at 570 nm.

Colony Survival Assay

Cells were cultured at 500 cells per well in 12-well plate with regular growth medium. Cells were treated by vehicle, and 1757 at 50 μM, 100 μM and 200 μM on the following day. And Cells were allowed to grow for 2-3 weeks until the colonies were visible. 3 mg/ml MTT in PBS buffer (Sigma, St. Louis, Mo., USA) was used to stain the colonies for 4 hours.

Wound Healing Assay

A549, MDA-MB-231 and H460 cells were seeded at $6\times10^5$ cells per dish into 60 mm plate and allowed to grow overnight. Wounds were made the following day by scratching the cells with pipette tips (1-10 μL). Cells were treated with vehicle, S3I-1756 or S3I-1757 and allowed to migrate into the scratched area for 16 hours in regular growth medium. The migration of cells was visualized at 10× magnification using a Leica Microscope at time 0 (right before the drug was added) and 16 hours after vehicle, S3I-1756, or S3I-1757 treatments.

Invasion Assay

Invasion assay was performed in BD BioCoat™ Matrigel™ Invasion Chamber in 24-well plates. A549, MDA-MB-468, MDA-MB-231 and H460 cells were seeded at 25,000 cells/insert in the top chamber over the Matrigel. The bottom chamber contains 20% FBS as the "chemoattractant." Vehicle, S3I-1756, or S3I-1757 were added the following day. The cells were incubated for 48 hours, after which the cells in the top chamber were carefully removed and the filter membranes containing the invaded cells on the outside of the filter were fixed with methanol, stained with crystal violet and photographed.

Anchorage Independent Growth by Soft Agar Assay

Soft agar colony formation assays were performed in 12-well plate as described in Balasis, et al., *Clin. Cancer. Res.* 2011; 17(9):2852-2862. Cells were seeded at 2000 cells per well in regular growth media containing 0.3% agar (Sigma) and S3I-1757 was added the following day. Colonies were allowed to grow for 3-4 weeks, and quantified by staining with 1 mg/mL MTT (Sigma, St. Louis, Mo., USA) overnight.

Molecular Docking and Modeling

The GLIDE docking software (available from Schrodinger, Inc.) was employed to dock small molecule 3D structures from NCI Plated Set to the ApY*LK site derived from the X-ray crystal structure of the STAT3 dimer bound to DNA (18). Schrodinger's Maestro 9.1 was used as the primary graphical user interface. Schrodinger's LigPrep 2.41 was used to prepare molecules for docking and Schrodinger's Protein Preparation workflow was used in the preparation of the protein structure. Schrodinger's GLIDE 5.6 was used for the generation of grid files and docking Initially, structures were subjected to docking with GLIDE SP and then the structures from each SP job were subjected to GLIDE XP docking Generally at least three poses were saved for each run for visual inspection. PyMol (Schrodinger, Inc.) was used for graphical presentation of the results in the figures.

Effects of Inhibitors on the Levels of P-STAT3, P-Erk, P-Akt, Bcl-xL, Survivin, MMP9 and Cyclin D1 by Immunoblotting MDA-MB-468 cells were treated with vehicle (DMSO), S3I-1757 at 50 μM, 100 μM and 200 μM, and S3I-1756 at 200 μM for 18 hours. Cells were then lysed with RIPA buffer (20 mM Tris-HCl (pH 7.4), 5 mM EDTA, 10 mM $Na_4P_2O_7$, 100 mM NaF, 2 mM $Na_3VO_4$, 1% NP-40,1 mM PMSF and 10 mg/ml aprotinin) The cell lysates were denatured by boiling with 5×SDS-PAGE sample buffer for 5 minutes and run on SDS-PAGE gel. The proteins were then transferred to membranes that were blocked with 5% non-fat milk in Tris Buffer Saline with 0.1% Tween-20 (TBST) buffer for 30 minutes at room temperature, and incubated with primary antibodies (pY705STAT3, pAKT, AKT, pERK½, MMP9, and CyclinD1) 4° C. overnight at dilution of 1:1000 in 3% BSA, followed by washing and incubation with secondary antibody at dilution of 1:1000 in 5% non-milk Tris Buffer Saline with 0.1% Tween-20 (TBST) buffer for 1 hours at room temperature. The membranes were then washed with 1×PBS buffer for 10 minutes for 3 times and developed with ECL kit (PerkinElmer, Waltham, Mass., USA).

Immunoprecipitation and Immunoblotting

HEK-293/FLAG-STAT3/HA-STAT3 cells were treated for 4 h with vehicle, S3I-1757, S3I-1756, Ac-G{pTYR}LPQTV-AAVLLPVLLAAP-NH2 (SEQ ID NO:3) or Ac-GYLPQTV-AAVLLPVLLAAP-NH2 (SEQ ID NO:4) and then lysed in 20 mM Tris-HCl (pH 7.4), 5 mM EDTA, 10 mM $Na4P_2O_7$, 100 mM NaF, 2 mM $Na_3VO_4$, 1% NP-40,1 mM PMSF and 10 mg/ml aprotinin. For EGF stimulation group, HEK-293/FLAG-STAT3/HASTAT3 cells were treated by 100 ng/ml EGF for 30 minutes before making cell lysate. Protein A or G agarose (EMD Millipore, Billerica, Mass., USA) was washed twice with PBS and restore to 50% slurry with PBS. 500 μg of lysate were pre-cleared by mixture of protein A and protein G-agarose for 1 h at 4° C. and then remove protein A and G-agarose by centrifuge at 1300 rpm for 3 minutes. And then 500 μg of lysate was immunoprecipitated with 50 ng of HA antibody overnight at 4° C. on shaker and then capture the immunocomplex by adding 100 μl Protein A and G agarose/sepharose bead slurry for 1 hour at 4° C. Samples were washed five times with lysis buffer and then boiled in 5x SDS-PAGE sample buffer and run on SDS-PAGE gel. Protein was transferred to nitrocellulose membrane and then blotted as described above for HA, FLAG, pSTAT3, EGFR, and STAT3.

S3I-1757 Inhibits the Binding of Fluorescein-Labelled GpYLPQTV Phosphotyrosine Peptide to STAT3 Much More Potently than its Closely Related Analogue S3I-1756

SAR studies identified several STAT3 inhibitors. Several examples herein focus on S3I-1757 and its closely related analogue S3I-1756 (FIG. 5A). The potency of these molecules to disrupt the binding of STAT3 to fluorescein-labelled GpYLPQTV phosphotyrosine peptide by fluorescence polarization assays was determined (the GpYLPQTV phosphotyrosine peptide corresponds to amino acids 903-909 from the gp-130 subunit of the IL-6 receptor and is known to bind the STAT3-SH2 domain (Haan, et al., *J. Biol. Chem.* 1999; 274(3):1342-1348; Ren, et al., *Bioorg. Med. Chem. Lett.* 2003; 13(4):633-636). FIG. 5A shows that S3I-1757 inhibits the binding of STAT3 to the phosphotyrosine peptide in a concentration-dependent manner with an $IC_{50}$ value of 13.5±0.5 μM. In contrast, the closely related analogue S3I-1756 had little effects with concentrations as high as 400 μM (FIG. 5A). This data shows that replacing the cyclohexyl group in S3I-1757 with a methoxy group as in S3I-1756 resulted in great (over 26-fold) loss of potency to disrupt STAT3 phosphotyrosine-peptide binding.

Molecular Modeling Indicates that S3I-1757 Binds the STAT3-SH2 Domain in the Same Binding Site where the Native Phosphotyrosine Peptide Binds To determine the mode of binding of S3I-1757 to the STAT3-SH2 domain, the docking studies disclosed herein were performed. FIG. 5B shows a surface rendering of the SH2 domain of STAT3 with the active analog, S3I-1757, and the inactive analog, S3I-1756, bound based upon GLIDE XP docking. A ligand-protein interaction diagram is also shown in FIG. 5B. FIG. 5B shows that S3I-1757 occupies the phosphotyrosine binding site of STAT3. Furthermore, the salicylic acid group of S3I-1757 interacts with SH2 domain amino acids (i.e. Arg-609 and Lys-591) known to interact with P-Y-705 of STAT3 (Becker, et al., *Nature* 1998; 394 (6689):145-151). The experimentally observed greater potency of S3I-1757 compared to S3I-1756 is most likely due to a number of factors as illustrated in FIG. 5B: (a) S3I-1757 forms 4 hydrogen bonds (H-bonds between Arg-609 and Glu-612) in the phospho-tyrosine binding pocket, whereas S3I-1756 only forms 3 (H-bonds between Val-637, Arg-609 and Lys 591); (b) S3I-1757 forms 2 excellent cation-π interactions with Lys 591 (with an N to phenyl ring centroid distance of 3.9 A for the salicylate phenyl group and an N to phenyl ring centroid distance of 3.5 A for the phenyl group to which the cyclohexyl substituent is attached); (c) S3I-1756 forms 2 weaker cation-π interactions with Lys 591 (with an N to phenyl ring centroid distance of 4.6 A for the salicylate phenyl group and an N to phenyl ring centroid 4.5 A for the phenyl group to which the phenoxy group is attached); (d) the surface rendering of the protein in FIG. 5B shows that the cyclohexyl substituent of S3I-1757 is buried in a pocket with a rather negative electrostatic potential whereas the phenoxy substituent of S3I-1756 is similarly buried, although not as deeply and the π electron system of the phenoxy substituent would not interact favorably with this negatively charged environment; (e) the methoxy-phenyl substituent of S3I-1756 is mostly solvent exposed and forms almost no interactions with the protein.

Co-Immunoprecipitation and Co-Localization Experiments Reveal that S3I-1757 but not S3I-1756 Disrupts Intracellular STAT3-STAT3 Dimerization and STAT3-EGFR Binding The data from the FP assays of FIG. 5A coupled with the molecular modeling results of FIG. 5B indicates that S3I-1757 inhibits STAT3 dimerization. However, the FP assay only measured the ability of S3I-1757 to displace the 7 amino acid fluorescein-labelled GpYLPQTV phosphotyrosine peptide from the SH2 domain of STAT3 protein in vitro. Therefore, it was determined if the intracellular reciprocal binding of 2 full-length STAT3 proteins is inhibited. To this end, an assay was developed to measure directly STAT3-STAT3 dimerization in intact cells by cloning HA-tagged STAT3 and FLAG-tagged STAT3, generating HEK293 cells that stably co-express HA-STAT3 and FLAG-STAT3 and using these cells for coimmunoprecipitation and co-localization. FIG. 6A shows that FLAG-STAT3 co-immunoprecipitated with HA-STAT3 in HEK293 cells that co-express FLAG-STAT3 and HA-STAT3 but not in empty vector-transfected HEK293 cells (Vector). This assay was validated by treating the FLAG-STAT3/HA-STAT3 HEK293 cells with tyrosine phosphorylated or nonphosphorylated GYLPQTV peptide fused to a membrane-translocating sequence (MTS) to allow cell uptake. FIG. 6A shows that, in vehicle-treated cells (V), FLAG-STAT3 co-immunoprecipitated with HA-STAT3, and that treatment with phosphorylated GpYLPQTV (P-Pep) but not non-phosphorylated GYLPQTV (Pep) inhibited FLAG-STAT3 from co-immunoprecipitating with HA-STAT3. To determine that the compounds can inhibit the binding of HA-STAT3 to FLAG-STAT3, HA-STAT3/FLAGSTAT3/HEK293 cells were treated with vehicle (V), S3I-1757 or S3I-1756 and the cells were processed for immunoprecipitation with HA antibodies and immunoblotted with FLAG antibodies. FIG. 6A shows that in vehicle-treated cells, FLAG-STAT3 co-immunoprecipitated with HA-STAT3, and that treatment with S3I-1757 inhibited the binding of FLAG-STAT3 to HA-STAT3 in a concentration-dependent manner. In contrast, S3I-1756 did not inhibit this binding with concentrations as high as 200 µM (FIG. 6A). It was also shown that S3I-1757 could disrupt the binding of HA-STAT3 to the EGF receptor since the same STAT3-SH2 domain that is used for STAT3-STAT3 dimerization is also used to bind EGFR on p-Tyr-1068 and p-Tyr-1086 on EGFR. FIG. 6B shows that stimulation of HA-STAT3/FLAG-STAT3/HEK293 cells with EGF increased the levels of EGFR and P-STAT3 that co-immunoprecipitated with HA-STAT3, and that treatment of these cells with S3I-1757 inhibited these interactions. These results indicate that S3I-1757, and by analogy, the other compounds disclosed herein, is capable of inhibiting STAT3-STAT3 dimerization and STAT3 binding to EGFR in intact cells.

HASTAT3/FLAG-STAT3/HEK 293 cells were treated with vehicle, S3I-1757 or S3I-1756 and the cells were processed for immunofluorescence staining for FLAG-STAT3 and HA-STAT3 and analyzed by confocal microscopy. As shown in FIG. 6C, cells treated with vehicle harbored strong yellow color indicating co-localization of FLAG-STAT3 and HA-STAT3. In contrast, cells treated with S3I-1757, but not S3I-1756, demonstrated progressively less yellow color over time, indicating that the dimerization of FLAG-STAT3 and HA-STAT3 was disrupted.

Therefore, using methods that investigated STAT3 intracellular dimerization with tagged STAT3 proteins, it is demonstrated that STAT3-STAT3 protein-protein binding in intact cells was disrupted with a small molecule designed to disrupt phosphotyrosine binding to STAT3-SH2 domain.

Figure 7A:
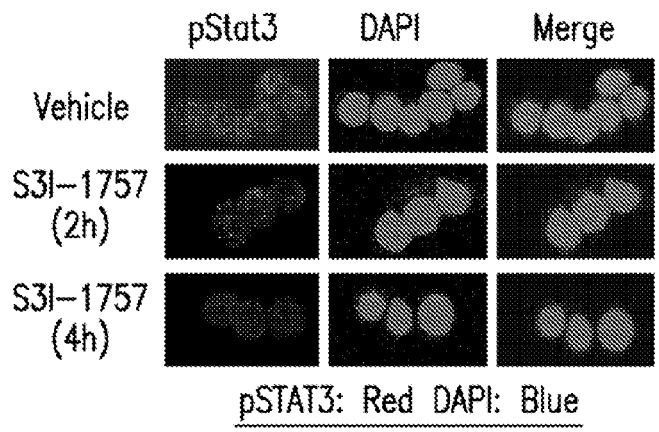
FIGS. 7A and B show results from where MDA-MB-468 cells were plated on cover slides over night and then treated with either vehicle, S3I-1757 or S3I-1756 at the indicated concentration for either 2 or 4 hours (A) or 18 hours (B) and processed for P-STAT3 immunofluorescence.
Figure 7B:
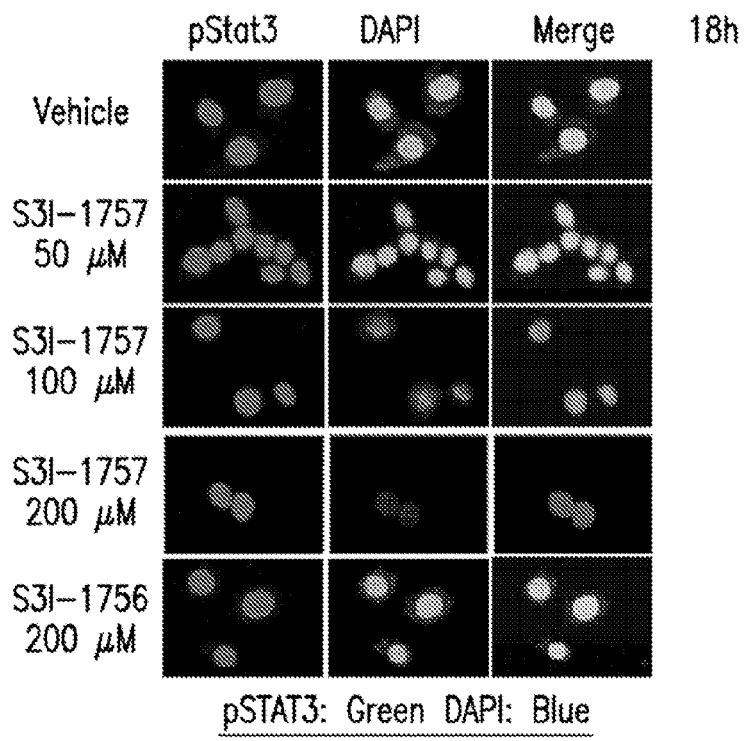
FIG. 7C shows results from where MDAMB-468 and A-549 cells were treated with either vehicle, S3I-1757 or S3I-1756 for the indicated interval of time and the nuclear extract isolated from the treated cells. The nuclear extracts were then incubated with a biotin labeled STAT3 DNA binding probe and the complexes isolated by a STAT3-DNA binding assay. Results are representative of 4 independent experiments.

S3I-1757 but not S3I-1756 Decreases Phosphotyrosine STAT3 Levels in the Nucleus of Human MDAMB-468 Breast Cancer Cells For STAT3 to regulate the expression of its target genes it needs to translocate from the cytosol to the nucleus, a process that requires STAT3 tyrosine phosphorylation and subsequent STAT3-STAT3 dimerization. The fact that S3I-1757 was able to inhibit EGFR-STAT3 binding and STAT3-STAT3 protein-protein binding (FIG. 6) indicates that it would also inhibit the levels of tyrosine phosphorylated STAT3 and its nuclear accumulation. To confirm this is the case, MDA-MB-468 breast cancer cells, which harbor persistently Y-705 phosphorylated STAT3, were treated with either vehicle, S3I-1757 or S3I-1756 for 2 hours and 4 hours and then was subjected to immunofluorescence staining by a specific p-Tyr-705-STAT3 primary antibody and Alexa Fluor 594 secondary antibody in medium containing DAPI to stain the nuclei. FIG. 7A shows that, in vehicle treated cells, pSTAT3 was localized predominantly in the nucleus. In contrast, the levels of p-STAT3 in the nucleus were dramatically decreased in S3I-1757 treated cells particularly after 4 hours of treatment. To determine whether this inhibition is sustained over a longer period of time, MDA-MB-468 cells were treated with various concentrations of S3I-1757 for 18 hours. FIG. 7B shows that S3I-1757-inhibited P-STAT3 nuclear accumulation in a concentration-dependent manner starting at 50 µM. In contrast, S3I-1756 had little effect with concentrations as high as 200 µM.

Figure 7C:
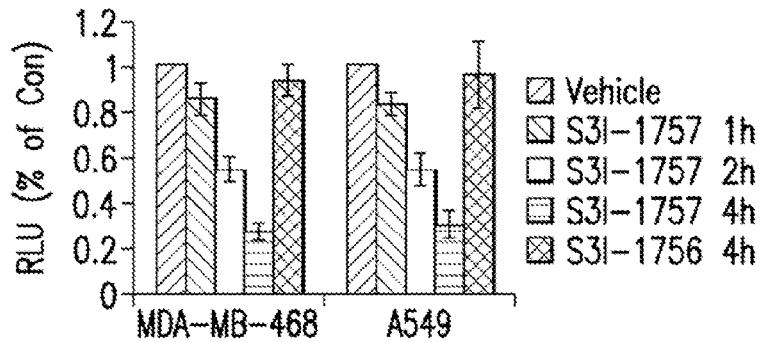

Treatment of Human Breast (MDA-MB-468) and Lung (A-549) Cancer Cells with S3I-1757, but not S3I-1756, Decreases the Amount of Activated STAT3 Capable of Binding to DNA The ability of S3I-1757 to inhibit STAT3-EGFR binding, tyrosine phosphorylation, STAT3-STAT3 dimer formation and nuclear accumulation would be predicted to result in blocking STAT3-DNA binding activity. To demonstrate this, MDA-MB-468 and A-549 cells were treated with vehicle, S3I-1757 or S3I-1756 for 1, 2 or 4 hours and collected nuclear extracts for STAT3-DNA binding activity using a STAT3 filter plate. FIG. 7C shows that nuclear extracts from vehicle treated cells contained activated STAT3 capable of binding the biotin labeled STAT3 DNA binding probe. In contrast, the nuclear extracts from S3I-1757 treated cells contained less activated STAT3 capable of binding the STAT3 DNA binding probe with the least amount found after 4 hours of treatment. FIG. 7C also shows that S3I-1756 did not decrease the amount of STAT3 capable of binding DNA.

Figure 8A:
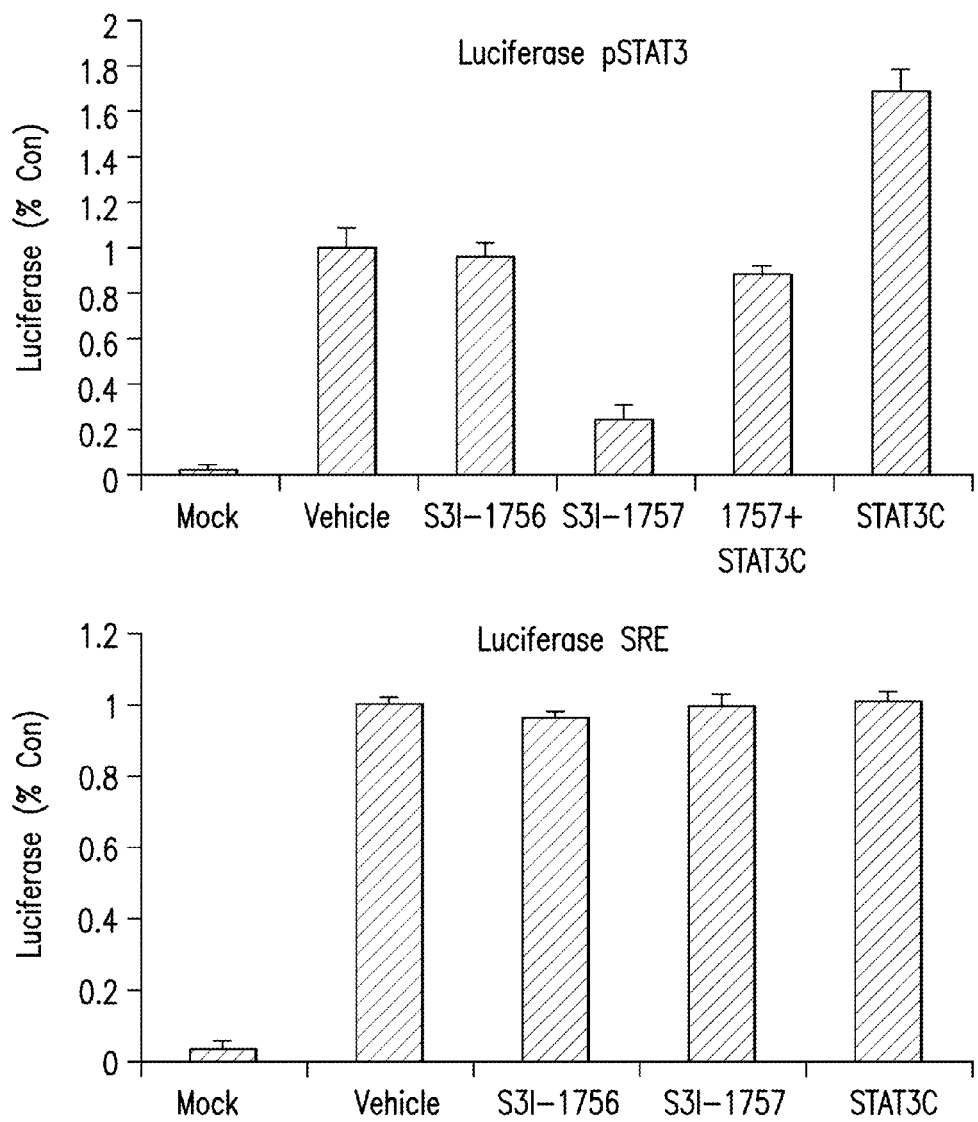
FIG. 8A shows results from where MDA-MB-468 cells were transiently transfected with pLucSRE, pLucTKS3 or STAT3C along with β-gal and then were treated with vehicle, S3I-1756 or S3I-1757. The cytosolic extracts were prepared and analyzed for luciferase activity. The results are representative of 2 independent experiments.

S3I-1757, but not S3I-1756, Inhibits STAT3—but not SRE-Dependent Transcriptional Activation: STAT3-C Rescues this Inhibition The ability of S3I-1757 to inhibit STAT3-dependent transcriptional activation was demonstrated using a luciferase reporter assay. To this end, MDA-MB-468 cells were transiently co-transfected with a STAT3-responsive promoter-firefly luciferase reporter (pLucTKS3) and β-gal reporter used to normalize the transfection efficacy. To determine the selectivity of S3I-1757 to suppress STAT3-dependent over STAT3-independent transcriptional activation, MDA-MB-468 cells were also co-transfected with SRE promoter-renilla luciferase reporter (pLucSRE) and β-gal reporter. FIG. 8A shows that, compared to mock transfected cells, cells transfected with STAT3-responsive reporter (pLucTKS3) had increased luciferase activity in the absence of drug treatment. In contrast, less luciferase activity was observed when the cells were treated with S3I-1757 but not S3I-1756. S3I-1757 inhibited STAT3-dependent but not STAT3-independent transcriptional activity as demonstrated by the minimal effect it had on SREdriven luciferase activity (FIG. 8A). A constitutively-dimerized mutant form of STAT3, STAT3-C, was used to further demonstrate the STAT3-dependence of the inhibition with S3I-1757. STAT3-C spontaneously dimerizes via disulfide bonds in the absence of tyrosine phosphorylation and is therefore not predicted to be inhibited by a small molecule that is designed to mimic phosphotyrosine binding. FIG. 8A shows that transfection of MDA-MB-468 cells with STAT3-C increased the transcriptional activity of the STAT3—but not the SRE-responsive promoter, and rescued from the S3I-1757 inhibition.

S3I-1757 but not S3I-1756 Decreases the Tyrosine Phosphorylation of STAT3 Selectively Over the Phosphorylation of Akt and Erk½, and Decreases the Expression of Genes that are Transcriptionally-Regulated by STAT3

Figure 8B:
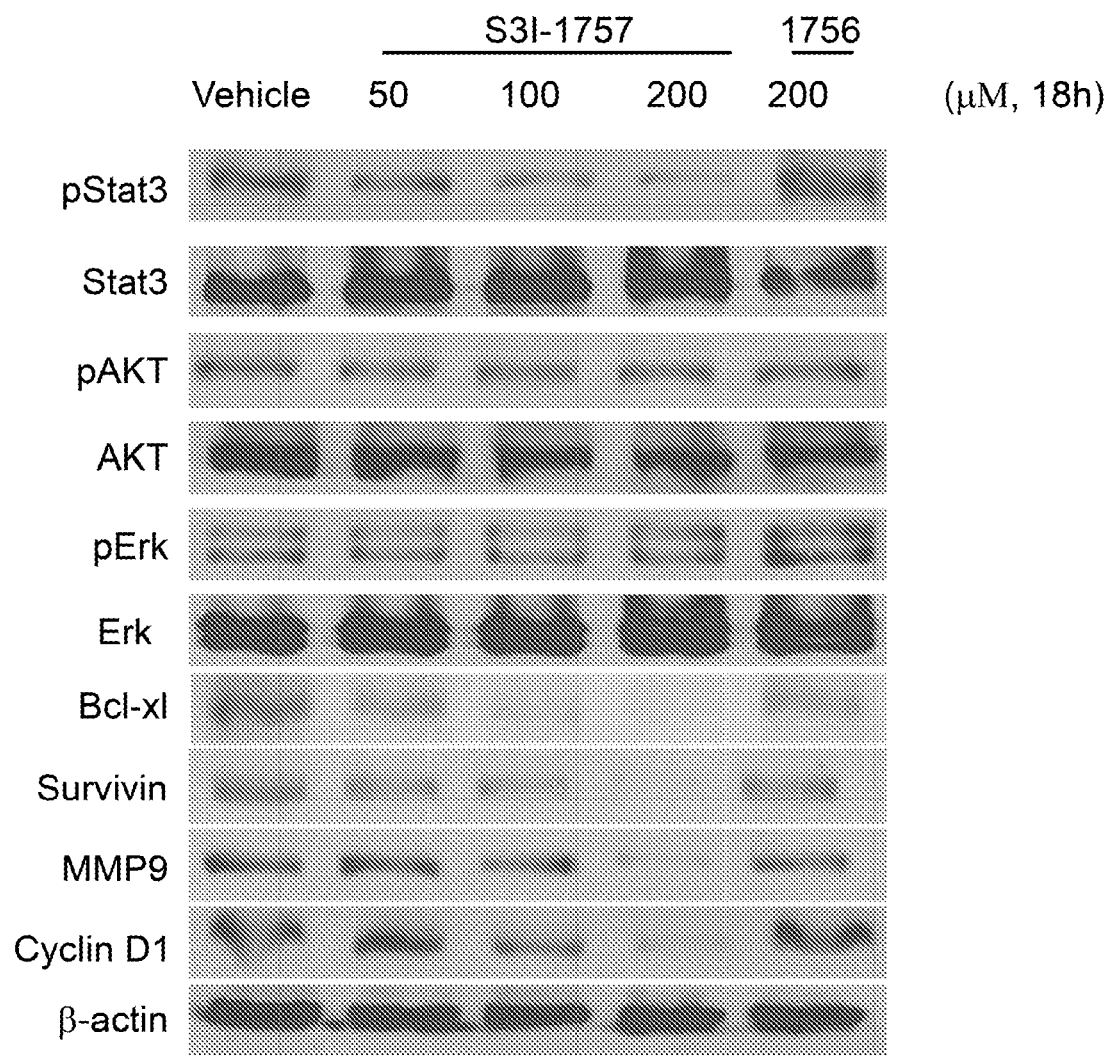
FIG. 8B shows results from where MDA-MB-468 cells were treated for 18 hours with the indicated concentrations of S3I-1757 or S3I-1756 and processed for western immuno-blotting with the indicated antibodies. The results are representative of 3 independent experiments.

FIGS. 5, 6, 7 and 8A demonstrated that S3I-1757 inhibits STAT3 dimerization, accumulation of nuclear P-Y705-STAT3, STAT3-DNA binding and transcriptional activity. The ability of STAT3 to regulate the expression of its target genes is also affected by S3I-1757. First, it was confirmed that S3I-1757 inhibits the phosphorylation of STAT3-Y705 by western blotting and it was determined whether this is selective. To this end, MDA-MB-468 cells were treated with vehicle, S3I-1756 or increasing concentration of S3I-1757 and processed for western blotting. FIG. 8B shows that S3I-1757, but not S3I-1756, inhibited the phosphorylation of STAT3-Y705 in a concentration dependent manner starting at 50 µM. This inhibition was selective for STAT3 over Akt and Erk½ phosphorylation. FIG. 8B also shows that S3I-1757, but not S3I-1756, inhibited the expression of STAT3 target genes such as the anti-apoptotic proteins Bcl-xL and survivin, the cell cycle protein cyclin D1 and the pro-metastatic protein MMP9.

S3I-1757 but not S3I-1756 Inhibits Anchorage-Dependent and -Independent Growth, Migration and Invasion Selectively in Cancer Cells Harboring Constitutively Active STAT3 Over Those that do not.

Figure 9A:
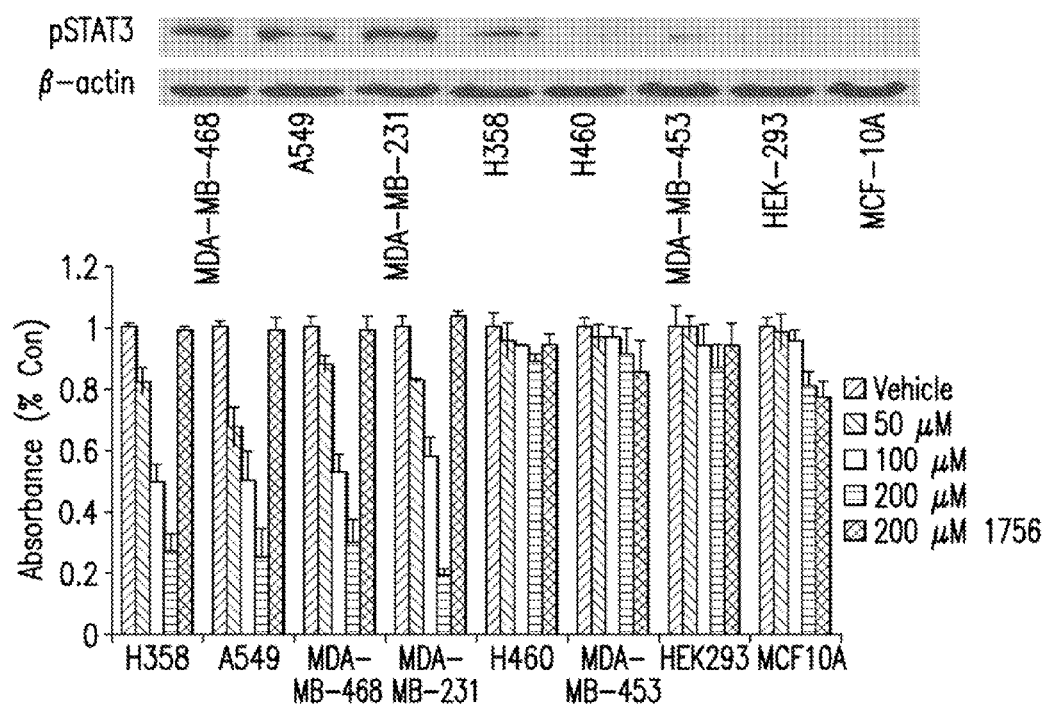
FIG. 9A shows results from where H358, A549, MDA-MB-468 and MDA-MB-231 cells (high P-STAT3) and H460, MDA-MB-453, HEK293, and MCF-10A cells (lowP-STAT3) were plated in 96-well plates and treated with the indicated concentrations of S3I-1757 or S3I-1756 for 48 hours and processed for MTT assays. The levels of P-STAT3 were analyzed by western blotting with a P-Y-705-STAT3 antibody.
Figure 9B:
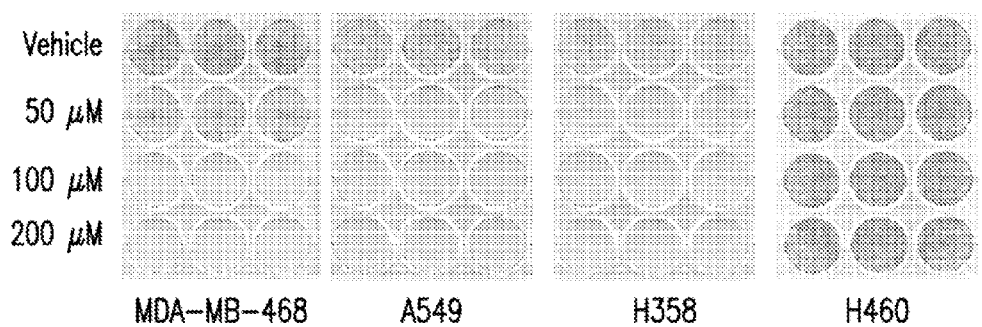
FIG. 9B shows results from where cells were treated exactly as described for (A) except that the cells were plated in 12-well plates and treated for 21 days.
Figure 9C:
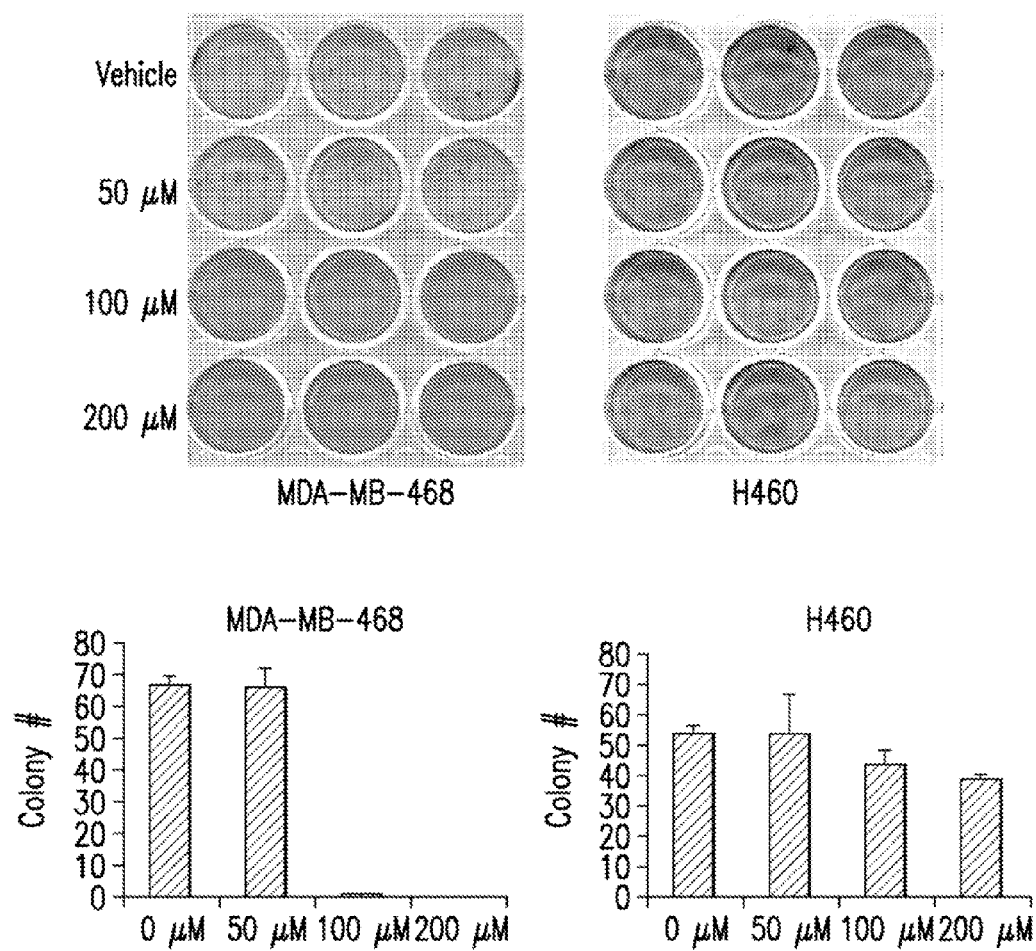
FIG. 9C shows results from where the cells were treated exactly as described for (B) except that they were first seeded at 2000 cells per well in regular growth media containing 0.3% agar (Sigma) and S3I-1757 was added the following day, and colonies were allowed to grow for 3-4 weeks. The experiment was performed once in triplicates.

The data presented in FIGS. 5, 6, 7 and 8 demonstrated that S3I-1757 effectively blocks STAT3 dimerization and constitutive activation and suppresses its ability to persistently up-regulate the expression of genes known to mediate hallmarks of malignant transformation. It was next demonstrated that S3I-1757 can suppress uncontrolled anchorage-dependent and -independent tumor cell growth, migration and invasion. Several cell lines were used, some with persistently Y705 phosphorylated STAT3 and others without (FIG. 9A). FIG. 9A shows that S3I-1757, but not S3I-1756, inhibited in a dose dependent manner anchorage-dependent proliferation by MTT only in cells that harbor (MDA-MB-468, MDA-MB-231, H358, A549) but not in those that do not harbor (H460, MDAMB-453, HEK293 and MCF10A) persistently activated STAT3. Similar results were obtained with colony formation on plastic (FIG. 9B). The effects of S3I-1757 on cancer cell anchorage-independent growth were next determined by soft-agar assay. The results show that S3I-1757 significantly inhibited the anchorage independent growth of cancer cells with constitutively active STAT3 such as MDA-MB-468, but had little effect on anchorage-independent growth of H460 cells which has low activated STAT3 level (FIG. 9C).

Figure 10A:
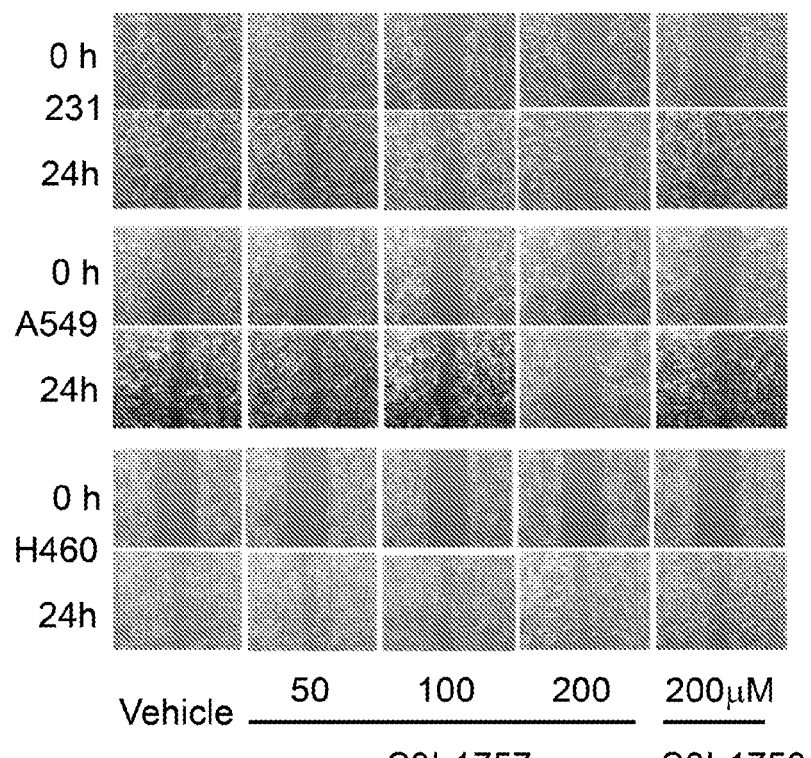
FIG. 10A shows results from a migration assay where MDA-MB-231, A549 and H460 cells were seeded and allowed to grow overnight prior to scratching the cells with pipette tips. Cells were then treated with vehicle, S3I-1756 or S3I-1757 and allowed to migrate into the scratched area for 16 hours in regular growth medium.
Figure 10B:
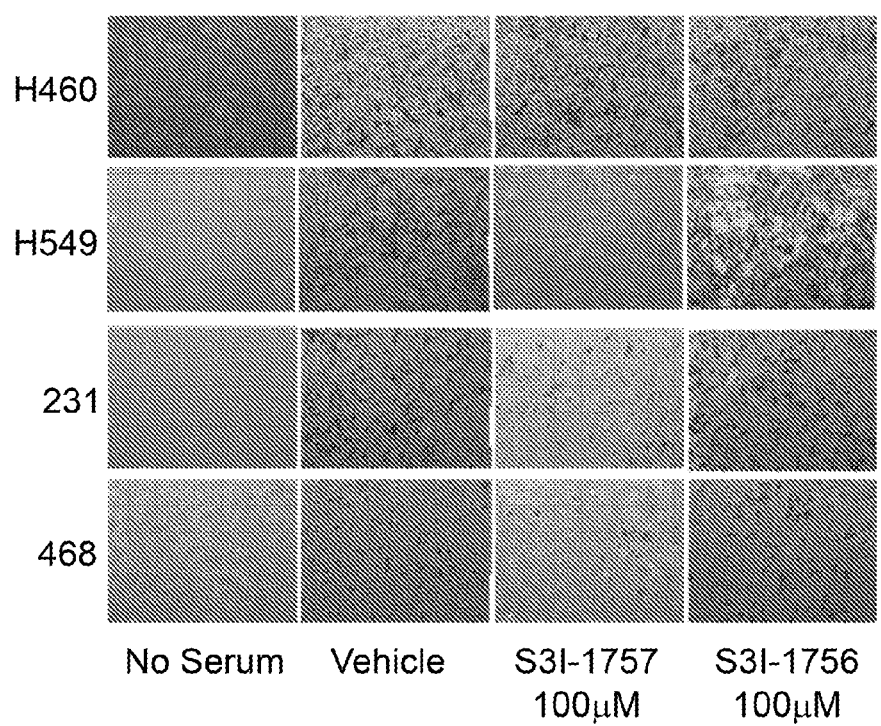
FIG. 10B shows results from an invasion assay where H460, A549, MDA-MB-468 and MDA-MB-231 cells were seeded over the Matrigel in the top chamber of insert, and treated with vehicle, S3I-1756, or S3I-1757 the following day. The cells were incubated for 48 hours, and the invaded cells were fixed with methanol, stained with crystal violet and photographed. Experiments were performed in triplicates with identical results.

The ability of S3I-1757 to inhibit selectively the migration of cancer cells that depend on STAT3 over those that do not was next evaluated by a wound healing assay. The cancer cells were cultured with serum-starved medium for 8 hours before scratching the cells with a pipette tip and treating with increasing concentrations of S3I-1757 for 24 hours. FIG. 10A shows that in the absence of drug, the cells migrated within 24 hours to fill the scratched area. S3I-1757, but not S3I-1756, treatment prevented this migration in cells with persistently activated STAT3 (MDA-MB-231 and A-549). In contrast, the migration of H460 (with low levels of P-STAT3) was minimally affected by the same treatment condition. Finally, the ability of S3I-1757 to inhibit selectively invasion was determined. FIG. 10B shows that S3I-1757 but not S3I-1756, inhibited invasion in MDA-MB-468, MDA-MB-231 and A-549 but not in H-460 cells.

Figure 11A:
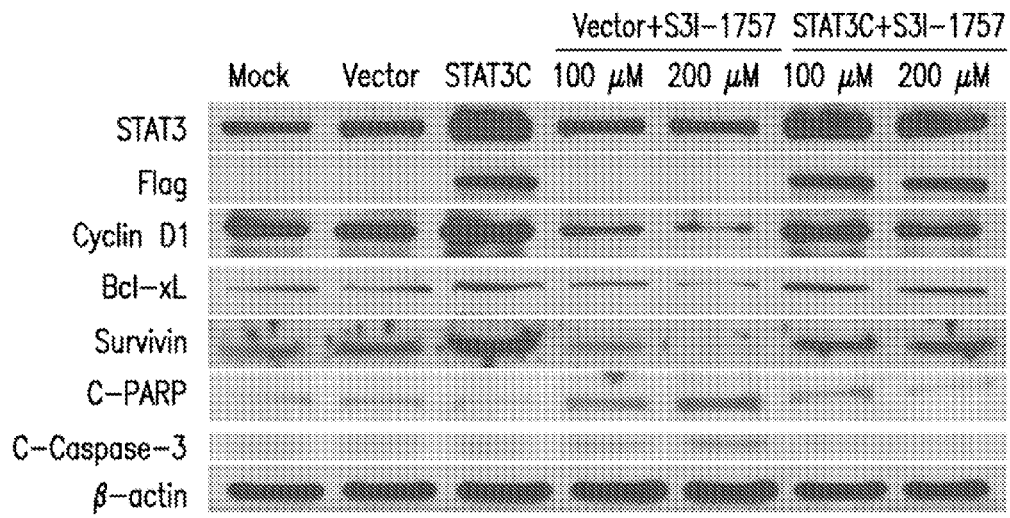
FIG. 11 shows results from where MDA-MB-468 cells were transiently transfected with vector or STAT3C then were treated with S3I-1757. The cells were then processed for western immuno-blotting (A) and for MTT assays (B).
Figure 11B:
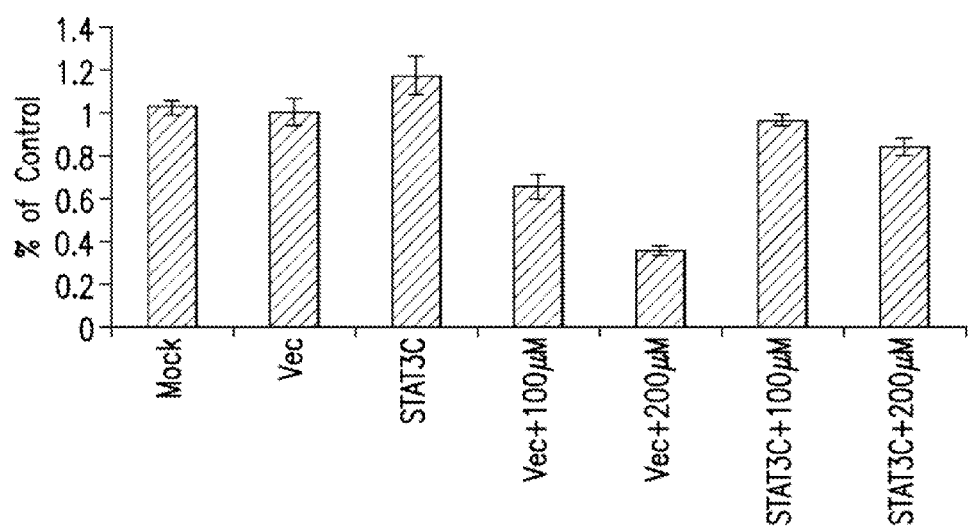

STAT3-C Rescues from S3I-1757 Inhibition of Gene Expression, Tumor Cell Growth, Migration and Invasion as Well as from Apoptosis Induction The fact that S3I-1757 but not its inactive analogue S3I-1756 inhibits malignant transformation selectively in cells that harbor hyperactivated STAT3 indicates that S3I-1757 mediates its effects by inhibiting STAT3. To give further support, the effects of S3I-1757 can be rescued by STAT3-C, a genetically engineered mutant of STAT3 that forms a constitutively dimerized STAT3 through disulfide bonds in the absence of tyrosine phosphorylation. To this end, MDA-MB-468 were transfected cells with STAT3-C, then treated the cells with S3I-1757 and processed the cells for western blotting, cell growth, migration and invasion. FIG. 11A shows that expression of STAT3-C increased the levels of Bcl xL, cyclin D1 and survivin. In contrast, S3I-1757 inhibited the expression levels of these proteins and induced activation of caspase 3 and PARP cleavage. Furthermore, FIG. 11A also shows that ectopic expression of STAT3-C inhibited the ability of S3I-1757 to down regulate the expression of Bcl xL, cyclin D1 and survivin and to induce apoptosis. Similarly, FIG. 11B shows that STAT3-C inhibited S3I-1757 from inhibiting the proliferation/survival of MDA-MB-468 cells as determined by MTT assays.

The effects of STAT3-C on S3I-1757 affect migration and invasion. FIGS. 12A and B show that S3I-1757 inhibited the migration and invasion of MDA-MB-468 cells transfected with vector DNA. In contrast, the ability of S3I-1757 to inhibit migration and invasion was partially rescued in cells transfected with STAT3-C.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

17. The method of claim 13, wherein the compound has the formula
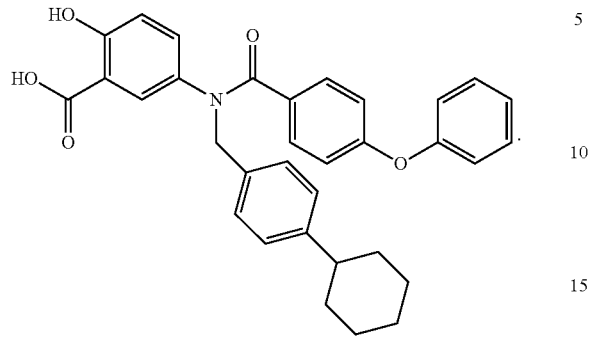

What is claimed is:

1. A compound having Formula I:

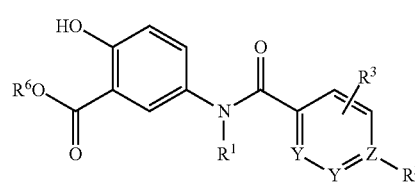

wherein
R$^1$ is H, C$_1$-C$_{10}$ alkyl, C(O)C$_1$-C$_{10}$ alkyl, CO$_2$C$_1$-C$_{10}$ alkyl, benzyl, 4-piperidyl, 3-(4-pyridyl), pyridinyl, or

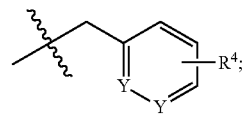

wherein R⁴ is OH, Cl, F, Br, I, cyclohexyl, OC₁-C₁₀ alkyl, C₁-C₁₀ alkyl, C(O)C₁-C₁₀ alkyl, CO₂C₁-C₁₀ alkyl, 4-piperidyl, 3-(4-pyridyl), morpholinyl, pyridinyl, OPh, PO(OEt)₂, or PO(OH)₂;

R² is

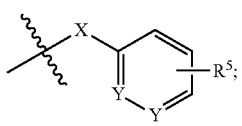

wherein X is O, NH, S, or CH₂, and R⁵ is H, OH, Cl, F, Br, I, cyclohexyl, or C₁-C₁₀ alkyl;

R³ is H, OH, Cl, F, Br, I, OC₁-C₁₀ alkyl, C₁-C₁₀ alkyl, C(O)C₁-C₁₀ alkyl, CO₂C₁-C₁₀ alkyl, NO₂, NH₃, or CN; and R⁶ is H, C₁-C₁₀ alkyl, or a pharmaceutically acceptable counterion;

each Y is, independent of the others, CH or N; and

Z is C or N;

or a pharmaceutically acceptable salt thereof.

2. The compound of claim 1, wherein R¹ is H, C₁-C₁₀ alkyl, C(O)C₁-C₁₀ alkyl, CO₂C₁-C₁₀ alkyl, benzyl, 4-piperidyl, 3-(4-pyridyl), or pyridinyl.

3. The compound of claim 1, wherein R¹ is

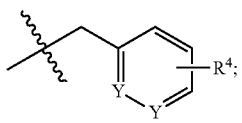

wherein each Y is CH, and R⁴ is OH, Cl, F, Br, I, cyclohexyl, C₁-C₁₀ alkyl, 4-piperidyl, 3-(4-pyridyl), morpholinyl, pyridinyl, or OPh.

4. The compound of claim 1, wherein R¹ is

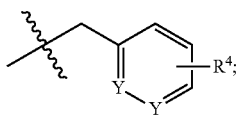

wherein each Y is CH, and R⁴ is cyclohexyl, C₁-C₁₀ alkyl, 4-piperidyl, 3-(4-pyridyl), morpholinyl, or pyridinyl.

5. The compound of claim 4, wherein R⁴ is cyclohexyl.

6. The compound of claim 1, wherein R⁵ is H, OH, Cl, F, Br, or I.

7. The compound of claim 1, wherein X is O.

8. The compound of claim 1, wherein R² is OPh.

9. The compound of claim 1, wherein R³ is H or OCH₃.

10. The compound of claim 1, wherein the compound is

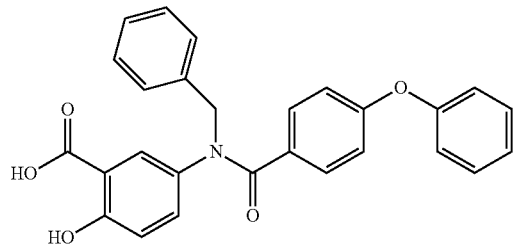

-continued

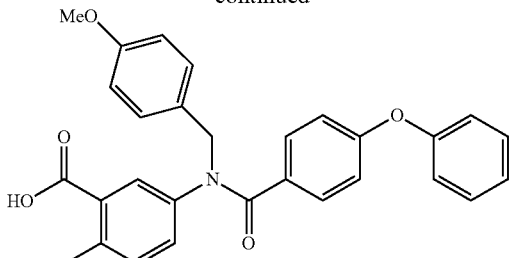

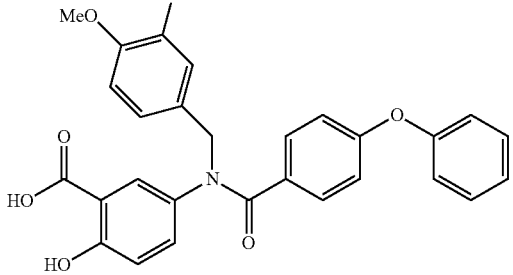

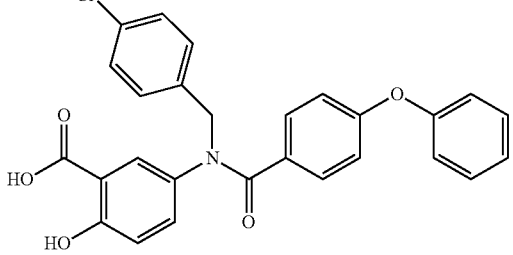

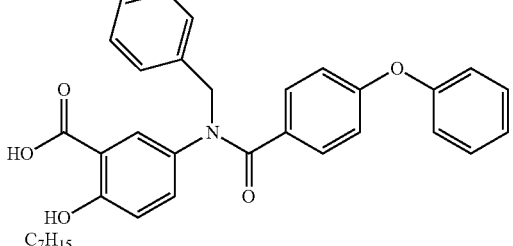

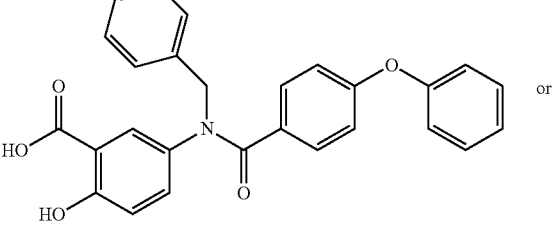

or

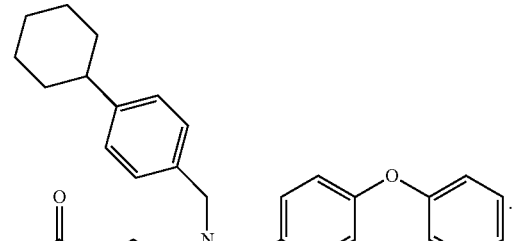

11. The compound of claim 1, wherein the compound has the formula

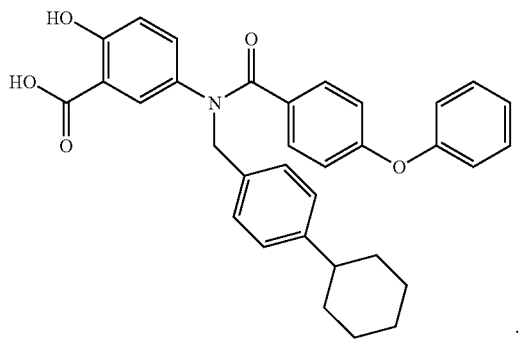 [SMILES: O=C(O)c1cc(N(Cc2ccc(C3CCCCC3)cc2)C(=O)c2ccc(Oc3ccccc3)cc2)ccc1O]

12. A pharmaceutical composition comprising the compound of claim 1 and a pharmaceutically acceptable carrier.

13. A method of reducing or inhibiting tumor growth in an individual with cancer, comprising: administering a therapeutically effective amount of the compound of claim 1 to the individual, wherein the cancer is pancreatic cancer, breast cancer, lung cancer, prostrate cancer, ovarian cancer, colon cancer, gastric cancer, head and neck cancer, melanoma, leukemia, multiple myeloma or lypmpoma.

14. The method of claim 13, wherein STAT3 is persistently tyrosine phosphorylated and constitutively activated in the cancer.

15. The method of claim 13, wherein the compound is

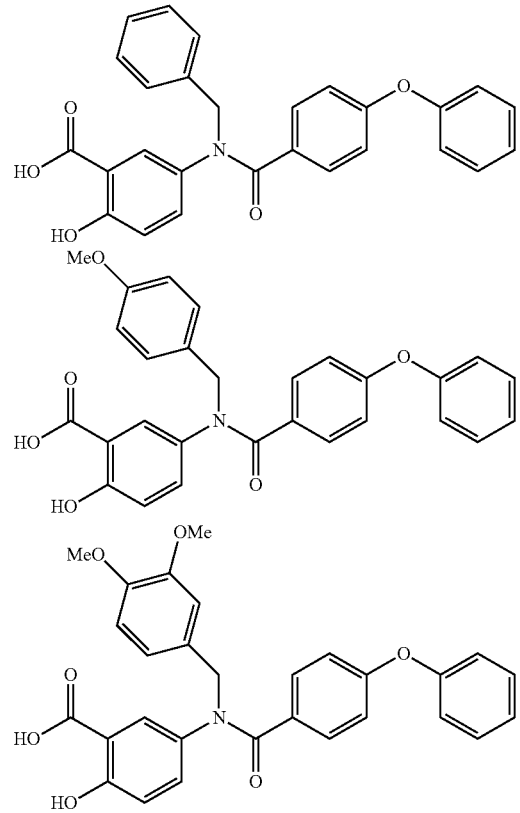

-continued

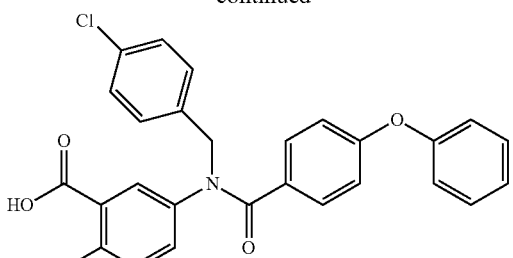

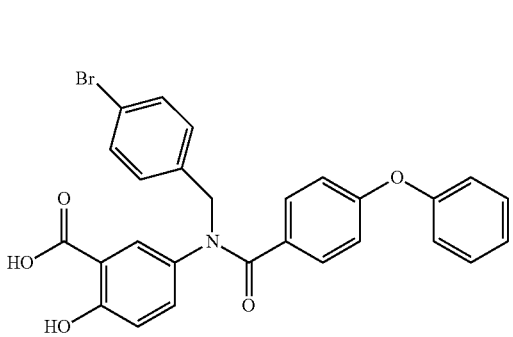

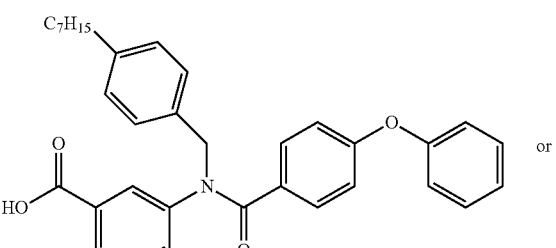

or

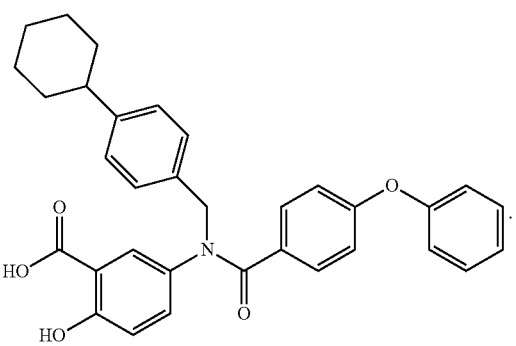 [SMILES: O=C(O)c1cc(N(Cc2ccc(C3CCCCC3)cc2)C(=O)c2ccc(Oc3ccccc3)cc2)ccc1O]

16. A method of inhibiting STAT3-STAT3 dimerization and/or STAT3-EGFR binding in a cell, comprising: administering to the cell an effective amount of the compound of claim 1 to the cell.